United States Patent
Khera et al.

(10) Patent No.: US 10,752,647 B2
(45) Date of Patent: Aug. 25, 2020

(54) N-PHOSPHONOXYMETHYL PRODRUGS OF HYDROXYALKYL THIADIAZOLE DERIVATIVES

(71) Applicant: DAIICHI SANKYO COMPANY, LIMITED, Chuo-ku, Tokyo (JP)

(72) Inventors: Manoj Kumar Khera, Chuo-ku (JP); Naresh Chintaman Dumbre, Chuo-ku (JP); Pasha Khan, Chuo-ku (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 16/492,027

(22) PCT Filed: Mar. 13, 2018

(86) PCT No.: PCT/JP2018/010670
§ 371 (c)(1),
(2) Date: Sep. 6, 2019

(87) PCT Pub. No.: WO2018/169092
PCT Pub. Date: Sep. 20, 2018

(65) Prior Publication Data
US 2020/0040019 A1    Feb. 6, 2020

(30) Foreign Application Priority Data
Mar. 14, 2017    (IN) .............................. 201711008754

(51) Int. Cl.
*C07F 9/6558*    (2006.01)
*A61P 31/04*    (2006.01)

(52) U.S. Cl.
CPC .......... *C07F 9/65583* (2013.01); *A61P 31/04* (2018.01)

(58) Field of Classification Search
CPC ................................................. C07F 9/6558
USPC ............................................... 546/24; 514/89
See application file for complete search history.

(56) References Cited

U.S. PATENT DOCUMENTS 10,399,968 B2 * 9/2019 Khera ..................... A61P 31/04

FOREIGN PATENT DOCUMENTS

EP         2 226 322 A1   9/2010
WO    2017/056012 A1   4/2017

OTHER PUBLICATIONS

International Search Report and Written Opinion dated May 24, 2018, issued in corresponding International Application No. PCT/JP2018/010670, filed Mar. 18, 2018, 10 pages.
Müller, C.E., et al., "Prodrug Approaches for Enhancing the Bioavailability of Drugs with Low Solubility," Chemistry & Biodiversity 6(11):2071-2083, Nov. 2009.

* cited by examiner

*Primary Examiner* — Patricia L Morris
(74) *Attorney, Agent, or Firm* — Christensen O'Connor Johnson Kindness PLLC

(57) ABSTRACT

There is a need for a new antibiotic having a novel mechanism of action, which exhibits strong antibacterial activity not only against sensitive bacteria, but also against resistant bacteria thereof, and at the same time possess excellent solubility and safety profile amenable to human use. As a result of intensive research, the present inventors have found that N-phosphonoxymethyl prodrugs of hydroxyalkyl thiadiazole derivatives represented by general formula (I), a regioisomer, a stereoisomer, or a pharmaceutically acceptable salt thereof possess excellent solubility and safety profile for use in human for the treatment of bacterial infectious diseases.

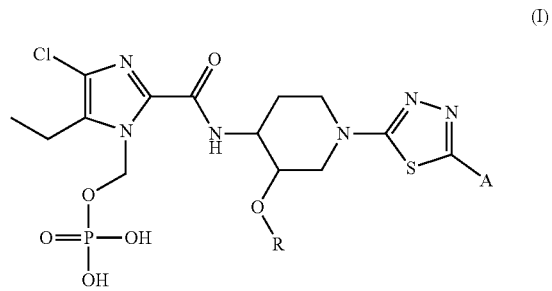

(I)

12 Claims, 6 Drawing Sheets

[Fig. 1]
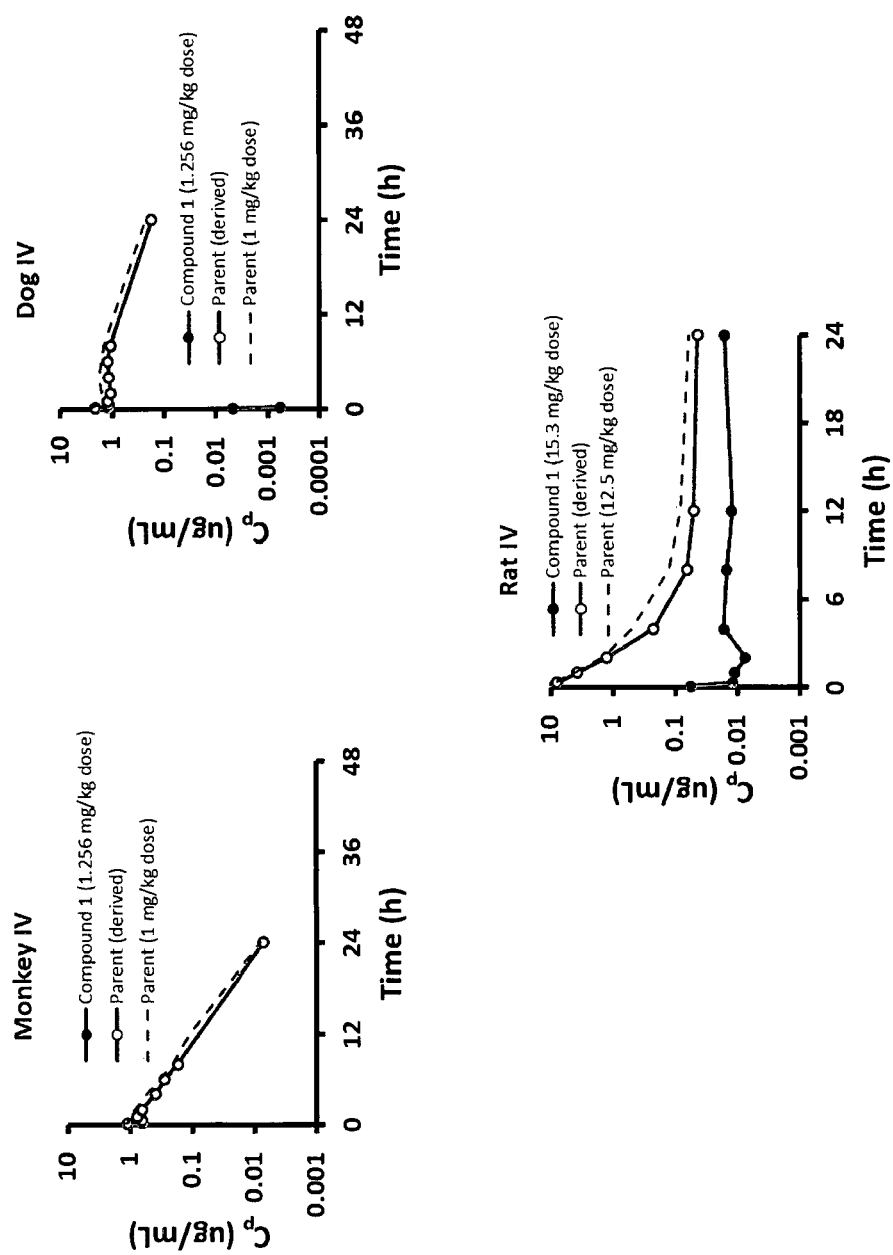

[Fig. 2]
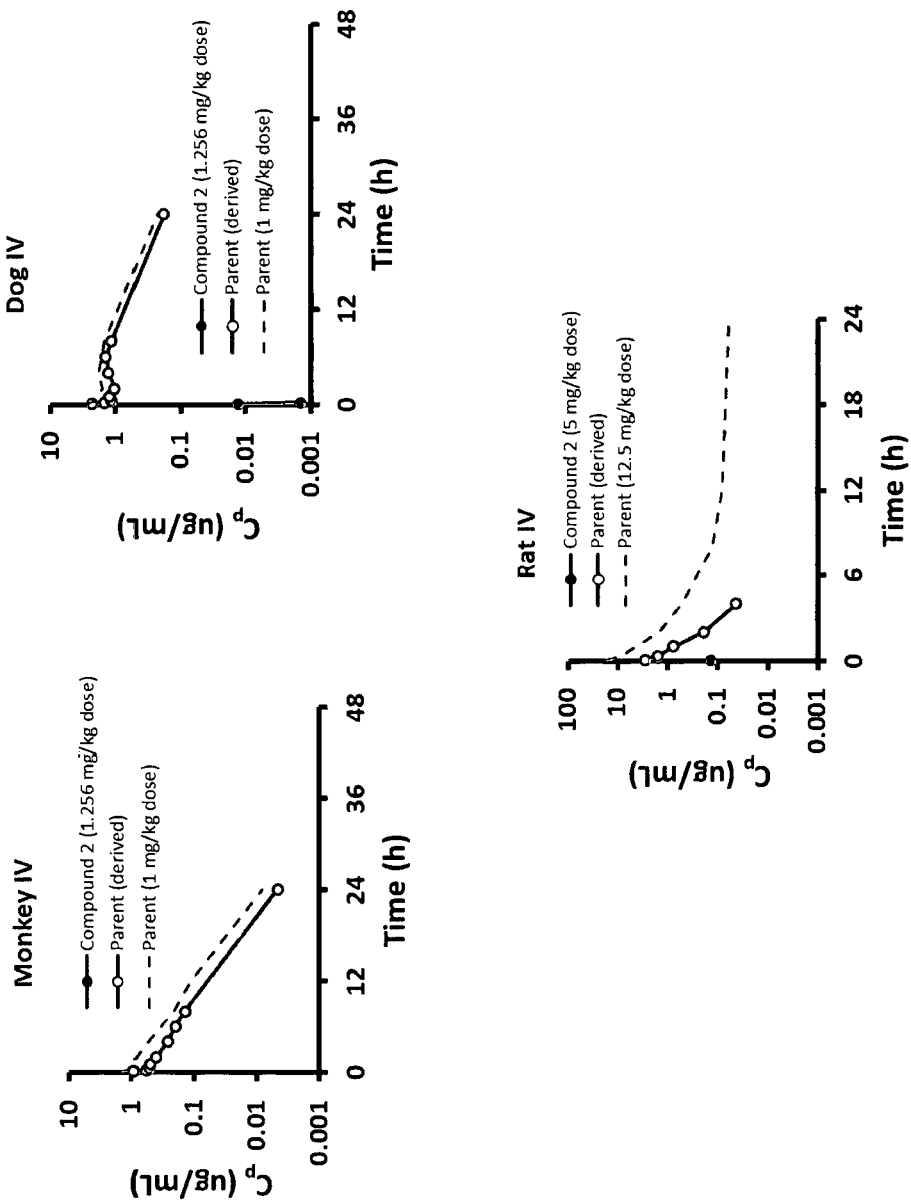

[Fig. 3]
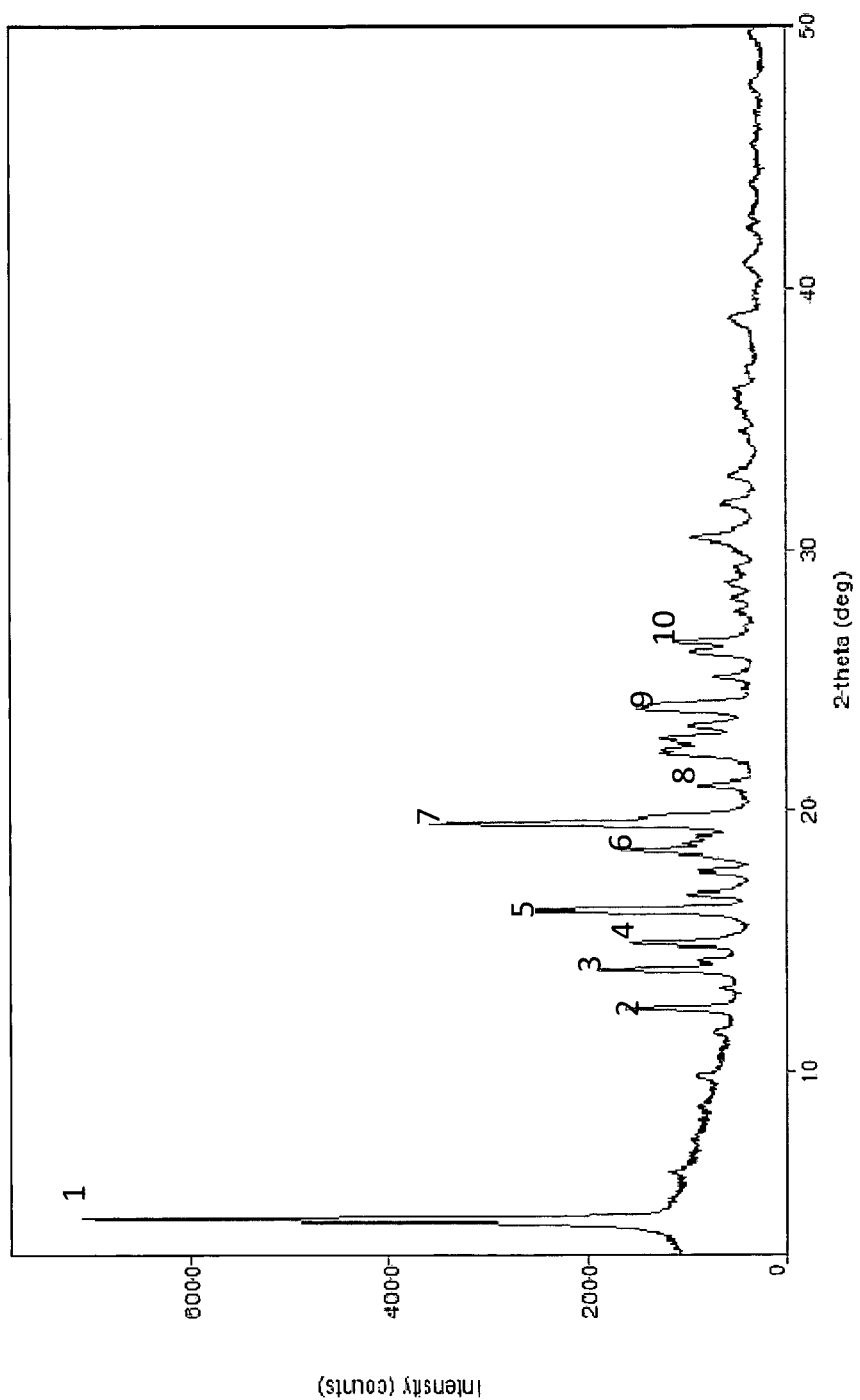

[Fig. 4]
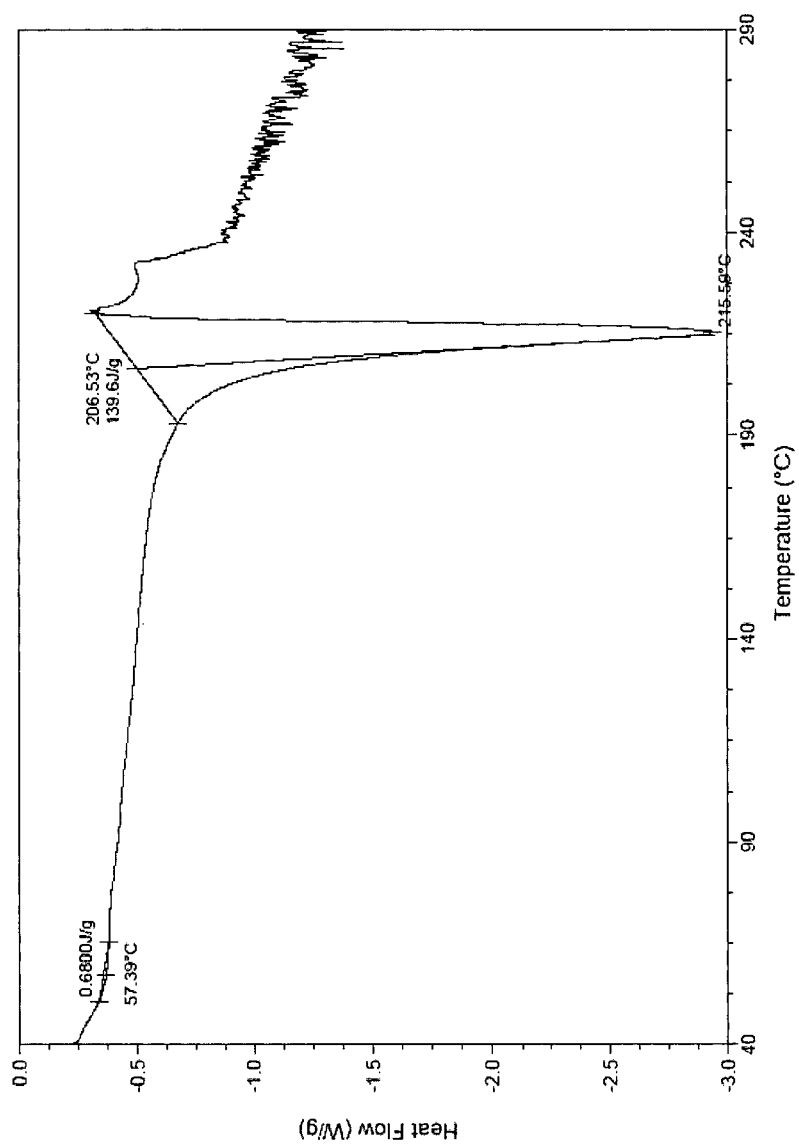

[Fig. 5]
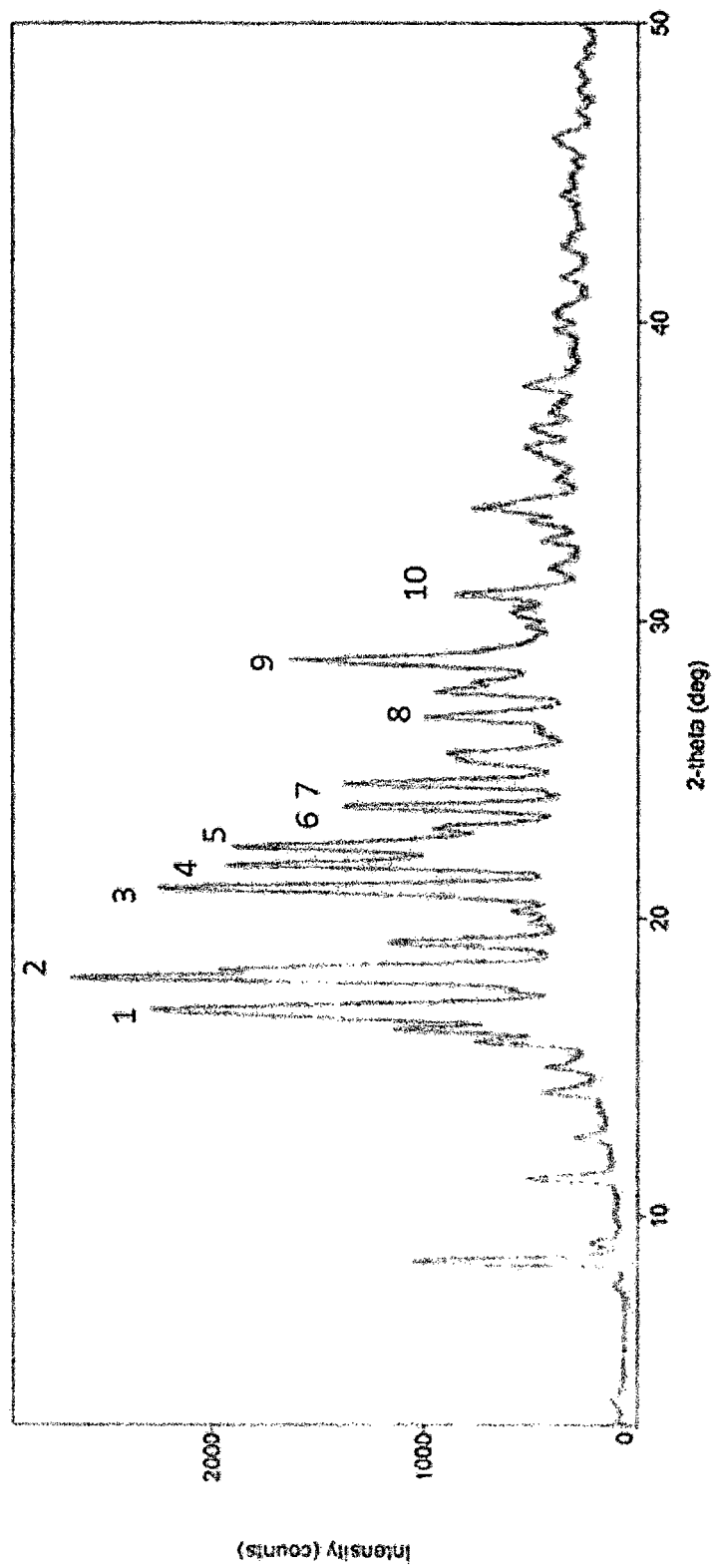

[Fig. 6]
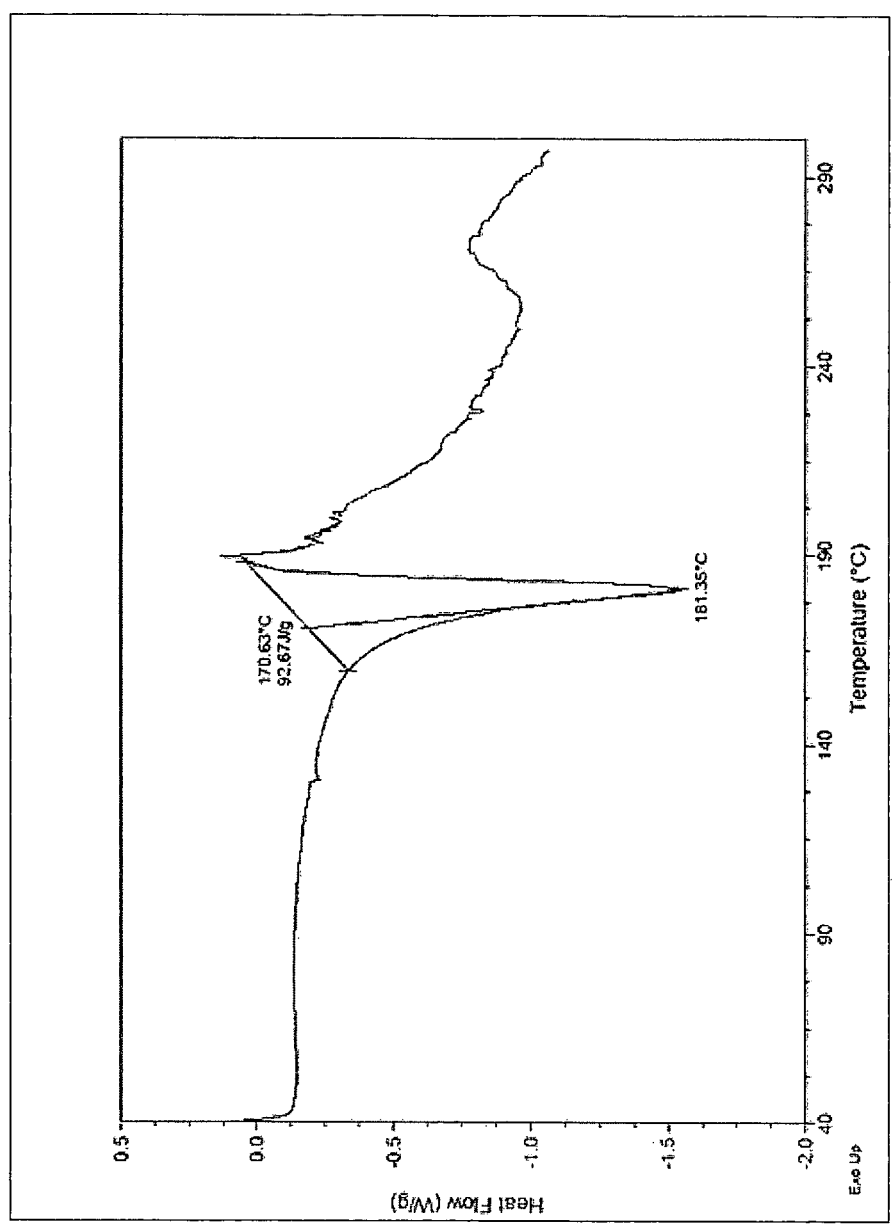

N-PHOSPHONOXYMETHYL PRODRUGS OF HYDROXYALKYL THIADIAZOLE DERIVATIVES

The present invention provides N-phosphonoxymethyl prodrugs of hydroxyalkyl thiadiazole compounds, or pharmaceutically acceptable salts thereof, having excellent antibacterial activity, excellent solubility, especially for an aqueous preparation, and also being excellent in terms of safety. Furthermore, the present invention provides pharmaceutical compositions comprising N-phosphonoxymethyl prodrugs of hydroxyalkyl thiadiazole compounds, polymorphs, or pharmaceutically acceptable salts thereof as pharmaceutically active ingredients. Particularly, the present invention provides N-phosphonoxymethyl prodrugs of hydroxyalkyl thiadiazole compounds, polymorphic forms, or pharmaceutically acceptable salts thereof useful for treating and/or preventing infectious diseases.

BACKGROUND ART

There are several Gram-positive species that cause diseases in humans. The most common organisms include *Staphylococcus, Streptococcus, Enterococcus, Clostridium, Bacillus, Corynebacterium*, and *Listeria* species. Infections with common Gram-positive organisms have become more problematic to treat because of the growing trend of antibiotics drug-resistance.

Examples of such difficult-to-treat resistant bacteria include methicillin-resistant *Staphylococcus aureus* (MRSA), penicillin-resistant *Streptococcus pneumoniae* (PRSP), and vancomycin-resistant *Enterococcus* (VRE).

*Staphylococcus aureus* can cause a range of illnesses such as pimples, impetigo, boils, cellulitis folliculitis, furuncles, carbuncles, scalded skin syndrome, pneumonia, meningitis, osteomyelitis, endocarditis, toxic shock syndrome and sepsis. *S. aureus* is one of the most common causes of hospital-acquired infections. *Streptococcus pneumoniae* can cause many types of infections such as community acquired pneumonia, bronchitis, rhinitis, acute sinusitis, otitis media, conjunctivitis, meningitis, bacteremia, sepsis, osteomyelitis, septic arthritis, endocarditis, peritonitis, pericarditis, cellulitis, and brain abscess. *Enterococcus* can cause urinary tract infections, bacteremia, endocarditis, diverticulitis, and meningitis.

*Clostridium difficile* infection (CDI) is another problematic Gram-positive bacterial infection. CDI-related death has increased due to the spread of a hyper virulent NAP1/027 strain. Current treatments lead to more than 23% recurrence and have limitations against this virulent strain.

*Haemophilus influenzae*, a Gram negative bacteria, can cause many kinds of infections including, but not limited to, ear infections, bacteremia, community-acquired respiratory infections, pneumonia and acute bacterial meningitis.

Treatment of bacterial infectious diseases is becoming more difficult and expensive due to developing resistance to existing antibiotics, spreading hypervirulent strains, and non-availability of more efficatious novel antibacterial agents.

In view of the above facts, the inventors of the present invention have realized that there should be a novel class of antibacterial agent having novel mechanism of action. After exhaustive research, the inventors of the present invention have discovered novel compounds targeting the DNA gyrase GyrB subunit and/or topoisomerase IV ParE subunit, and hence are ready to meet the requirements of millions of patients worldwide.

In developing antibiotics having a novel mechanism of action, synthetic inhibitors targeting the DNA gyrase GyrB subunit are known in the art. For example, WO 2005/026149 (PTL 1), WO 2006/087543 (PTL 2), WO 2006/087544 (PTL 3), WO 2006/087548 (PTL 4), WO 2006/092599 (PTL 5), WO 2006/092608 (PTL 6), WO 2008/152418 (PTL 7), WO 2008/020222 (PTL 8), WO 2008/020227 (PTL 9), WO 2008/020229 (PTL 10), WO 2010/013222 (PTL 11), WO 2010/067123 (PTL 12), and WO 2010/067125 (PTL 13) describe pyrrole derivatives having antibacterial activity. WO 2007/071965 (PTL 14) describes bicyclic heteroaromatic compounds. WO 2014/057415 (PTL 15) describes quinoline based compounds. These compounds had the problems of insufficient activity, low water solubility and toxicity. In addition, none of the cited references disclosed imidazole derivatives.

WO 2009/084614(PTL 16), incorporated herein by reference in its entirety, describes imidazole derivatives. The compounds disclosed in WO 2009/084614 have good properties, for example, sufficient in vitro antibacterial activity and no cytotoxicity. However, Compound No. 150 having a thiadiazole substituent had a problem of not being efficacious in animal infection models, hence not suitable for use in human.

[Chem. 1]

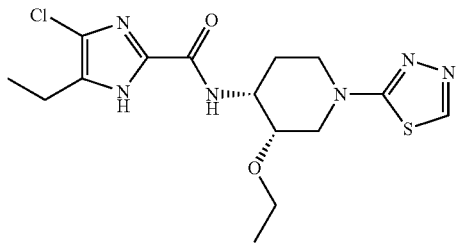

Compound No. 150

(WO 2009/084614)

On the contrary, the hydroxyalkyl thiadiazol derivative thereof, in which the thiadiazole moiety of said compound is modified to be substituted with hydroxyalkyl substitutents have been revealed to have sufficient solubility for oral absorption. The structure of said hydroxyalkyl thiadiazole derivative is represented by the following general formula (1'):

[Chem. 2]

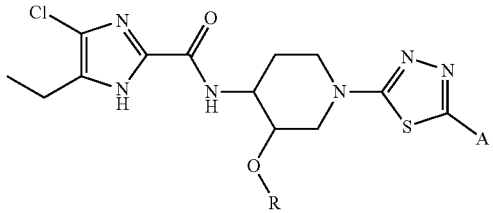

(1')

wherein R represents $(C_1-C_3)$ alkyl, and

A represents the following formulae:

[Chem. 3]

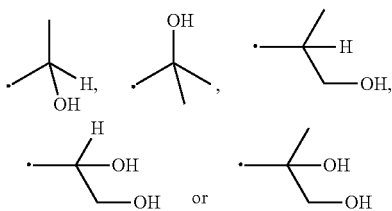

provided that, in the general formula (1'), for example, tautomers with a hydrogen at different positions of the imidazole ring are included.

In more detail, the following compounds are included therein as more preferable compounds:

[Chem. 4]

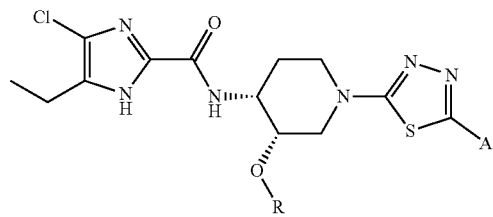

wherein R represents ($C_1$-$C_3$) alkyl, and
A represents the following formulae:

[Chem. 5]

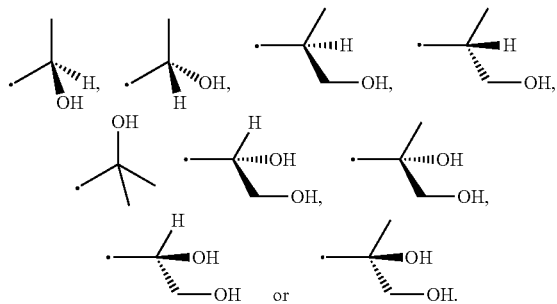

Surprisingly, said hydroxyalkyl thiadiazole compounds of the general formula (1') showed not only sufficient in vitro antibacterial activity, no cytotoxicity, good water solubility for oral absorption, but also remarkably good efficacy and safety, and hence are suitable for use in humans. The present invention describes N-phosphonoxymethyl prodrugs of the hydroxyalkyl thiadiazole compound of the general formula (1'), preferably for oral or intravenous use.

Thus, the present invention provides great hope for a new antibiotic to meet the challenges of a serious global health concern due to problematic bacteria thereof causing bacterial infections, for example, but not limited to, community-acquired respiratory infections, hospital-acquired infections, urinary tract infections, and *Clostridium difficile* infections.

CITATION LIST

Patent Literature

PTL 1: WO 2005/026149
PTL 2: WO 2006/087543
PTL 3: WO 2006/087544
PTL 4: WO 2006/087548
PTL 5: WO 2006/092599
PTL 6: WO 2006/092608
PTL 7: WO 2008/152418
PTL 8: WO 2008/020222
PTL 9: WO 2008/020227
PTL 10: WO 2008/020229
PTL 11: WO 2010/013222
PTL 12: WO 2010/067123
PTL 13: WO 2010/067125
PTL 14: WO 2007/071965
PTL 15: WO 2014/057415
PTL 16: WO 2009/084614

SUMMARY OF INVENTION

Technical Problem

As realized by the inventors of the present invention, there is a need for a new antibiotic having a novel mechanism of action, which exhibits strong antibacterial activity not only against sensitive bacteria, but also against resistant bacteria thereof, and at the same time possesses excellent solubility for intravenous use.

Solution to Problem

The present invention provides N-phosphonoxymethyl prodrugs of hydroxyalkyl thiadiazole compound [referred to herein a compound of general formula (I)], or a pharmaceutically acceptable salt thereof, having excellent antibacterial activity, and also being excellent in terms of safety. The parent compound (biologically active form) of general formula (I) or a pharmaceutically acceptable salt thereof inhibits its DNA gyrase GyrB subunit and/or topoisomerase IV ParE subunit. In one aspect, the present invention provides:

[1] A compound represented by general formula (I), or a regioisomer thereof, or a pharmaceutically acceptable salt thereof:

[Chem. 6]

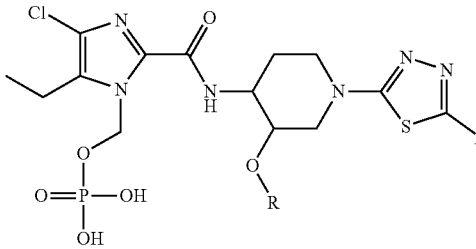

(I)

wherein R represents ($C_1$-$C_3$) alkyl, and

A represents the following formulae:

[Chem. 7]

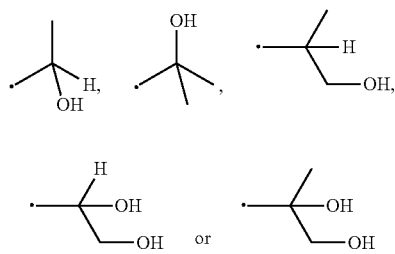

provided that, in the general formula (I), the N-phosphonoxymethyl group present at different positions of the imidazole ring are included as regioisomers.

[2] The compound, or a regioisomer thereof, or a pharmaceutically acceptable salt thereof according to [1], wherein the compound of general formula (I) has the following structures:

[Chem. 8]

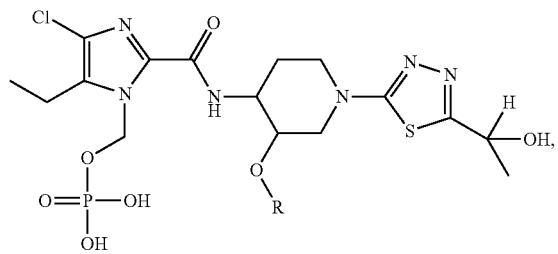
(Ia)

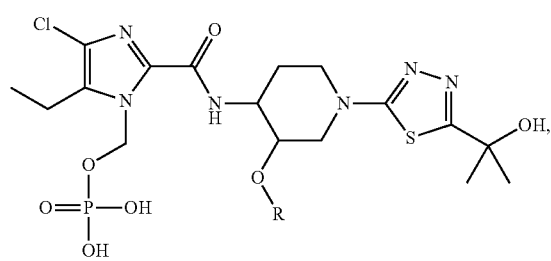
(Ib)

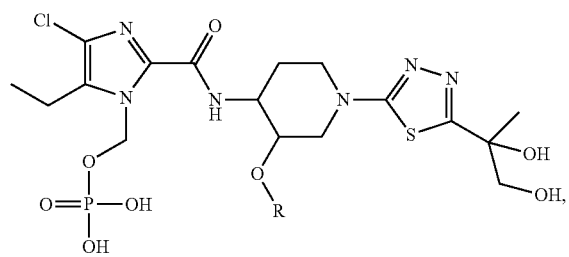
(Ic)

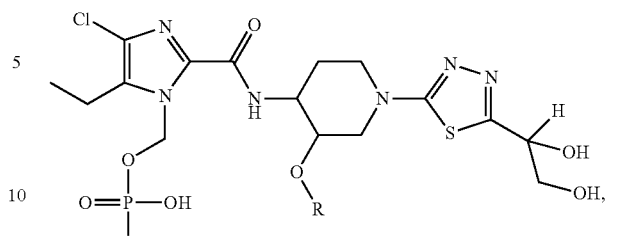
(Id)

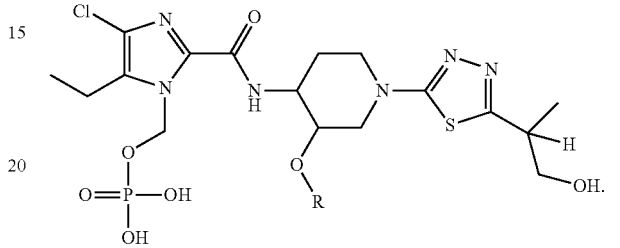
(Ie)

[3] The compound, or a regioisomer thereof, or a pharmaceutically acceptable salt thereof according to [1], wherein the compound of general formula (I) has the following structure:

[Chem. 9]

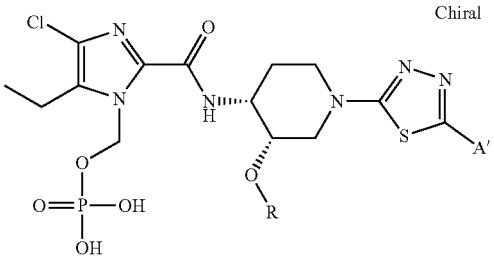

wherein R represents ($C_1$-$C_3$) alkyl, and A' represents the following formulae:

[Chem. 10]

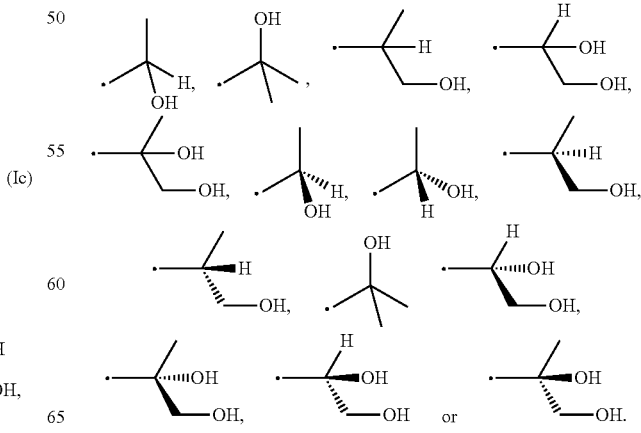

[4] The compound, or a regioisomer thereof, or a pharmaceutically acceptable salt thereof according to [3], wherein A' represents the following formulae:

[Chem. 11]

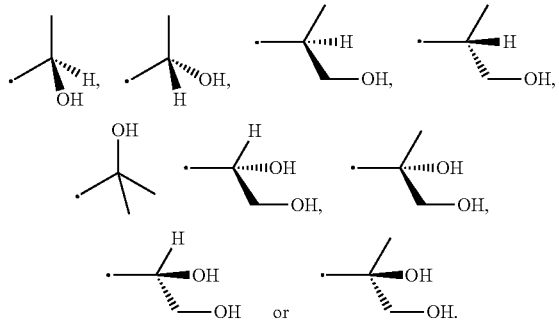

[5] The compound, or a regioisomer thereof, or a pharmaceutically acceptable salt thereof according to [1] or [3], wherein the compound of general formula (I) has the following structure:

[Chem. 12]

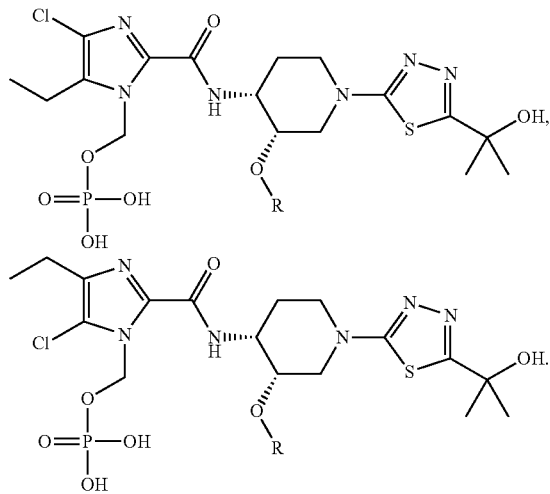

[6] The compound, or a regioisomer thereof, or a pharmaceutically acceptable salt thereof according to [1] or [4], wherein the compound of general formula (I) has the following structures:

[Chem. 13]

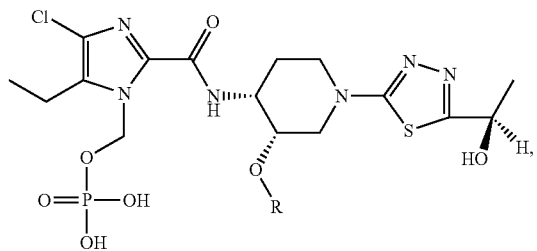

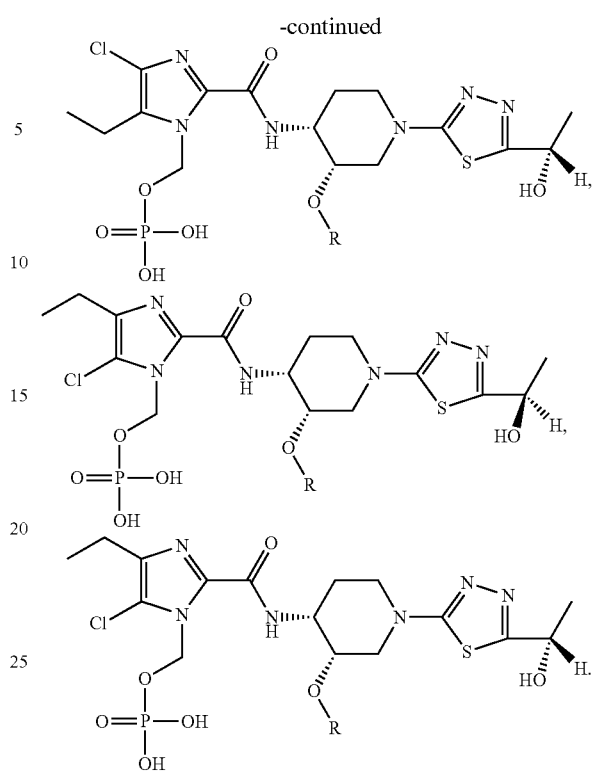

[7] The compound, or a regioisomer thereof, or a pharmaceutically acceptable salt thereof according to [1] or [4], wherein the compound of general formula (I) has the following structures:

[Chem. 14]

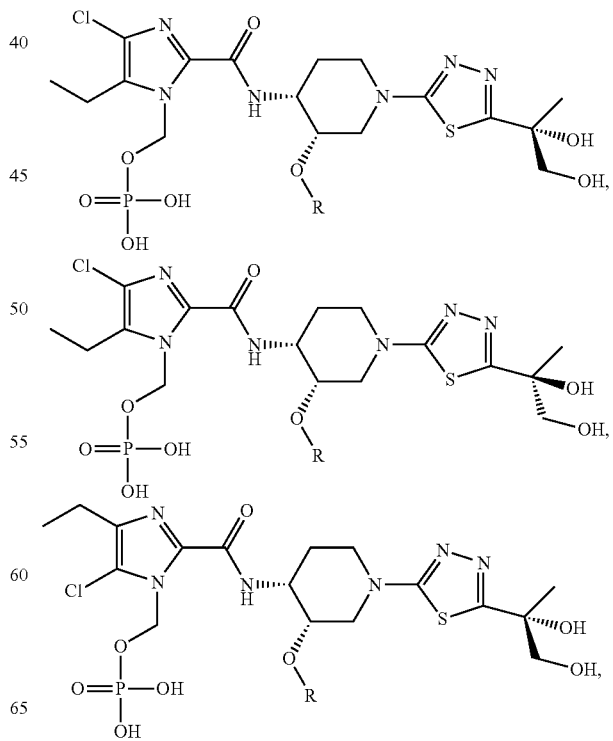

-continued

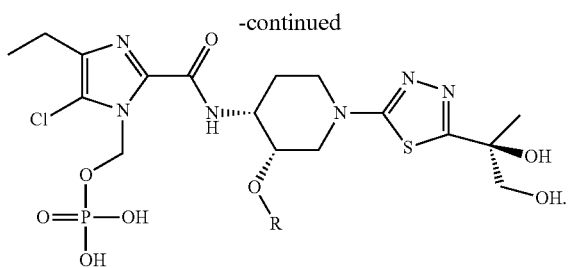

[8] The compound, or a regioisomer thereof, or a pharmaceutically acceptable salt thereof according to [1] or [4], wherein the compound of general formula (I) has the following structures:

[Chem. 15]

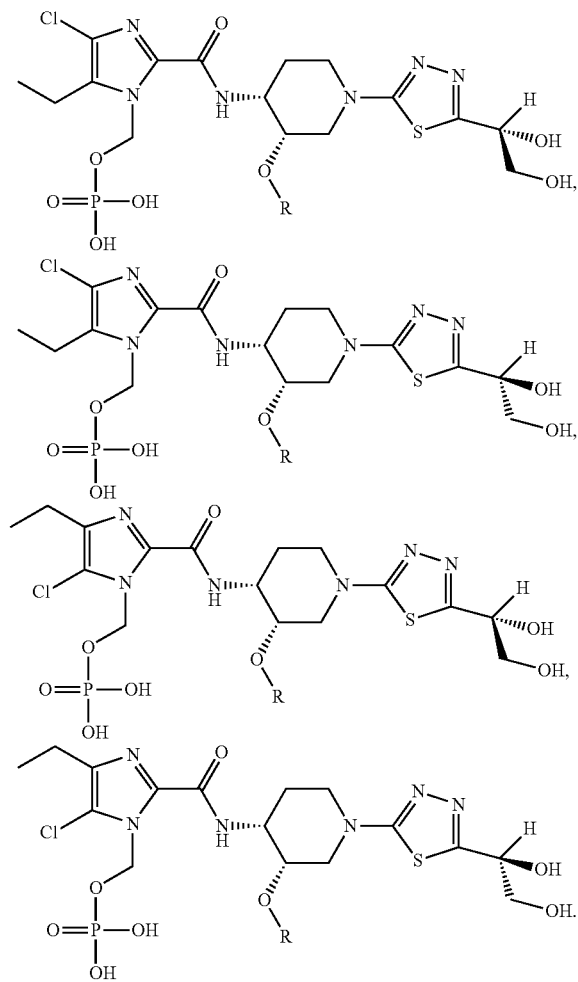

[9] The compound, or a regioisomer thereof, or a pharmaceutically acceptable salt thereof according to any one of [1] to [8], wherein R represents methyl.

[10] The compound, or a regioisomer thereof, or a pharmaceutically acceptable salt thereof according to any one of [1] to [8], wherein R represents ethyl.

[11] The compound or a pharmaceutically acceptable salt thereof according to any one of [1] to [10], wherein the compound is selected from:

[4-Chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 1),

[5-Chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 2), (4-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate (Compound No. 3), (5-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl)methyl dihydrogen phosphate (Compound No. 4), (4-Chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 5), (5-Chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 6), (4-Chloro-2-{[(3S,4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl dihydrogen phosphate (Compound 7), (5-Chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate (Compound 8),

[4-Chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl dihydrogen phosphate (Compound 9), (5-Chloro-2-{[(3S,4R)-1-{5-[(1S)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate (Compound No. 10), and pharmaceutically acceptable salts thereof.

[12] The crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate, characterized by a powder x-ray diffraction (XRD) spectrum substantially in accordance with the pattern shown in FIG. 3.

[13] The crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate, characterized by differential scanning calorimetry (DSC) substantially in accordance with the curve shown in FIG. 4.

[14] The crystalline form of diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate, characterized by a powder x-ray diffraction (XRD) spectrum substantially in accordance with the pattern shown in FIG. 5.

[15] The crystalline form of diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate, characterized by differential scanning calorimetry (DSC) substantially in accordance with the curve shown in FIG. 6.

[16] A pharmaceutical composition comprising a therapeutically effective amount of a compound, or a regioisomer thereof, or a pharmaceutically acceptable salt thereof according to any one of [1] to [15] as its active ingredient.

[17] A pharmaceutical composition according to [16], wherein said pharmaceutical composition is to be administered to treat or prevent bacterial infectious diseases.

[18] The pharmaceutical composition according to [17], wherein said bacterial infectious disease is caused by Gram-positive bacteria selected from genus *Staphylococcus, Streptococcus, Enterococcus, Clostridium, Bacillus, Corynebacterium*, and *Listeria* species.

[19] The pharmaceutical composition according to [17], wherein said bacterial infectious disease is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[20] The pharmaceutical composition according to [17], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[21] The pharmaceutical composition according to [17], wherein said bacterial infectious diseases is selected from community-acquired respiratory infections, hospital-acquired infections or *Clostridium difficile* infections.

[22] A method for treating bacterial infectious disease in a patient comprising administering to said patient a therapeutically effective amount of a compound, or a regioisomer thereof, or a pharmaceutical salt thereof according to any one of [1] to [15].

[23] The method according to [22], wherein said bacterial infectious disease is caused by Gram-positive bacteria selected from genus *Staphylococcus, Streptococcus, Enterococcus, Clostridium, Bacillus, Corynebacterium*, and *Listeria* species.

[24] The method according to [22], wherein said bacterial infectious disease is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[25] The method according to [22], wherein said bacterial infectious disease is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[26] The method according to [22], wherein said bacterial infectious disease is selected from community-acquired respiratory infections, hospital-acquired infections or *Clostridium difficile* infections.

[27] A compound, or a regioisomer thereof, or a pharmaceutically acceptable salt thereof according to any one of [1] to [15] for use as a pharmaceutical agent for treating bacterial infectious diseases.

[28] The compound, regioisomer, or pharmaceutically acceptable salt for the use according to [27], wherein said bacterial infectious disease is caused by Gram-positive bacteria selected from genus *Staphylococcus, Streptococcus, Enterococcus, Clostridium, Bacillus, Corynebacterium*, and *Listeria* species.

[29] The compound, regioisomer, or pharmaceutically acceptable salt for the use according to [27], wherein said bacterial infectious disease is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[30] The compound, regioisomer, or pharmaceutically acceptable salt for the use according to [27], wherein said bacterial infectious disease is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[31] The compound, regioisomer, or pharmaceutically acceptable salt for the use according to [27], wherein said bacterial infectious disease is selected from community-acquired respiratory infections, hospital-acquired infections or *Clostridium difficile* infections.

[32] Use of a compound, or a regioisomer thereof, a polymorphic form, or a pharmaceutically acceptable salt thereof according to any one of [1] to [15] for the production of a therapeutic agent for bacterial infections.

[33] The use according to [32], wherein said bacterial infections are caused by Gram-positive bacteria selected from genus *Staphylococcus, Streptococcus, Enterococcus, Clostridium, Bacillus, Corynebacterium*, and *Listeria* species.

[34] The use according to [32], wherein said bacterial infections are caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[35] The use according to any one of [32] to [34], wherein said bacterial infectious disease is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[36] The use according to [35], wherein said bacterial infectious disease is selected from community-acquired respiratory infections, hospital-acquired infections or *Clostridium difficile* infections.

BRIEF DESCRIPTION OF DRAWINGS

FIG. 1 Conversion efficiency of Compound No. 1 in Rat, Dog and Monkey.

FIG. 2 Conversion efficiency of Compound No. 2 in Rat, Dog and Monkey.

FIG. 3 The powder x-ray powder diffraction (XRD) pattern for crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate.

FIG. 4 The differential scanning calorimetry (DSC) curve for crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate.

FIG. 5 The powder x-ray powder diffraction (XRD) pattern for crystalline form of diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate.

FIG. 6 The differential scanning calorimetry (DSC) curve for crystalline form of diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate.

The aforementioned aspects and embodiments, and other aspects, objects, features and advantages of the present invention will be apparent from the following detailed description and the appended claims thereof.

DESCRIPTION OF EMBODIMENTS

As used herein the following definitions apply unless clearly indicated otherwise.

It should be understood that unless expressly stated to the contrary, "a compound of general formula (I)" refers to and includes any and all compounds described by formula (I), its embodiments, as well as subgenuses, inclusive of all salts, stereoisomers thereof. It should also be noted that the singular forms "a" "an" and "the" include plural reference unless the context clearly dictates otherwise.

In one aspect of the present invention, there is provided a compound of general formula (I), a stereoisomer, a regioisomer thereof, or a pharmaceutically acceptable salt thereof.

[Chem. 16]

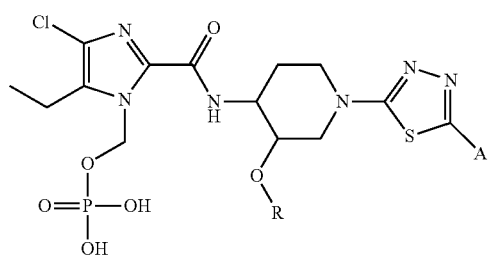

(I)

wherein R, A and A' are as defined above.

The compound of general formula (I) may have regioisomers with the phosphonoxymethyl group present at different positions of the imidazole ring. All such regioisomer are within the scope of the present invention, for example:

[Chem. 17]

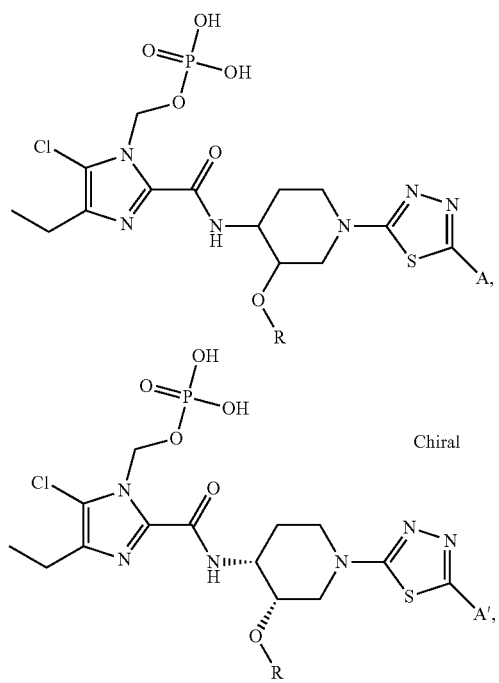

The compound of general formula (I) includes the following structures:

[Chem. 18]

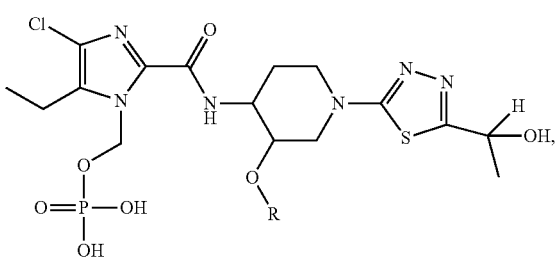
(Ia)

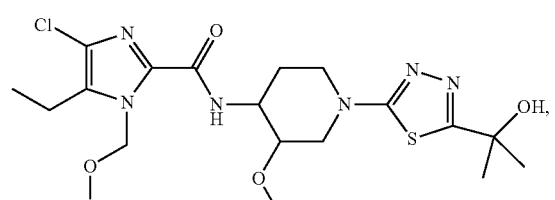
(Ib)

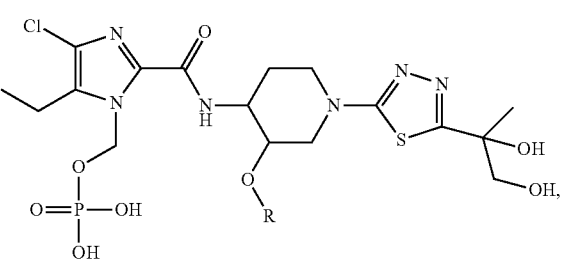
(Ic)

-continued

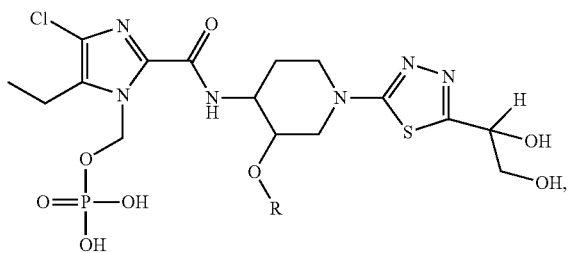

(Id)

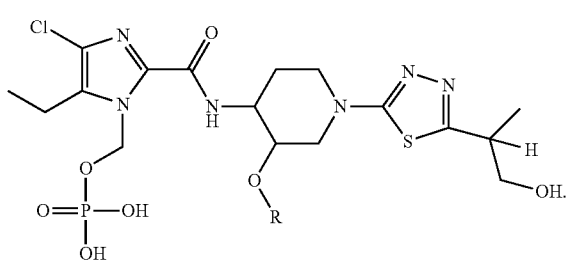

(Ie)

In a preferred embodiment, there is provided a compound of formula (Ia), or a regioisomer thereof, or a stereoisomer, or a pharmaceutically acceptable salt thereof:

[Chem. 19]

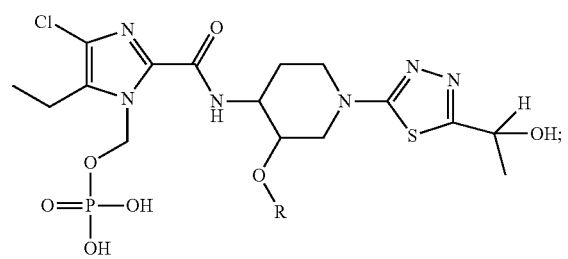

(Ia)

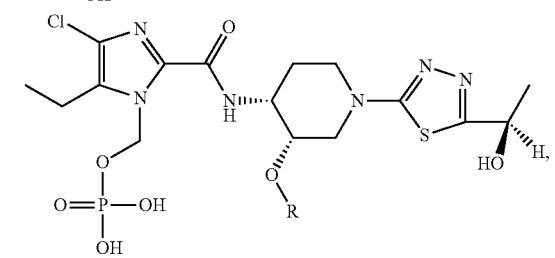

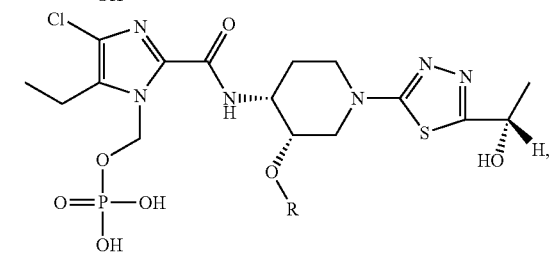

wherein R represents ($C_1$-$C_3$) alkyl, and regioisomers with the phosphonoxymethyl group present at different positions of the imidazole ring are included.

In another preferred embodiment, there is provided a compound of formula (Ib), or a regioisomer thereof, or a stereoisomer, or a pharmaceutically acceptable salt thereof:

[Chem. 20]

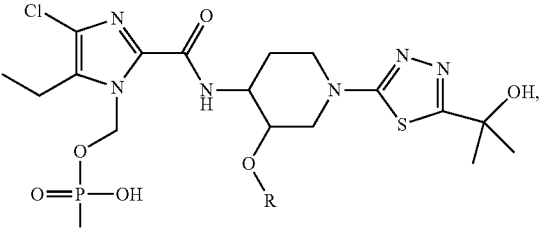

(Ib)

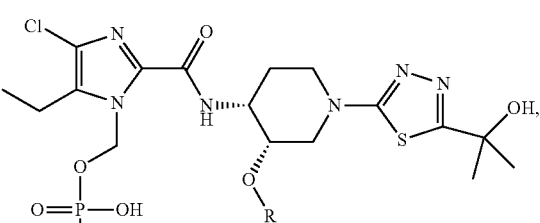

wherein R represents ($C_1$-$C_3$) alkyl, and regioisomers with the phosphonoxymethyl group present at different positions of the imidazole ring are included.

In another preferred embodiment, there is provided a compound of formula (Ic), or a regioisomer, a stereoisomer, or a pharmaceutically acceptable salt thereof:

[Chem. 21]

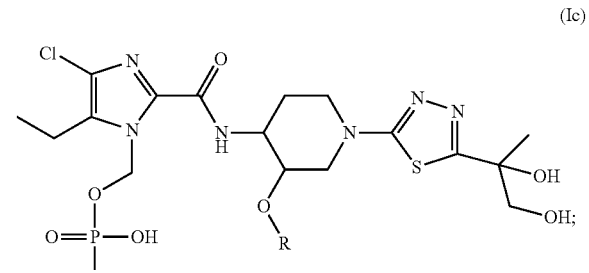

(Ic)

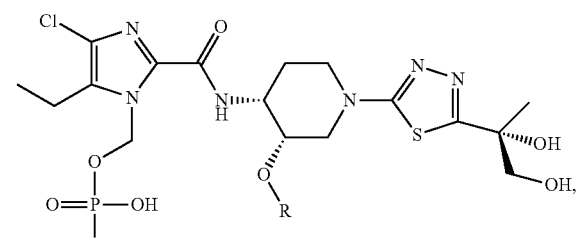

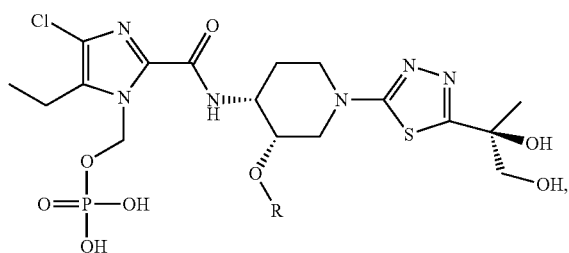

wherein R represents (C₁-C₃) alkyl; and regioisomers with phosphonoxymethyl group present at different positions of the imidazole ring are included.

In another preferred embodiment, there is provided a compound of formula (Id), a regioisomer, a stereoisomer, or a pharmaceutically acceptable salt thereof:

[Chem. 22]

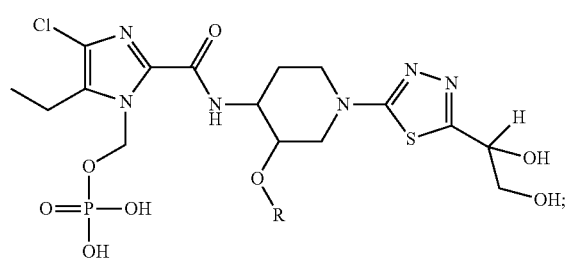

(Id)

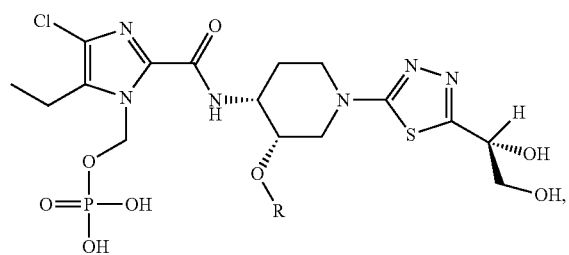

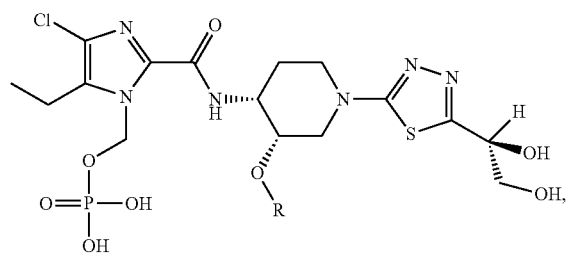

wherein R represents (C₁-C₃) alkyl; and regioisomer with phosphonoxymethyl group present at different positions of the imidazole ring are included.

In another preferred embodiment, there is provided a compound of formula (Ie), a stereoisomer, or a pharmaceutically acceptable salt thereof:

[Chem. 23]

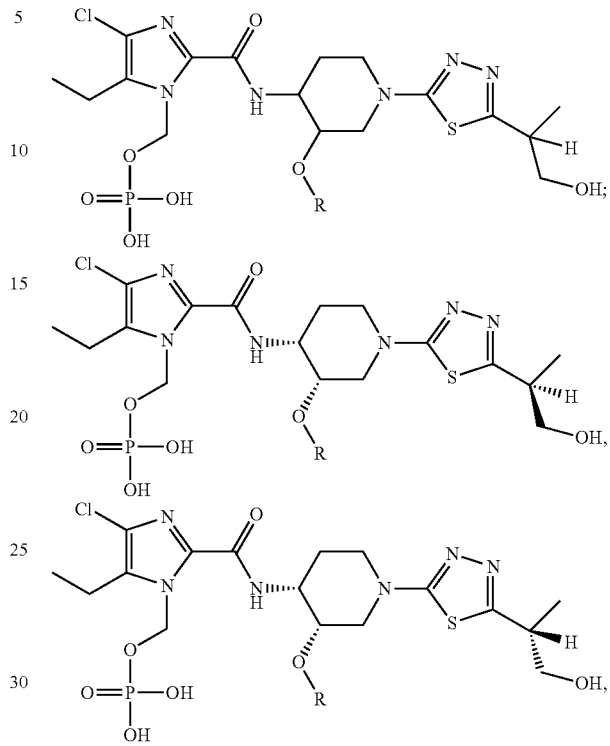

(Ie)

wherein R represents (C₁-C₃) alkyl; and regioisomers with phosphonoxymethyl group present at different positions of the imidazole ring are included.

The present invention intends to include within the scope of the first aspect, various preferred embodiments for perfecting the invention as pointed out in the background section.

For example, in one embodiment, there is provided a compound of formula (Ia), a regioisomer, a stereoisomer, a pharmaceutically acceptable salt thereof, wherein R represents methyl or ethyl.

In another embodiment, there is provided a compound of formula (Ib), a regioisomer, a stereoisomer, a pharmaceutically acceptable salt thereof, wherein R represents methyl or ethyl.

In another embodiment, there is provided a compound of formula (Ic), a regioisomer, a stereoisomer, a pharmaceutically acceptable salt thereof, wherein R represents methyl or ethyl.

In another embodiment, there is provided a compound of formula (Id), a regioisomer, a stereoisomer, a pharmaceutically acceptable salt thereof, wherein R represents methyl or ethyl.

In another embodiment, there is provided a compound of formula (Ie), a regioisomer, a stereoisomer, a pharmaceutically acceptable salt thereof, wherein R represents methyl or ethyl.

According to a particular embodiment of the present invention, there is provided a specific compound of formula (I), which is selected from:
[4-Chloro-5-ethyl-2-({(3S,4R)-1-[5-(2-hydroxypropan-2-yl)-1,3,4-thiadiazol-2-yl]-3-methoxypiperidin-4- yl}carbamoyl)-1H-imidazol-1-yl]methyl dihydrogen phosphate (Compound No. 1),

[5-Chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 2), (4-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate (Compound No. 3), (5-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl)methyl dihydrogen phosphate (Compound No. 4), (4-Chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 5), (5-Chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 6), (4-Chloro-2-{[(3S,4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl dihydrogen phosphate (Compound 7), (5-Chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate (Compound 8),

[4-Chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl dihydrogen phosphate (Compound 9), (5-Chloro-2-{[(3S,4R)-1-{5-[(1S)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate (Compound No. 10), and pharmaceutically acceptable salts thereof.

In a preferred embodiment, there is provided a crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl] methyl dihydrogen phosphate, designated as Form I and characterized by a powder x-ray diffraction (XRD) spectrum substantially in accordance with the pattern shown in FIG. 3.

Form I is further characterized by differential scanning calorimetry (DSC) substantially in accordance with the curve shown in FIG. 4.

In a preferred embodiment, there is provided a crystalline form of diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl] methyl dihydrogen phosphate, designated as Form II and characterized by a powder x-ray diffraction (XRD) spectrum substantially in accordance with the pattern shown in FIG. 5.

Form II is further characterized by differential scanning calorimetry (DSC) substantially in accordance with the curve shown in FIG. 6.

In another preferred embodiment, Form I and Form II are further characterized by prominent XRD peaks as given in Table 1.

TABLE 1

XRD (CuK, λ = 1.54 Å, scan rate = 20°/minute)

| | Prominent Peaks (Form I) | | | | Prominent Peaks (Form II) | | |
|---|---|---|---|---|---|---|---|
| Peak | 2θ | d | Relative Intensity | Peak | 2θ | d | Relative Intensity |
| 1 | 4.38 | 20.12 | 100 | 1 | 16.24 | 5.45 | 17.89 |
| 2 | 12.45 | 7.10 | 14.51 | 2 | 16.90 | 5.24 | 100 |
| 3 | 13.93 | 6.34 | 22.53 | 3 | 21.02 | 4.22 | 60.73 |
| 4 | 14.89 | 5.94 | 17.26 | 4 | 21.75 | 4.08 | 43.27 |
| 5 | 16.19 | 5.46 | 29.25 | 5 | 22.38 | 3.96 | 51.95 |
| 6 | 18.49 | 4.79 | 17.30 | 6 | 23.73 | 3.74 | 22.75 |
| 7 | 19.74 | 4.49 | 31.75 | 7 | 24.51 | 3.62 | 23.07 |
| 8 | 20.95 | 4.23 | 7.08 | 8 | 26.74 | 3.33 | 14.65 |
| 9 | 23.94 | 3.71 | 28.57 | 9 | 28.62 | 3.11 | 47.08 |
| 10 | 26.44 | 3.36 | 10.91 | 10 | 30.87 | 2.89 | 12.58 |

In the invention, it should be understood that a compound of general formula (I) or a salt thereof may sometimes indicate the regioisomeric phenomenon, and the formulae and figures in the present specification can only represent one of the possible regioisomeric forms. It should be understood that the present invention encompasses any of the regioisomeric forms which inhibits DNA gyrase GyrB subunit and/or topoisomerase IV ParE subunit and is not limited to only one of the regioisomeric forms used in the formulae or figures. It should be understood that the formulae and figures in the present specification can only represent one of the possible regioisomeric forms and the present specification encompasses not only the forms which can be shown in the formulae but also all possible regioisomeric forms of the compounds shown in the formulae. The same is also applicable to the compound names.

The compound of the present invention represented by general formula (I) or a pharmaceutically acceptable salt thereof, when left in the air or recrystallized, may absorb water to associate with adsorbed water or to form a hydrate. Such water-containing compounds and salts are also encompassed by the present invention.

The compound of the present invention represented by general formula (I) has an acidic centre hence a "pharmaceutically acceptable salt thereof" can be formed by reacting the compound with a base.

The term "pharmaceutically acceptable" as used herein refers to a compound of formula (I) or pharmaceutical composition thereof suitable for administration to animals, preferably humans as approved by a regulatory agency such as European Medicine Agency (EMEA), US Food and Drug Administration (FDA) or any other National Regulatory Agency.

Preferred examples of a salt of the present invention includes, but are not limited to, alkali or alkaline earth metal salt such as sodium, lithium, potassium, calcium, magnesium, and the like, as well as non-toxic ammonium, quaternary ammonium and amine salt such as ammonium, tetramethylammonium, tetraethylammonium, lysine, arginine, benzathine, choline, tromethamine, diolamine, ethanolamine, tert-butylamine, glycine, meglumine, olamine, and the like.

The compound represented by general formula (I), or pharmaceutically acceptable salt thereof, has an asymmetric carbon atom in the molecule, hence stereoisomers with an R or S configuration are included. Each of these stereoisomers and all mixtures of the stereoisomers at arbitrary ratios are also encompassed by the present invention. Such stereoisomers can be prepared, for example, by synthesizing the compound (I) using appropriate resolving agents or by optically resolving the synthesized compound (I) by a usual optical resolution or separation method or diastereoselective synthesis as desired.

The compound of the present invention represented by general formula (I) or a pharmaceutically acceptable salt thereof includes optical isomers. Each of these optical isomers and all mixtures of these optical isomers are also encompassed by the present invention.

The compound of the present invention represented by general formula (I) or a pharmaceutically acceptable salt thereof include stereoisomers based on the type of substitution at 3 or 4 position of piperidine ring. For example, in general formula (I), the cis-isomer is the preferred one as shown below:

[Chem. 24]

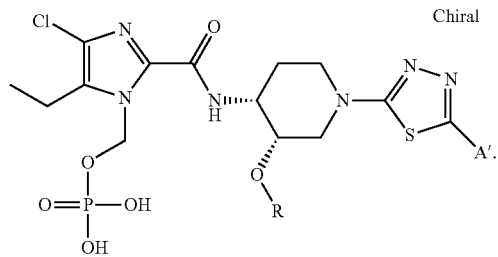

The present invention includes as preferable isomers, but is not limited to,

[Chem. 25]

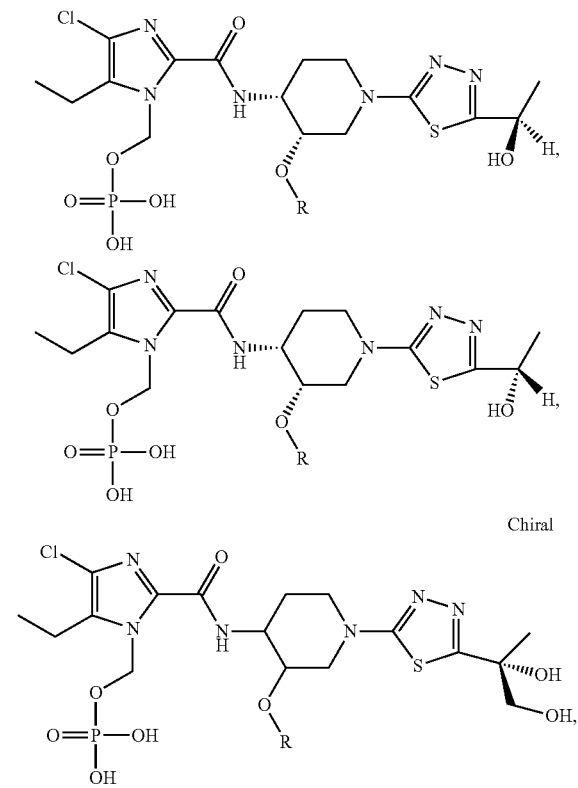

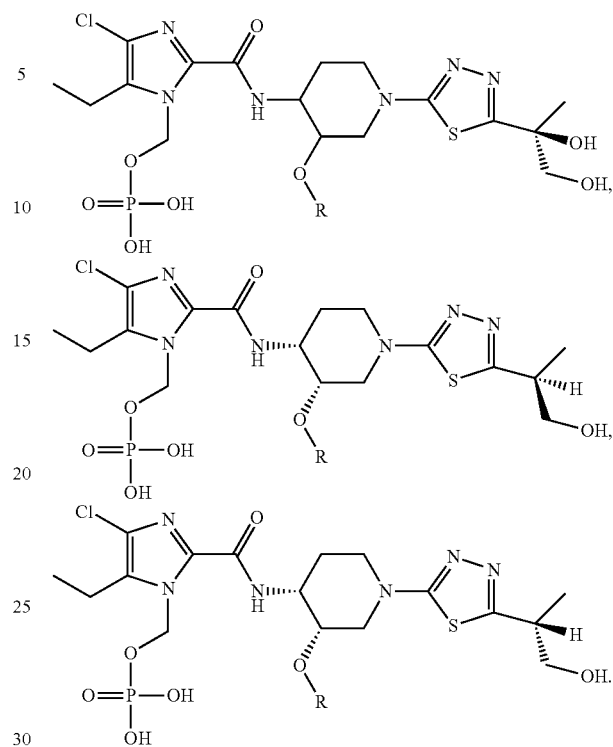

Some compounds as shown above showed polymorphic characters, hence it should be understood that the present invention encompasses polymorphic forms in addition to every racemic, optically active, stereoisomeric form or mixtures thereof, which inhibits DNA gyrase GyrB subunit and/or topoisomerase IV ParE subunit.

The optically active form can be prepared by methods known in the art, for example, i) resolution of the racemic form by recrystallization techniques, ii) synthesis from optically-active starting materials, iii) chiral synthesis, iv) enzymatic resolutions, v) bioconversion, or vi) chromatographic separation using a chiral stationary phase. Similarly, any method known in the art for measuring inhibitory effect for DNA gyrase GyrB subunit and/or topoisomerase IV ParE subunit can be employed including the method described hereinafter.

Next, a pharmaceutical composition comprising a compound of general formula (I), a stereoisomer, a polymorphic form, or pharmaceutically acceptable salt thereof is provided.

The compound of the present invention alone or in a form of pharmaceutical composition may be typically used to prevent or treat bacterial infections in animals including humans. Thus, for treating and preventing, a suitable dosage form may be required. The suitable dosage forms will depend upon the use or route of administration. Techniques and formulations generally may be found in The Science and Practice of Pharmacy, 21$^{st}$ edition, Lippincott, Willams and Wilkins, Philadelphia, Pa., 2005 (incorporated herein by reference).

Thus, in another aspect, the present invention provides a pharmaceutical composition for use in treating bacterial infections in a warm-blooded animal such as human, wherein the composition comprises a compound of formula (I), a stereoisomer, a polymorphic form, or a pharmaceutically acceptable salt thereof, together with a pharmaceutically acceptable excipient or carrier.

The pharmaceutical composition of the present invention may be in a form suitable for oral use (e.g., tablets, lozenges, hard or soft capsules, aqueous or oily suspensions, emulsions, dispersible powders or granules, syrups and elixirs), topical use (e.g., creams, ointments, gels, and aqueous or oily solutions or suspensions), administration by an inhalation method (e.g., finely grained powders and liquid aerosols), administration by an aeration method (e.g., pulverized powders), or parenteral administration (e.g., sterile aqueous or oily solutions for intravenous, subcutaneous, or intramuscular administration and suppositories for rectal administration).

The pharmaceutical composition of the present invention can be obtained by conventional approaches using conventional pharmaceutical excipients well known in the art. Thus, the compositions intended for oral use may contain, for example, one or more coloring agent(s), sweetener(s), corrigent(s), and/or preservative(s).

Examples of pharmaceutically acceptable excipients suitable for tablet preparation include, but are not limited to, inert diluents (e.g., lactose, sodium carbonate, calcium phosphate and calcium carbonate); granulating agents and disintegrants (e.g., corn starch and alginic acid); binders (e.g., starch); lubricants (e.g., magnesium stearate, stearic acid, and talc); preservatives (e.g., ethyl p-hydroxybenzoate and propyl p-hydroxybenzoate); and antioxidants (e.g., ascorbic acid).

The tablets so prepared may be uncoated or coated for altering their disintegration, and subsequent enteral absorption of the active ingredient, or for improving their stability and/or appearance. In both cases, conventional coating agents and approaches well known in the art can be employed.

The pharmaceutical compositions intended for oral use may be in a form of hard gelatin capsule. In this case, the active ingredient is mixed with an inert solid diluent, for example, calcium carbonate, calcium phosphate, or kaolin. Alternatively, for use as a soft gelatin capsule, the active ingredient is mixed with water or oil, for example, peanut oil, liquid paraffin, or olive oil.

The aqueous solutions generally comprise an active ingredient in a pulverized form, together with one or more suspending agent(s) (e.g., sodium carboxymethylcellulose, methylcellulose, hydroxypropylmethylcellulose, sodium alginate, polyvinylpyrrolidone, tragacanth gum, and gum arabic); and dispersant(s) or wetting agent(s) (e.g., lecithin, condensation products of alkylene oxides and fatty acids such as polyoxyethylene stearate), condensation products of ethylene oxide and long-chain aliphatic alcohols (e.g., heptadecaethylene oxycetanol), condensation products of ethylene oxide and partial esters derived from fatty acids and hexitols (e.g., polyoxyethylene sorbitol monooleate), condensation products of ethylene oxide and long-chain aliphatic alcohols (e.g., heptadecaethylene oxycetanol), condensation products of ethylene oxide and partial esters derived from fatty acids and hexitols (e.g., polyoxyethylene sorbitol monooleate), and condensation products of ethylene oxide and partial esters derived from fatty acids and hexitol anhydrides (e.g., polyethylene sorbitan monooleate).

The aqueous solutions may also contain one or more preservative(s) (e.g., ethyl p-hydroxybenzoate and propyl p-hydroxybenzoate), antioxidant(s) (e.g., ascorbic acid), coloring agent(s), corrigent(s), and/or sweetener(s) (e.g., sucrose, saccharine, and aspartame).

The oily suspensions may be prepared by suspending an active ingredient in a plant oil (e.g., peanut oil, olive oil, sesame oil, or coconut oil) or a mineral oil (e.g., liquid paraffin). The oily suspensions may also contain a thickener such as beeswax, solid paraffin, or cetyl alcohol. To provide palatable oral preparations, such sweetener(s) and corrigent(s) as described above may be added thereto. These compositions may be stored by adding thereto an antioxidant such as ascorbic acid.

The dispersible powders and granules suitable for producing aqueous suspensions by addition of water generally comprise the active ingredient, together with a dispersant or wetting agent, a suspending agent, and one or more preservative(s). Appropriate dispersants or wetting agents and suspending agents are as described above. Moreover, additional excipients such as sweeteners, corrigents, and coloring agents may be contained therein.

Moreover, the pharmaceutical compositions of the present invention may be in a form of water-in-oil emulsion. The oil phase can be a plant oil (e.g., olive oil or peanut oil) or a mineral oil (e.g., liquid paraffin), or any mixture thereof. Appropriate emulsifying agents can be, for example, naturally existing gums (e.g., gum arabic and tragacanth gum), naturally existing phosphatides (e.g., soybean and lecithin), esters or partial esters derived from fatty acids and hexitol anhydrides (e.g., sorbitan monooleate), and condensation products of the partial esters and ethylene oxide (e.g., polyoxyethylene sorbitan monolaurate). The emulsions may also contain a sweetener, a corrigent, and a preservative.

The syrups and the elixirs may be prepared together with a sweetener such as glycerol, propylene glycol, sorbitol, aspartame, or sucrose and may contain a demulcent, preservative, corrigent, and/or coloring agent.

The pharmaceutical composition may be in a form of sterile injectable. The injectables can be prepared according to known approaches using one or more of the appropriate dispersants or wetting agents and suspending agents described above.

Moreover, the sterile injectable formulations may be sterile injectable solutions or suspensions in a nontoxic, parenterally acceptable diluent or solvent, for example, 1,3-butanediol solutions.

The pharmaceutical compositions for use in administration by an inhalation method may be in a form of conventional pressurized aerosol that is adjusted to distribute an active ingredient either as an aerosol containing pulverized solid or as an aerosol containing liquid droplets. Conventional aerosol propellants such as volatile fluorinated hydrocarbons or hydrocarbons may be used. An aerosol apparatus is appropriately adjusted to distribute a constant amount of an active ingredient.

For further information about preparation, the reader may refer to chapter 25.2, Vol. 5, Comprehensive Medicinal Chemistry (Corwin Hansch; editor in chief; Pergamon Press, 1990).

The amount of an active ingredient contained together with one or more excipient(s) for producing one dosage form is inevitably predicted to vary according to the host to be treated and particular administration route. For example, a preparation intended for oral administration to a human is generally predicted to comprise, for example, 0.5 mg to 2 g of the active ingredient formulated together with an appropriate and convenient amount of excipient(s). In this context, the amount of excipients can vary within a range of, but not limited to, 5 to 98% by weight of total weight of a composition. A unit dosage form is generally predicted to comprise approximately 1 mg to approximately 500 mg of an active ingredient. For further information about administration routes and dose schedules, the reader may refer to Chapter 25.3, Vol. 5, Comprehensive Medicinal Chemistry (Corwin Hansch; editor in chief; Pergamon Press, 1990).

The pharmaceutical compositions of the present invention may also comprise, in addition to a compound disclosed herein, one or more known agent(s) selected from clinically useful antibacterial agents, for example, but not limited to, macrolide (e.g., erythromycin, telithromycin, dirithromycin, roxithromycin, clarithromycin, azithromycin or fidaxomicin), quinolone (e.g., ciprofloxacin, norfloxacin, levofloxacin, moxifloxacin or sitafloxacin), 3-lactam (e.g., amoxicillin, cefalexin, cefaclor, cefuroxime, cefdaloxime, cefepime, ceftobiprole or cefetrizole), aminoglycosides (e.g., gentamicin, neomycin or streptomycin), and carbapenems (e.g., meropenem or imipenem) and/or other anti-infective agents (e.g., anti-fungal triazoles and amphotericin). Other active pharmaceutical agent which can be used in combination with compounds of the present invention include metronidazole and/or vancomycin. The other active agent may be co-administered with a compound of the present invention simultaneously, continuously, or separately. The use of such active agents can expand therapeutic effectiveness of a pharmaceutical composition of the present invention.

As described above, the magnitude of a dose necessary for therapeutic or preventive treatment of a particular condition is inevitably predicted to vary according to host to be treated, administration route, and severity of diseases to be treated. Preferably, the daily dose is used within the range of 1 to 50 mg/kg. However, the daily dose is inevitably predicted to vary according as described above. Thus, the optimum dose may be determined by any general practitioner that provides treatment to a patient.

In a particular embodiment, a pharmaceutical composition is provided to treat or prevent bacterial infectious diseases.

In another particular embodiment, a pharmaceutical composition is provided to treat or prevent bacterial infectious diseases caused by Gram-positive bacteria selected from genus *Staphylococcus, Streptococcus, Enterococcus, Clostridium, Bacillus, Corynebacterium*, and *Listeria* species.

In another particular embodiment, a pharmaceutical composition is provided to treat or prevent bacterial infectious diseases caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

In yet another particular embodiment, a pharmaceutical composition is provided to treat or prevent bacterial infectious diseases selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, gas gangrene, food poisoning, tetanus, botulism, diarrhea, pseudomembranous colitis, toxic mega colon, and perforation of colon.

As described, a compound of general formula (I) has therapeutic applications and may be used to treat or prevent bacterial infections.

Thus, the present invention in its another aspect provides a method for treating or preventing bacterial infection in a patient comprising the steps of administering to said patient a therapeutically effective amount of a compound of general formula (I), a regioisomer, a stereoisomer, a polymorphic form, a hydrate, or a pharmaceutically acceptable salt thereof, or a pharmaceutical composition containing the same.

According to a further aspect, the present invention provides a compound represented by general formula (I), or a regioisomer, or a stereoisomer, a polymorphic form, or a pharmaceutically acceptable salt thereof, which is intended for use in treating bacterial infections in a patient.

According to a further aspect, the present invention provides a method for inhibiting bacterial DNA gyrase GyrB subunit and/or topoisomerase IV ParE subunit in a patient in need of antibacterial treatment. This method comprises administering an effective amount of a compound represented by general formula (I), or a regioisomer, or a stereoisomer, a polymorphic form, or a pharmaceutically acceptable salt thereof in a patient.

A further aspect of the present invention provides a compound represented by general formula (I), or a regioisomer, or a stereoisomer, a polymorphic form, or a pharmaceutically acceptable salt, which is intended for use as a pharmaceutical agent for producing antibacterial effect in a patient.

A further aspect of the present invention provides a compound represented by formula (I), or a regioisomer, or a stereoisomer, a polymorphic form, or a pharmaceutically acceptable salt, which is intended for use as a pharmaceutical agent for inhibiting bacterial DNA gyrase GyrB subunit and/or topoisomerase IV ParE subunit in a patient.

In one particular embodiment, there is provided a compound of formula (I), or a regioisomer, or a stereoisomer, a polymorphic form, or a pharmaceutically acceptable salt, which is intended for use as a pharmaceutical agent for treating bacterial infections in a patient.

According to a further aspect, the present invention provides use of a compound represented by general formula (I), or a regioisomer, or a stereoisomer, a polymorphic form, or a pharmaceutically acceptable salt, in the production of a pharmaceutical agent used for inhibiting bacterial DNA gyrase GyrB subunit and/or topoisomerase IV ParE subunit in a patient.

In a particular embodiment, the present invention provides use of a compound represented by general formula (I), or a regioisomer, or a stereoisomer, a polymorphic form, or a pharmaceutically acceptable salt, in the production of a pharmaceutical agent used for treating bacterial infections in a patient.

According to a further aspect, the present invention provides a compound represented by general formula (I), or a regioisomer, or a stereoisomer, a polymorphic form, or a pharmaceutically acceptable salt, which is intended for use for producing an antibacterial effect in a patient.

According to a further aspect, the present invention provides a compound represented by general formula (I), or a regioisomer, or a stereoisomer, a polymorphic form, or a pharmaceutically acceptable salt, which is intended for use for inhibiting bacterial DNA gyrase GyrB subunit and/or topoisomerase IV ParE subunit in a patient.

According to a particular embodiment, the present invention provides a compound represented by general formula (I), or a regioisomer, or a stereoisomer, a polymorphic form, or a pharmaceutically acceptable salt, which is intended for use for treating bacterial infections in a patient.

As used herein the term "therapeutically effective amount" refers to the amount of a compound of the present invention, when administered to a patient for treating or preventing bacterial infections, is sufficient to effect such treatment or prevention.

As used herein the term "patient" refers to a subject such as a human suffering from bacterial infections as defined hereinafter and needs therapeutic intervention for the treatment and/or prevention of such bacterial infections.

As used herein the term "bacterial infections" refer to infections caused by Gram-positive, and Gram-negative bacteria including resistant bacteria thereof. The most common organisms include *Staphylococcus, Streptococcus, Enterococcus, Clostridium, Bacillus, Corynebacterium, Haemophilus* and *Listeria* species. The diseases caused by said bacteria include, but are not limited to, pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

In another embodiment of the present invention, there is provided a method for treating infectious diseases especially caused by a pathogen selected from methicillin-resistant *Staphylococcus aureus* (MRSA), penicillin-resistant *Streptococcus pneumoniae* (PRSP), and vancomycin-resistant *Enterococcus* (VRE), and *Clostridium difficile*.

MRSA is a bacterium that is resistant to common antibiotics like penicillin. It can cause skin, bloodstream and surgical wound infections and pneumonia. Compounds disclosed herein are superior to linezolid in terms of in vitro antibacterial activity, efficacy and Frequency of Resistance.

*Clostridium difficile* infection (CDI) is an intestinal disease caused by an anaerobic bacteria *C. difficile* which colonizes in colon. *C. difficile* produces spore and toxins which are responsible for its pathogenesis. The clinical symptoms due to CDI are diarrhea and abdominal pain and in severe cases pseudomembranous colitis, toxic mega colon, and death. Frequent recurrence is also very common even after successful treatment due to the formation of spores. CDI incidences are increasing worldwide. CDI-related death has increased due to the spread of a hyper virulent NAP1/027 strain in the US and Europe.

The compounds of the present invention are active against hypervirulent NAP1/027 strains, hence provide opportunity to treat bacterial infections such as MRSA and CDI.

Accordingly, the present invention provides compounds for use in the treatment of MRSA infections, community-acquired respiratory infections, *Clostridium difficile* infections and clinical symptoms thereof such as diarrhea, pseudomembranous colitis, toxic mega colon, perforation of colon and sepsis.

In another embodiment of the present invention, there is provided a method for treating infectious diseases caused by MRSA.

In another embodiment of the present invention, there is provided a method for treating CDI.

In another embodiment of the present invention, there is provided a method for treating infectious diseases caused by PRSP and VRE.

*Haemophilus influenzae*, a Gram negative bacteria, can cause many kinds of infections including, but not limited to, ear infections, bacteremia, community-acquired respiratory infections, pneumonia and acute bacterial meningitis. Surprisingly, the compounds of the present invention were found to be very active against this pathogen, and hence can be employed for the treatment of said infections caused by *Haemophilus influenzae*.

Accordingly, the present invention provides compounds for use in the treatment of diseases such as community-acquired respiratory infections, pneumonia, bacteremia and acute bacterial meningitis caused *Haemophilus influenzae*.

*Propionibacterium acnes*, a Gram-positive human skin commensal that prefers anaerobic growth conditions and is involved in the pathogenesis of acne, can cause skin disease such as acne vulgaris, which is the most commonly associated with *P. acnes* infection. In addition, *P. acnes* have been associated with endocarditis of prosthetic and native aortic valves, corneal infections and postoperative endophthalmitis. It has also been recognized as a source of infection in focal intracranial infections and various cerebrospinal fluid shunt infections. Surprisingly, the compounds of the present invention were found to be very active against this pathogen, and hence can be employed for the treatment of said infections, preferably acne vulgaris.

*Neisseria gonorrhoeae*, a Gram negative bacterium, can cause gonorrhoea, which is the most common disease associated with *N. gonorrhoeae*. In addition, *N. gonorrhoeae* can also cause conjunctivitis, pharyngitis, proctitis, urethritis, prostatitis or orchitis. Surprisingly, the compounds of the present invention were found to be very active against this pathogen, and hence can be employed for the treatment of said infections, preferably gonorrhoea.

In one particular embodiment, there is provided compounds for use in the treatment of diseases including, but not limited to, community-acquired respiratory infections, hospital-acquired infections, urinary tract infections, acne vulgaris, gonorrhoea and *Clostridium difficile* infections.

Next, general methods of preparation of a compound of the present invention will be provided.

In general, a compound of the present invention can be prepared by following general scheme and experimental procedures described hereinafter and/or by additional or alternative known processes and procedures in combination with knowledge of ordinary skill in the art. It should be understood that the methods set forth in the following general scheme are intended for illustrative purposes and are not to be construed as limiting the scope of the disclosure.

Thus, in another aspect, the present invention provides synthetic methods for producing a compound represented by general formula (1) or a pharmaceutically acceptable salt thereof.

In Scheme 1, a general method of preparation of compounds of the present invention is provided.

Scheme 1

[Chem. 26]

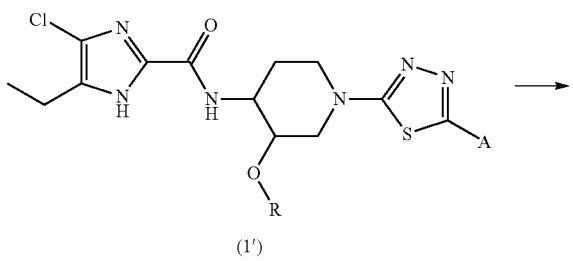

(1')

-continued

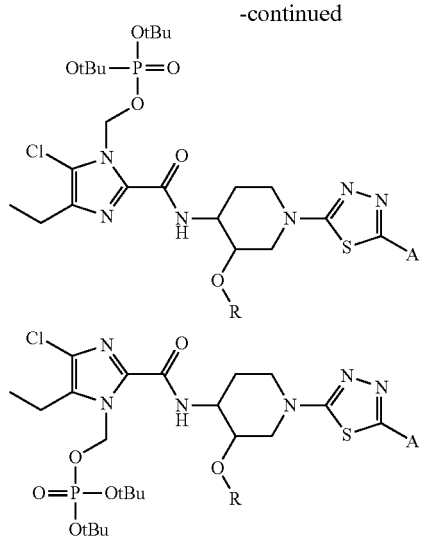

(1)

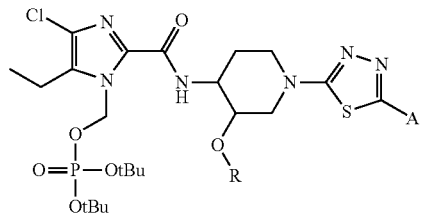

The compound of general formula (1) can be prepared by following the steps of Scheme 1. In a first step, compound of formula (1') is reacted with di-tert-butyl chloromethyl phosphate in presence of a suitable base such as potassium carbonate or cesium carbonate in a suitable solvent such as dimethylformamide at room temperature to form a mixture of regioisomers. The mixture of regioisomers thus formed is subjected to hydrolysis under acidic condition such as acetic acid and water in a suitable solvent such as methyl tert-butyl ether or dimethylsulfoxide, followed by separation using preparative high performance liquid chromotagraphy (HPLC) to obtain pure regioisomer.

General Methods of Preparation of Compounds of Formula (1'):

In Scheme 2, a general method of preparation of compounds of formula (1') is provided.

Scheme 2

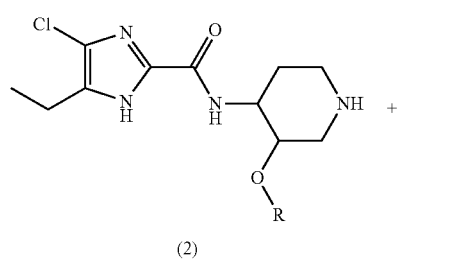

(2)

[Chem. 27]

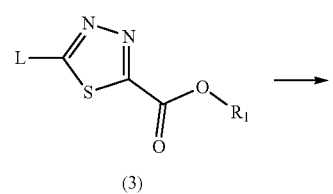

(3)

-continued

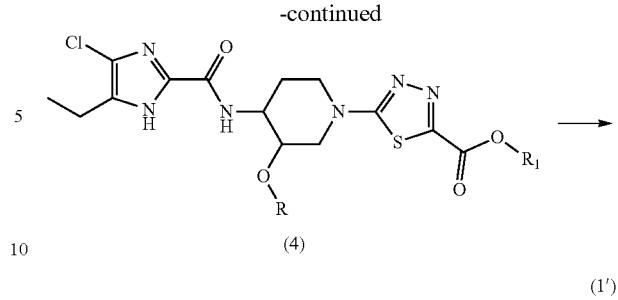

(4)

(1')

The compound of general formula (1') can be prepared by following the steps of Scheme 2. In a first step, a nucleophilic substitution reaction of a compound of formula (2) with (3) (wherein L represents a suitable leaving group such as halogen selected from fluorine, chlorine, bromine, or iodine; $R_1$ represents alkyl group) is carried out with heating in a suitable solvent such as dimethylformamide in the presence of a base such as diisopropylethylamine to obtain a compound of formula (4). In a second step, the ester group of intermediate compound of formula (4) is converted into a compound of general formula (1'): (a) by alkylation (Grignard reaction), when A in general formula (1') is

[Chem. 27]

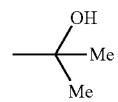

in a suitable solvent such as tetrahydrofuran in the presence of a methyl metal compound such as methylmagnesium bromide (in tetrahydrofuran) at or below 20° C., more preferably at or below 0° C. (b) by reduction, oxidation, followed by alkylation, when A in general formula (1') is

[Chem. 28]

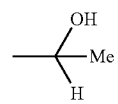

wherein, the reduction of a compound of formula (4) is carried out at room temperature in a suitable solvent such as methanol in the presence of a reducing agent such as sodium borohydride to obtain an alcohol intermediate, which upon oxidation at room temperature in a suitable solvent such as methylene chloride in the presence of an oxidizing agent such as manganese dioxide gives an aldehyde intermediate, which is finally subjected to alkylation (Grignard reaction) as described above.

The compound represented by formula (3) is commercially available, already known in literature, or synthesized by standard synthetic methods well known in the art.

The compound represented by formula (2) can be prepared following the reaction sequence as depicted below:

[Chem. 29]

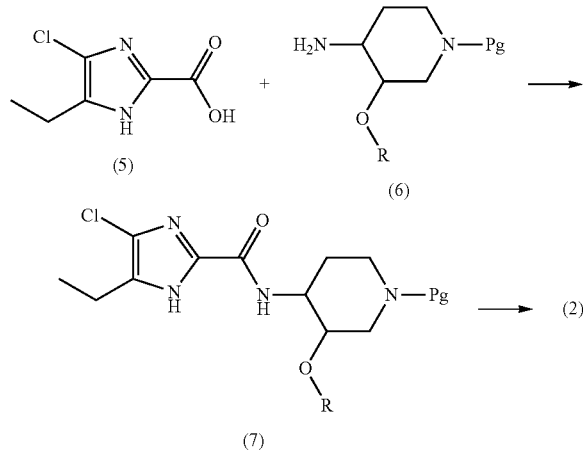

The intermediate compound of formula (2) can be prepared by condensation reaction, followed by deprotection. Firstly, an imidazole compound of formula (5) is condensed with a compound of formula (6) (wherein R is as defined above, and Pg is a protecting group such as tert-butyloxycarbonyl, methoxycarbonyl, ethoxycarbonyl or p-methoxy benzyl) in the presence of a suitable peptide coupling reagent known in the art, or a coupling agent such as 1-ethyl-3-(3-dimethylaminopropyl) carbodiimide hydrochloride (EDCI). Such a condensation reaction is sometimes carried out in the presence of a catalyst such as 1-hydroxybenzotriazole (HOBT) or dimethylamino pyridine, and sometimes in the presence of a base such as triethylamine or di-isopropylethylamine, in a suitable solvent such as dichloromethane, tetrahydrofuran, N,N-dimethylacetamide and dimethylformamide, and in a temperature range of −40° C. to 80° C.

In a second step, the compound of formula (7) is subjected to deprotection reaction in a suitable solvent such as methanol, in the presence of an acid such as a hydrogen chloride in ethyl acetate.

The imidazole compound of formula (5) is known in the literature (WO 2009/084614). The compound of formula (6) is commercially available or known in the literature. It can also be synthesized following procedure described in the art, for example WO 2006/087543.

In certain cases, optically pure compound of formula (6) can be prepared by following procedures described hereinafter.

A methylated derivative of the compound represented by formula (3) such as (3a), a dimethylated compound, or (3b), a monomethylated compound, is preferably employed as synthetic intermediates for compound (I).

[Chem. 30]

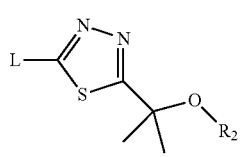

(3a)

-continued

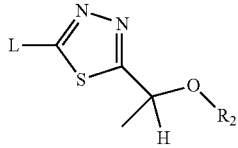

(3b)

Under these circumstances, the methylated compound of formula (4) such as (4a) or (4b) is directly prepared, which avoids alkylation step as shown in scheme 1 above.

[Chem. 31]

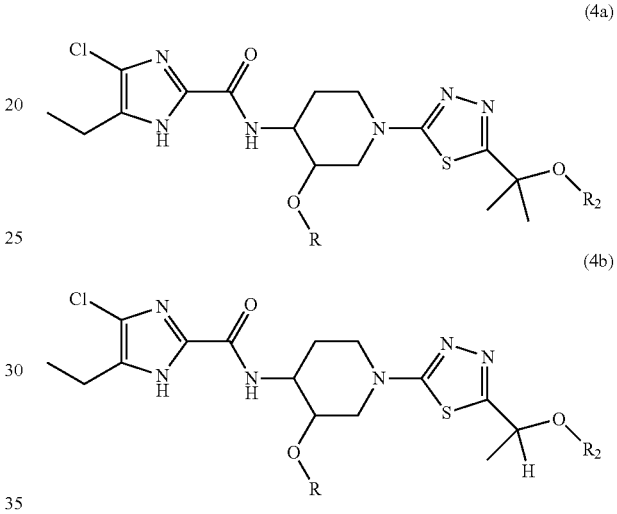

The use of a compound (3a) or (3b) is advantageous as it enables to avoid contamination of carbonyl impurity at the alkylation step of the compound of formula (4).

More specifically, the bromo-derivative of (3a) or (3b), wherein L in the formula (3a) or (3b) is bromine, is preferably used for the reaction. The bromo-derivative of (3a) or (3b) is obtained by the reaction of corresponding amino-derivative of compound (3a) or (3b), wherein L in the formula (3a) or (3b) is —NH$_2$, by the bromination of diazonium compound obtained by reacting sodium nitrite with the amino compound of (3a) and (3b) according to the known method. The amino-derivative of compound (3a) or (3b) is obtained by the reaction of hydrazinecarbothioamide and 2-(R$_2$—O-)-2-methylpropionic acid or 2-(R$_2$—O-)-propionic acid in the presence of phosphorous chlorinating agent such as phosphorous oxy chloride, phosphorous pentachloride, phosphorous trichloride and the like. Any solvent which does not interfere with the reaction can be employed for this reaction, and ether such as dioxane, 1,2-dimethoxyethane; hydrocarbon such as benzene, toluene, xylene; halogenated hydrocarbon such as chloroform, 1,2-dichloethane; ester such as ethyl acetate, propyl acetate, butyl acetate are exemplified. With regard to the (R$_2$—O—)— moiety of 2-(R$_2$—O-)-2-methylpropionic acid ester or 2-(R$_2$—O-)-propionic acid ester, this moiety is preferably those derived from the protection of hydroxy group of 2-hydroxy-propionic ester by some protective group for hydroxy group. Such protective group for hydroxy group may be selected from those known in the art; alkyl group such as methyl group, tert-butyl group; aralkyl group such as benzyl group, p methoxy benzyl group; acyl group such as acetyl group, pivaloyl group, benzoyl group are exemplified. As for the (R₂—O—)— moiety, acyloxy group is preferably employed and benzoyloxy group is more preferable used. The deprotection of the protective group R₂ are able to be conducted by the known method corresponding to the protective group actually selected to yield hydroxy group. The reaction of bromo-derivative of (3a) or (3b) with compound (2) is conducted according to the method explained above.

Preferably, the compound of formula (1') is obtained according to Scheme 3, using a bromo-derivative of a compound (3a) or (3b), wherein L is bromine.

Scheme 3

[Chem. 32]

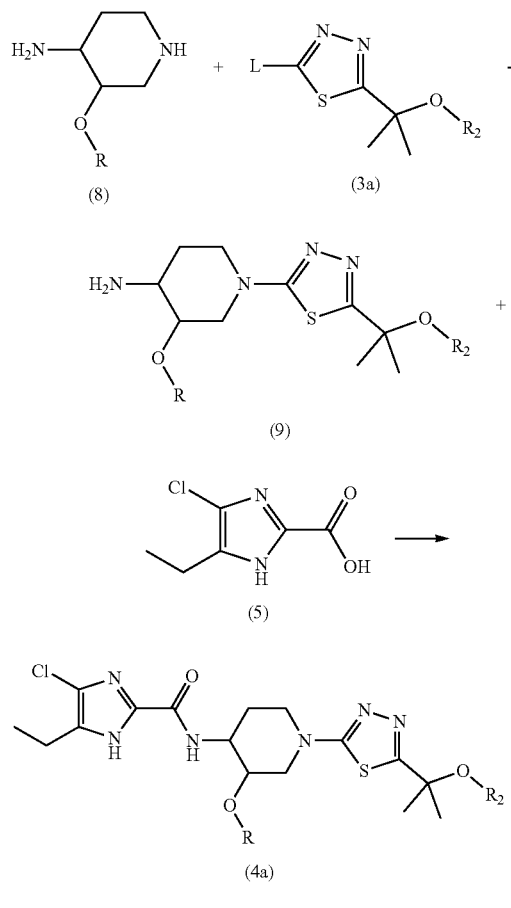

According to this process, thiadiazole moiety is introduced before the introduction of imidazole moiety. The compound of formula (9), specifically a dimethylated derivative, is obtained by the reaction of compound (3a) and compound (8). The resulting compound (9), especially a dimethylated derivative, was obtained as a solid salt of carboxylic acid and such a carboxylic acid salt was purified by a method well know in the relevant art, such as slurry method or recrystallization. As for the salt of compound (9) with carboxylic acid, propionic acid salt is preferably exemplified. This is very advantageous as high purity compound (9) can be obtained to be used as the synthetic intermediate, which can enable to obtain high purity of compound of formula (1'). Free form of compound (9) can be obtained by a known method such as treatment of salt of compound (9) with a base. The reaction of compound (3a) and compound (8) is achieved by the condition explained above.

Compound (9), a dimethylated derivative, can be converted to compound (4a) by the reaction of compound (9) and 4-chloro-5-ethyl-1H-imidazole-2-carboxylic acid (5). This reaction can be achieved under the condition explained later. The removal of R₂ from compound (4a) yields compound (I). This removal can be achieved by known method according to R₂, a protective group, being employed.

The methods described herein intend to preferably include the following embodiments, for example, with regard to preparation of 5-(2-hydroxypropan-2-yl)-1,3,4-thiadiazol-2-yl derivative having the following formula or a stereoisomer thereof

[Chem. 33]

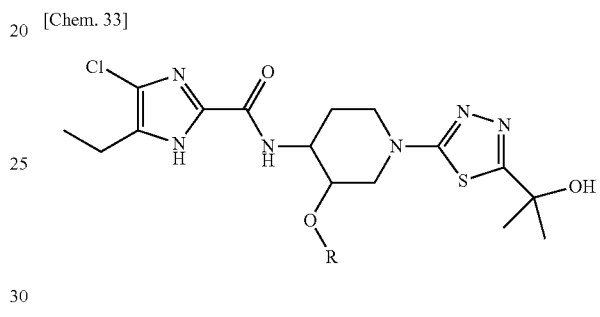

there is provided a method, which comprises di-methylation on carbonyl carbon atom of —C(=O)—O—R₁ of the compound of the following formula or a stereoisomer thereof:

[Chem. 34]

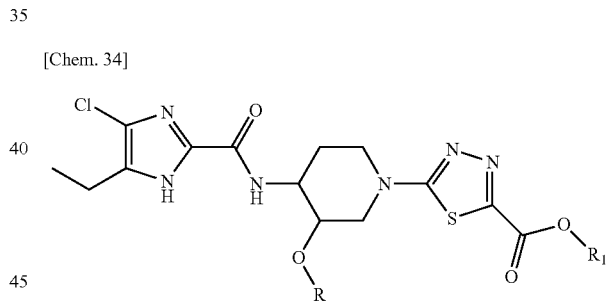

wherein, R represents (C₁-C₃) alkyl group and R₁ represents an alkyl group.

In another embodiment, there is provided a method for the preparation of a compound of the following formula or a stereoisomer thereof

[Chem. 35]

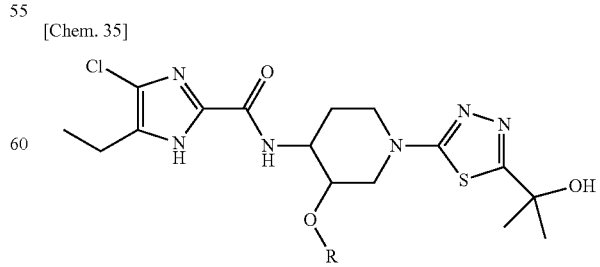

which method comprises the steps of.

i) reacting a compound of the following formula or a stereoisomer thereof:

[Chem. 36]

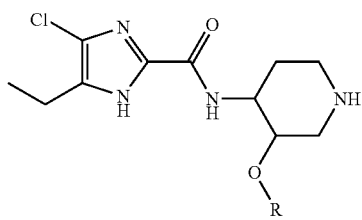

with a compound of the following formula:

[Chem. 37]

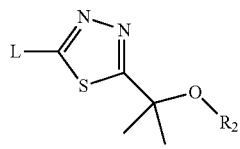

wherein L represents a leaving group, $R_2$ represents a protective group for hydroxy group, and R represents ($C_1$-$C_3$) alkyl group, to obtain a compound of the following formula or a stereoisomer thereof

[Chem. 38]

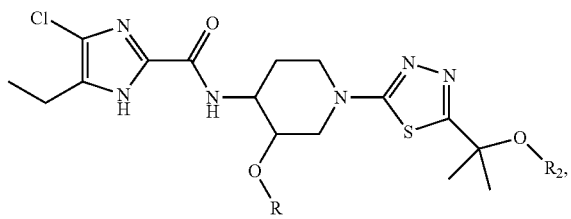

and
ii) deprotecting the compound obtained in step i).

In another embodiment, there is provided a method for the preparation of a compound of the following formula or a stereoisomer thereof:

[Chem. 39]

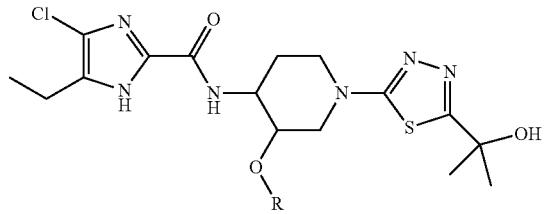

which method comprises the steps of i) reacting a compound of the following formula or a stereoisomer thereof:

[Chem. 40]

with a compound of the following formula:

[Chem. 41]

to obtain a compound of the following formula or a stereoisomer thereof

[Chem. 42]

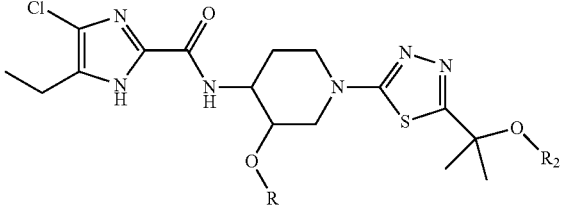

ii) the compound obtained in step i) is reacted with a compound of the following formula:

[Chem. 43]

to obtain a compound of the following formula or a stereoisomer thereof:

[Chem. 44]

and then
iii) deprotecting the compound obtained in step ii), wherein L, R and $R_2$ are as defined hereinbefore.

In a preferred embodiment, the compound obtained by any of the methods described above has the following structure formula:

[Chem. 45]

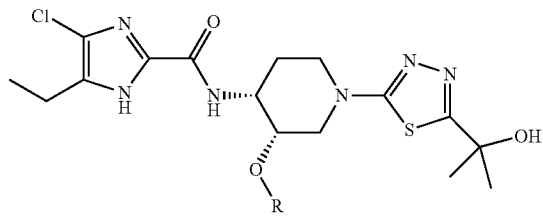

With regard to preparation of 5-(1-hydroxyethyl)-1,3,4-thiadiazol-2-yl derivative having the following formula or a stereoisomer thereof

[Chem. 46]

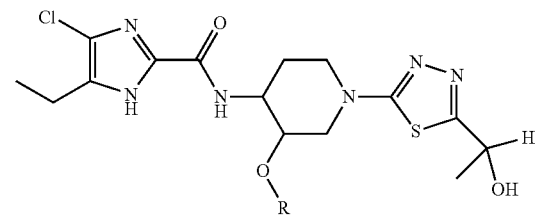

there is provided a method, which comprises the steps of:
i) reducing a compound of the following formula or a stereoisomer thereof:

[Chem. 47]

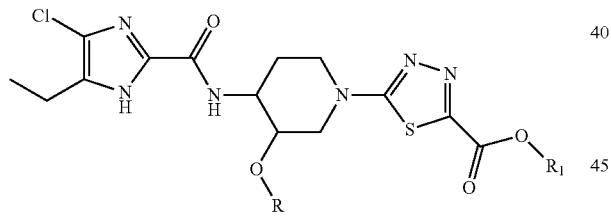

in presence of a suitable reducing agent such as sodium borohydride to obtain a compound of the following formula or a stereoisomer thereof.

[Chem. 48]

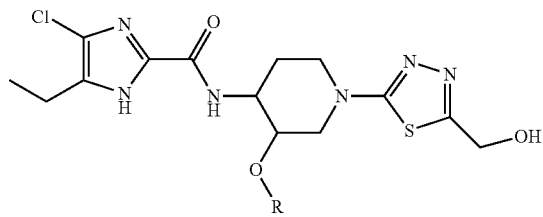

i) oxidizing a compound obtained in step i) using a suitable oxidizing agent to obtain a compound of the following formula or a stereoisomer thereof:

[Chem. 49]

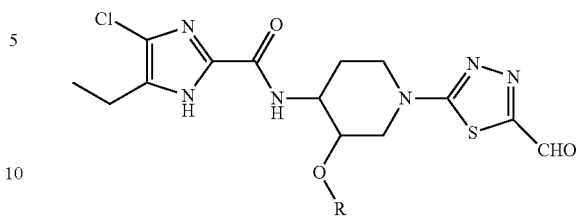

and iii) methylating on the carbon atom of formyl group with Grignard reagent.

In a preferred embodiment, the compound, obtained by following methods described above, has the following structural formula:

[Chem. 50]

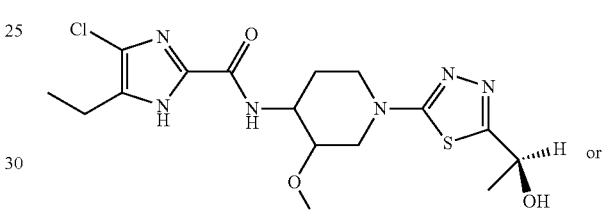

or

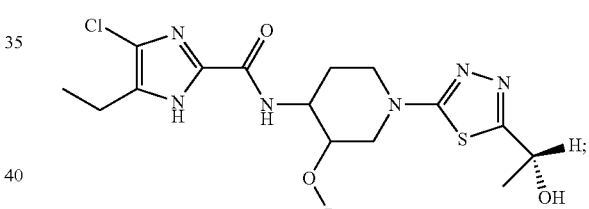

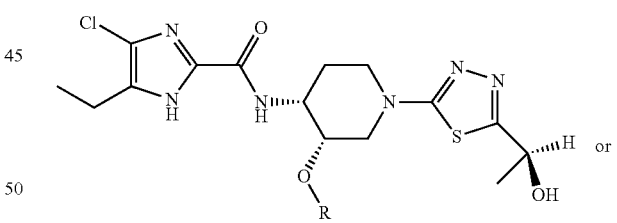

or

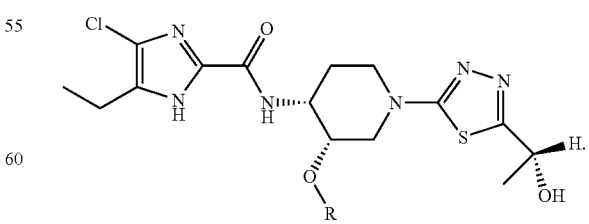

With regard to preparation of 5-(1-hydroxypropan-2-yl)-1,3,4-thiadiazol-2-yl derivative having the following formula or a stereoisomer thereof

[Chem. 51]

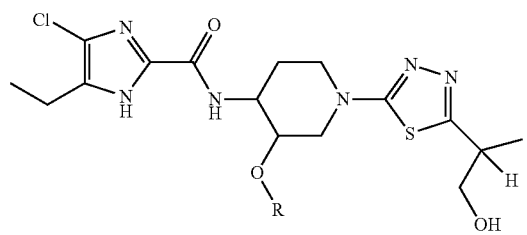

there is provided a method, which comprises reacting a compound of the following formula or a stereoisomer thereof

[Chem. 52]

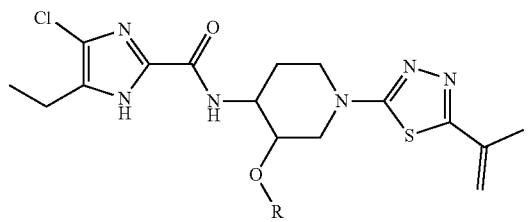

with borane, followed by treatment with hydrogen peroxide.

In a preferred embodiment, the compound obtained following the above method has a structural formula:

[Chem. 53]

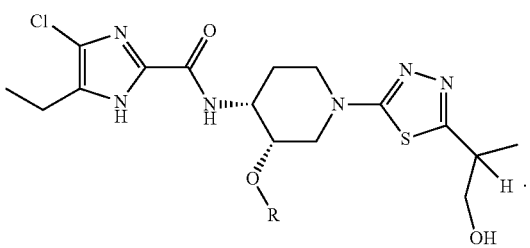

With regard to preparation of 5-[1,2-dihydroxyethyl]-1,3,4-thiadiazol-2-yl derivative having the following formula or a stereoisomer thereof:

[Chem. 54]

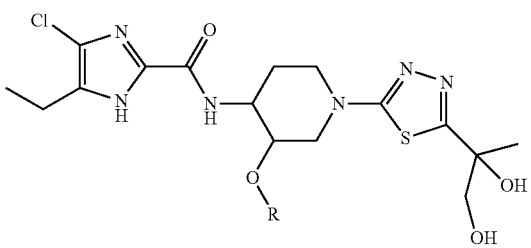

there is provided a method, which comprises dihydroxylating a compound (on 5-etheny group of 1-1,3,4-thiadiazole) of the following formula or a stereoisomer thereof

[Chem. 55]

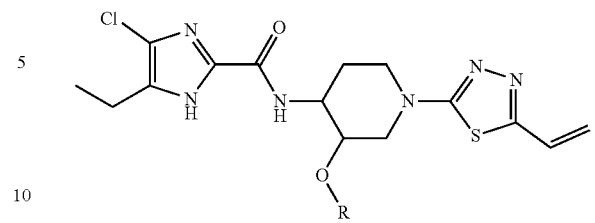

wherein dihydroxylation is Sharpless asymmetric dihydroxylation.

In a preferred embodiment, the compound obtained by following above method has the structural formula:

[Chem. 56]

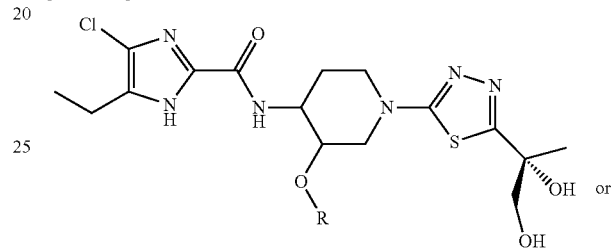

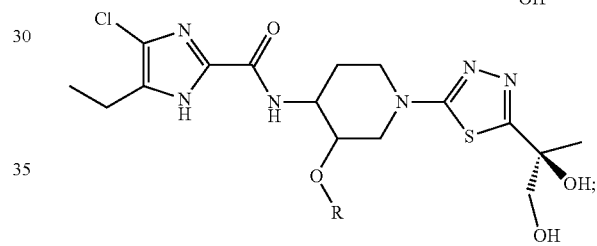

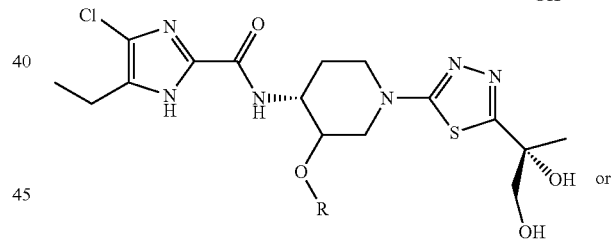

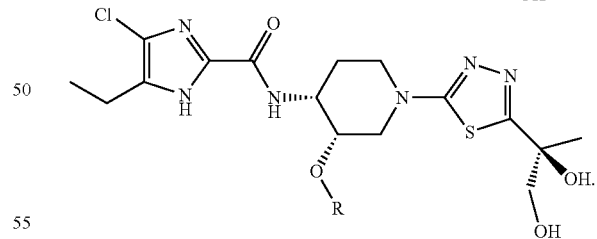

Synthetic methods routinely used by usual organic chemists for producing the pharmaceutically acceptable salts are within the scope of this patent application.

Skilled organic chemists can presumably obtain necessary starting materials and products by using reference documents described below, examples described therein, examples described hereinafter. When starting materials necessary for such approaches as described above are not commercially available, they may be prepared by an approach selected from standard organic chemical techniques similar to the synthesis of structurally similar compounds, and techniques similar to approaches of procedures described above or in examples.

It should be noted that many starting materials for the synthesis methods are commercially available and/or have been reported widely in scientific documents or can be formed from commercially available products by appropriately using synthetic methods reported in scientific documents. As a general guide to reaction conditions or reagents, see Advanced Organic Chemistry, Vol. 4 (Jerry March, ed., published by John Wiley and Sons, 1992).

In certain embodiments, it is to be understood that in place of reducing agent, solvent, protecting groups, organolithium reagents, and base, optionally indicated in one or more methods described herein, any other reducing agent, solvent, protecting agent, organolithium reagents, and base, as described herein, can also be employed.

Conventional protecting groups can be used according to standard techniques (for the illustrative purpose, see T.W. Greene, Protective Groups in Organic Synthesis, John Wiley and Sons, 1991).

Examples of a protecting group suitable for amino group include acyl groups such as alkanoyl groups (e.g., acetyl), alkoxycarbonyl groups (e.g., methoxycarbonyl, ethoxycarbonyl, and tert-butoxycarbonyl), arylmethoxycarbonyl groups (e.g., benzyloxycarbonyl), and aroyl groups (e.g., benzoyl) or p-methoxybenzyl.

Deprotection conditions for the protecting groups inevitably vary according to the selection of the protecting groups. Thus, for example, acyl groups such as alkanoyl or alkoxycarbonyl groups or aroyl groups may be removed, for example, by hydrolysis with an appropriate base such as an alkali metal hydroxide (e.g., lithium hydroxide or sodium hydroxide). Alternatively, alkoxycarbonyl groups (e.g., a tert-butoxycarbonyl group) may be removed, for example, by treatment with an appropriate acid such as hydrochloric acid, sulfuric acid, phosphoric acid, or trifluoroacetic acid. Arylmethoxycarbonyl groups (e.g., a benzyloxycarbonyl group) may be removed, for example, by treatment with hydrogen in the presence of a palladium-supported catalyst (e.g., active carbon) or by treatment with a Lewis acid, for example, boron tris(trifluoroacetate).

Examples of the protecting groups suitable for the carboxyl group include esterifiable substituents, for example, methyl, ethyl, tert-butyl, and benzyl groups.

Deprotection conditions for the protecting groups are inevitably predicted to vary according to the selection of the protecting groups.

Thus, for example, a methyl ester or ethyl ester group may be removed, for example, by hydrolysis with an appropriate base such as sodium hydroxide. For example, a tert-butyl ester group may be removed, for example, by treatment with an organic acid such as trifluoroacetic acid. A benzyl ester group may be removed, for example, by the hydrogenolysis in the presence of a palladium-supported catalyst (e.g., active carbon).

These protecting groups may be removed at any convenient stage of synthesis using conventional techniques well known in the chemical field. Alternatively, the protecting groups may be removed in subsequent reaction steps or during workup. The removal of every protecting group and the formation of a pharmaceutically acceptable salt are within the ability of usual organic chemists to use standard techniques.

When an optically active form of a compound of the present invention is required, this form may be obtained by subjecting an optically active starting material (e.g., formed by asymmetric derivatization in an appropriate reaction step) to any one of the approaches described above; or by resolving a racemic form of the present compound or an intermediate thereof using standard procedures; or by separating a diastereoisomer, if formed, by chromatography. Moreover, enzymatic techniques can also be useful in the production of the optically active compound and/or intermediate.

Likewise, when a pure diastereomer of a compound of the present invention is required, this isomer may be obtained by subjecting a purified diastereomer mixture as a starting material to any one of the approaches described above or by resolving a mixture of diastereomer or intermediates thereof using standard procedures.

The yield is shown only as an example, and is not always necessarily the maximum value achievable.

The structure of a final product of the present invention was generally determined by NMR (referred to the proton magnetic resonance spectrum) and/or mass spectrum (ESI method, APCI method or FAB method). The chemical shift in the proton magnetic resonance ($^1$H-NMR) spectrum is expressed in ppm in a lower magnetic field ($\delta$ scale) relative to tetramethylsilane as the internal standard, and the coupling constant (J) and the peak multiplicity are denoted as follows (s, singlet; d, doublet; dd, doublet of doublet; dt, triplet of doublet; t, triplet; q, quartet; m, multiplet; br, broad). Cation data and anion data are incorporated into mass spectrum as necessary by ESI method, APCI method or FAB method. The measurement was carried out at a rotation angle of 589 nm (25° C.).

Each intermediate is purified and structurally determined to a level required in subsequent steps (the purity is evaluated by TLC or NMR to suitably determine the identity by mass spectrum or NMR spectrum).

In the notation of the compound names, it should be understood that cis (±) or trans (±), when used, means a racemic mixture of cis or trans isomers, and (−) or (+), when referred, means a single enanthiomer as in R, R or S, S.

As a reducing agent, unless otherwise indicated, a hydrogenated complex compound, a boron-containing compound such as sodium borohydride, sodium triacetoxy borohydride or sodium cyano borohydride can be used. In addition, catalytic reduction using a metal catalyst such as palladium carbon, Raney nickel, platinum oxide, palladium hydroxide or palladium black can preferably be used.

According to the present invention, the solvents, unless otherwise indicated, include polar and non-polar solvents well known in the art including polar aprotic and polar protic solvents. The examples of polar solvents include, but are not limited to, methanol, ethanol, isopropyl alcohol, tert-butanol, n-butanol, acetic acid, formic acid or water, or aprotic solvent such as tetrahydrofuran, acetonitrile, dioxane, methylene chloride, dimethylsulfoxide, acetone, N,N-dimethylformamide, N,N-dimethylacetamide, ethyl acetate, 1,2-dimethoxyethane, 1,2-dichloroethane, chloroform or pyridine. Polar solvent also include a mixture of water with any of the above, or a mixture of any two or more of the above solvents. The examples of non-polar solvents include, but are not limited to, toluene, benzene, chlorobenzene, xylenes and hexanes.

Base, unless otherwise indicated, includes, but are not limited to, potassium hydroxide, sodium hydroxide, potassium carbonate, sodium carbonate, cesium carbonate, magnesium carbonate, barium carbonate, methylamine, triethylamine, diisopropylethylamine or pyridine.

In certain embodiments, the present invention encompasses isotopically labeled compounds of general formula (I). All isotopes of any particular atom or element as specified are contemplated within the scope of the present invention. The examples of isotopes that can be incorporated into compounds of the present invention include, but are not limited to, isotopes of hydrogen (e.g., $^2$H or $^3$H), carbon (e.g., $^{13}$C or $^{14}$C), nitrogen (e.g., $^{13}$N or $^{15}$N), oxygen (e.g., $^{15}$O, $^{17}$O or $^{18}$O), phosphorous (e.g., $^{32}$P or $^{33}$P), sulphur (e.g., $^{35}$S), halogen (e.g., $^{18}$F, $^{36}$Cl, $^{123}$I or $^{125}$I). In a preferred embodiment, the present invention provides deuterium (D or $^2$H) compounds of general formula (I). Isotopically labeled compounds of formula (I) can be prepared by following general scheme and methods thereof using isotopically labeled reagents. Isotopically labeled of the present invention may be useful in compound and/or substrate tissue distribution assays. Such applications of isotopically labeled compounds are well known to person skill in the art, and are therefore within the scope of the present invention.

The following abbreviations may sometimes be used. TLC means thin layer chromatography; DMF means N,N-dimethylformamide; THF means tetrahydrofuran; HOBT means 1-hydroxybenzotriazole; EDCI means 1-ethyl-3-(3-dimethylaminopropyl)carbodiimide hydrochloride; DMSO-D6 means deuterated dimethyl sulfoxide; CDCl$_3$ means deuterated chloroform; CD$_3$OD means deuterated methanol; FAB means high-speed atomic collision ionization; ESI means electrospray ionization; APCI means atmospheric pressure chemical ionization.

EXAMPLES

Hereinafter, the present invention is described in detail with reference to examples and test examples, but the scope of the present invention is not limited thereto. Any modification in the procedures described herein, other synthetic procedures and modification thereon can be employed or adapted. All such modifications and alternative procedures are within the spirit and scope of the present application.

Example 1

Synthesis of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 1) and [5-chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 2)

[Chem. 57]

(Compound No. 1)

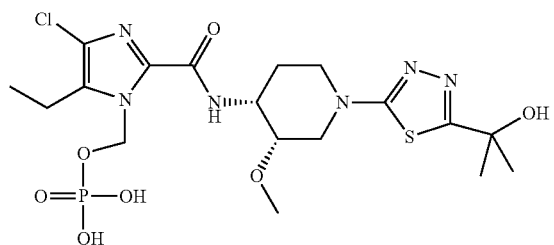

-continued (Compound No. 2)

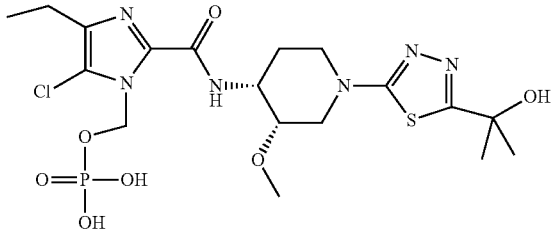

Step 1: Synthesis of tert-butyl cis(±)-4-{[(benzyloxy)carbonyl]amino}-3-methoxypiperidine-1-carboxylate Diisopropylethylamine (26.4 g, 204 mmol) was added to a solution of tert-butyl cis(±)-4-amino-3-methoxypiperidine-1-carboxylate (39.2 g, 170 mmol) in dichloromethane (400 mL), a solution of benzyl chloroformate (43.5 g, 255 mmol) in dichloromethane (80 mL) was added dropwise under ice-cooling, and the mixture was further stirred for 1 hour. The reaction solution was washed with water and 10% aqueous sodium chloride solution and concentrated under reduced pressure. The residue was purified by silica gel chromatography (elution solvent: hexane/ethyl acetate=100/0, 100/15, 100/30), and the resultant was further solidified using a ethyl acetate/hexane mixed solvent to obtain the title compound (40.0 g, 65%) as a white solid.

$^1$H-NMR (400 MHz, CDCl$_3$) δ ppm: 7.29-7.40 (5H, m), 5.10 (2H, s), 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass spectrum (ESI): m/z 365 (M+H)$^+$.

Step 2: tert-butyl (3S,4R)-4-{[(benzyloxy)carbonyl]amino}-3-methoxypiperidine-1-carboxylate tert-Butyl cis(±)-4-{[(benzyloxy)carbonyl]amino}-3-methoxypiperidine-1-carboxylate (100 g, 274 mmol) obtained in Step 1 was optically resolved using an optically active column (CHIRALCEL OJ-H®, elution solvent: hexane/2-propanol=90/10 (v/v)). The first-eluting peak compound (49.5 g) and the second-eluting peak compound (48.9 g) were obtained as colorless oily substances.

$^1$H-NMR (400 MHz, CDCl$_3$) δ ppm: 7.29-7.40 (5H, m), 5.10 (2H, s) 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass (ESI): m/z 365 (M+H)$^+$.

Step 3: Synthesis of tert-butyl (3S,4R)-4-amino-3-methoxypiperidine-1-carboxylate 10% Palladium-carbon (108 g) was added to a solution of the second-eluting peak compound obtained in Step 2 (230 mg, 0.631 mmol) in methanol (7 mL), and the mixture was stirred under a hydrogen gas atmosphere at room temperature for 1 hour and 30 minutes. The reaction solution, from which the catalyst was removed by filtration, was concentrated under reduced pressure to obtain the title compound (141 mg, 97%) as a colorless oily substance.

Step 4: Synthesis of tert-butyl (3S,4R)-4-{[(4-chloro-5-ethyl-1H-imidazol-2-yl)carbonyl]amino}-3-methoxypiperidine-1-carboxylate tert-Butyl (3S,4R)-4-amino-3-methoxypiperidine-1-carboxylate (224.4 mg, 0.96 mmol) obtained in Step 3 above, 4-chloro-5-ethyl-1H-imidazole-2-carboxylate (140 mg, 0.80 mmol) synthesized by the method described in the literature (WO 2009/084614), EDCI (440 mg, 2.29 mmol) and HOBT (110 mg, 0.81 mmol) were mixed in dimethylacetamide, and the mixture was heated at 70° C. for 1 hour. The reaction solution was diluted with ethyl acetate, washed with water 3 times and with brine and dried over anhydrous magnesium sulfate. The solvent was evaporated under reduced pressure, and the resulting residue was purified by silica gel column (ethyl acetate-hexane) to obtain the title compound (222.4 mg, 72%) as a white solid.
$^1$H-NMR (400 MHz, CDCl$_3$) δ ppm: 10.90 (1H, br s), 7.45 (1H, br s), 4.19-4.35 (3H, m), 3.41 (3H, s), 3.32-3.39 (2H, m), 2.72-2.89 (1H, m), 2.68 (2H, q, J=7.57 Hz), 1.79-1.91 (1H, m), 1.61-1.69 (1H, m), 1.47 (9H, s), 1.26 (3H, t, J=7.57 Hz).

Step 5: Synthesis of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate A hydrogen chloride/ethyl acetate solution (4N, 3 mL) was added to a solution of tert-butyl (3S,4R)-4-{[(4-chloro-5-ethyl-1H-imidazol-2-yl)carbonyl]amino}-3-methoxypiperidine-1-carboxylate (1.0 g) obtained in Step 4 in ethyl acetate (3 mL), and the mixture was allowed to stand at room temperature for 30 minutes. The solvent was evaporated under reduced pressure to obtain crude 4-chloro-N-[(3S,4R)-3-methoxypiperidin-4-yl]-5-ethyl-1H-imidazole-2-carboxamide hydrochloride as a colorless amorphous solid.

A suspension of the crude 4-chloro-N-[(3S,4R)-3-methoxypiperidin-4-yl]-5-ethyl-1H-imidazole-2-carboxamide hydrochloride obtained above, ethyl 5-bromo-1,3,4-thiadiazole-2-carboxylate (0.66 g) and sodium bicarbonate (1.05 g) in DMF (40 mL) was stirred at 70° C. for 3 hours. The reaction solution was diluted with ethyl acetate, washed with water and brine, and dried over anhydrous magnesium sulfate. The solvent was evaporated under reduced pressure, and the resulting residue was purified by silica gel column (ethyl acetate-hexane) to obtain the title compound (1.4 g) as a colorless solid.
Mass (ESI): m/z 443 (M+H)$^+$.

Step 6: Synthesis of 4-chloro-5-ethyl-N-{(3S,4R)-1-[5-(1-hydroxy-1-methylethyl)-1,3,4-thiadiazol-2-yl]-3-methoxypiperidin-4-yl}-1H-imidazole-2-carboxamide

[Chem. 58]

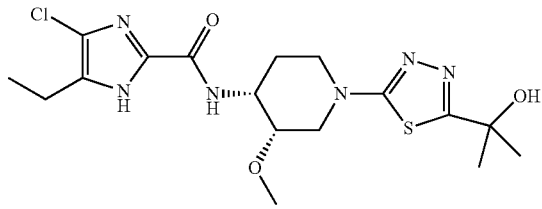

Methylmagnesium bromide (1.12 mol/l THF solution, 10 mL, 11 mmol) was added under ice-cooling to a solution of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate obtained in Step 5 (0.35 g, 0.79 mmol) in THF (15 mL), and the mixture was stirred for 40 minutes. A saturated ammonium chloride solution was added thereto, followed by extraction with ethyl acetate, and the organic layer was washed with brine. The residue obtained by the concentration under reduced pressure was purified by silica gel column (ethyl acetate/methanol) to obtain the title compound (0.40 g, 88%) as a colorless amorphous solid.
$^1$H-NMR (400 MHz, CDCl$_3$) δ: 11.29 (1H, s), 7.53 (1H, d, J=9.16 Hz), 4.48-4.45 (1H, m), 4.27-4.22 (1H, m), 3.85-3.82 (1H, m), 3.52 (1H, s), 3.42 (3H, s), 3.31-3.24 (1H, m), 3.15-3.12 (1H, m), 2.92 (1H, s), 2.70 (2H, q, J=7.64 Hz), 2.12-2.07 (1H, m), 1.81-1.79 (1H, m), 1.68 (6H, d, J=2.29 Hz), 1.26 (3H, t, J=7.64 Hz).

Step 7: Synthesis of di-tert-butyl [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl phosphate (Compound No. 1') and di-tert-butyl [5-chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl phosphate (Compound No. 2')

[Chem. 59]

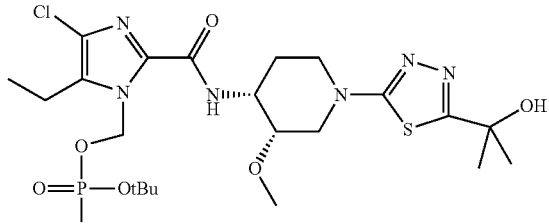
(Compound No. 1')

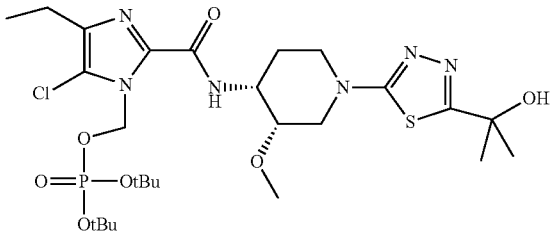
(Compound No. 2')

4-Chloro-5-ethyl-N-{(3S,4R)-1-[5-(1-hydroxy-1-methylethyl)-1,3,4-thiadiazol-2-yl]-3-methoxypiperidin-4-yl}-1H-imidazole-2-carboxamide (Step 6, 30.0 g, 69.9 mmol) was dissolved in dimethylformamide (300 mL) at room temperature. Potassium carbonate (38.6 g, 279.6 mmol, 4 equiv.) was added to the reaction mixture followed by addition of di-tert-butyl chloromethyl phosphate (22.6 g, 87.4 mmol, 1.25 equiv). The reaction mixture was heated at 55° C. for overnight. After completion of reaction, the reaction mixture was diluted with ethyl acetate (500 mL) and washed with brine solution (4×400 mL). The organic layer was separated and concentrated at 40° C. in vacuo. The crude reaction mixture was subjected to column chromatography (3% methanol in dichloromethane) to provide a mixture of regioisomers (38 g). The mixture of regioisomers was taken directly to the next step.

Step 8: Synthesis of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 1) and [5-chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (Compound No. 2)

The mixture of regioisomers (Step 7, 30.0 g, 46.1 mmol) was dissolved in methyl tert-butyl ether (300 mL) at room temperature. A mixture of acetic acid and water (1:1, 7.5 mL each) was added to reaction mixture and was heated at 50° C. The reaction was monitored after 24 hours via MS analyses. A mixture of acetic acid and water (1:1, 7.5 mL each) was further added to the reaction mixture and the reaction was continued till completion of reaction (3-4 days). After completion of reaction the solvents were removed in vacuo at 40° C.) and ethyl acetate (300 mL) was added to reaction mixture which resulted in precipitation of Compound 1 and Compound 2 as a fine white solid (24.8 g). The regioisomers thus formed were separated using preparative HPLC to provide Compound 1 (15 g) and Compound 2 (6.6 g). The separation condition is given in Table 2.

Compound No. 1: $^1$H NMR (400 MHz, DMSO) δ ppm: 7.84 (d, 1H, J=8.36), 6.15 (m, 2H), 5.94 (bs, 1H), 4.12 (m, 3H), 3.78 (d, 1H, J=13.4), 3.54 (bs, 1H), 3.32 (s, 3H), 3.22 (m, 3H), 2.68 (q, 2H, J=7.48), 1.85 (m, 1H), 1.64 (m, 1H), 1.48 (s, 6H), 1.11 (t, 3H, J=7.48). Mass spectrum (ESI): m/z 539.11 (M+H)$^+$.

Compound No. 2: $^1$H NMR (400 MHz, DMSO) δ ppm: 7.81 (d, 1H, J=8.52), 6.14 (d, 3H, J=7.16), 4.13 (m, 2H), 3.79 (m, 1H), 3.56 (s, 1H), 3.34 (s, 3H), 3.24 (m, 2H), 2.5 (m, 4H), 1.85 (m, 1H), 1.67 (m, 1H), 1.48 (s, 6H), 1.13 (t, 3H, J=7.56). Mass spectrum (ESI): m/z 538.81 (M+H)$^+$.

Example 2

Synthesis of (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate (Compound No. 3) and (5-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl)methyl dihydrogen phosphate (Compound No. 4)

[Chem. 60]

(Compound No. 3)

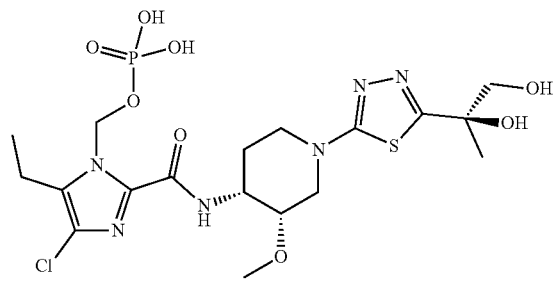

(Compound No. 4)

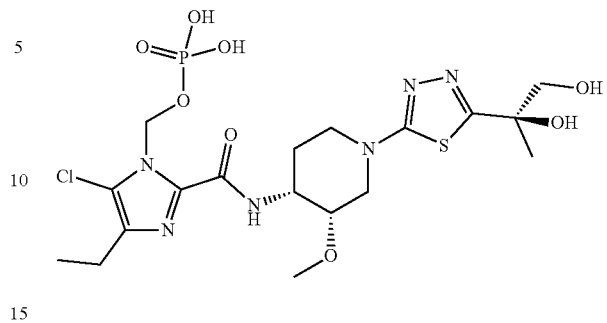

Step 1: Synthesis of 4-chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide

[Chem. 61]

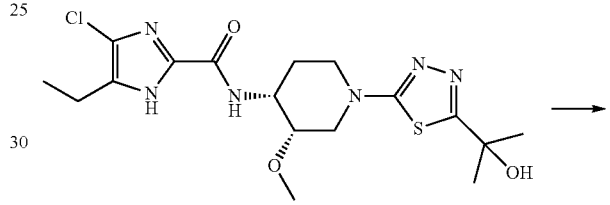

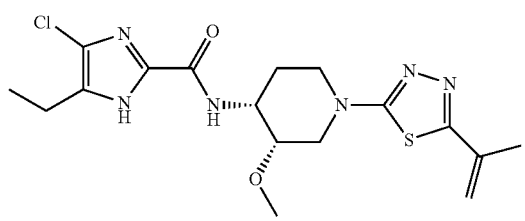

4-Chloro-5-ethyl-N-{(3S,4R)-1-[5-(1-hydroxy-1-methylethyl)-1,3,4-thiadiazol-2-yl]-3-methoxypiperidin-4-yl}-1H-imidazole-2-carboxamide obtained in Example 1, Step 6 (1.0 g, 2.3 mmol) was dissolved in dry toluene (50 mL) at room temperature followed by addition of p-toluenesulfonic acid (39 mg, 0.23 mmol, 0.1 equiv.). The reaction mixture was stirred at 800° C. overnight. After completion of reaction, the reaction mixture was diluted with ethyl acetate and washed with water. The organic layer was separated and concentrated under vacuo. The crude reaction mixture was subjected to column chromatography (methanol-dichloromethane, 5%) to obtain the title compound (575 mg) as pale brown solid.

Mass spectrum (ESI): m/z 411.11 (M+H)$^+$.

Step 2: Synthesis of 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide

[Chem. 62]

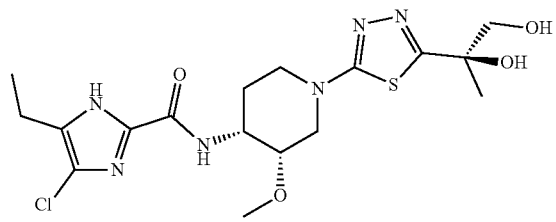

To a solution of AD-mix-α® (20.4 g, 1.4 g/mmol) in t-butanol and water (300 mL each), methanesulfonamide (1.38 g, 14.6 mmol) was added, and the reaction mixture was allowed to stir at 0° C. for 20 minutes. 4-Chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide obtained in Step 1 above (6.0 g, 14.6 mmol was added to the reaction mixture and the mixture was stirred at room temperature for 18 hours. The reaction mixture was quenched by sodium sulfite solution and the reaction mixture was diluted with ethyl acetate (500 mL) and water (50 mL). The organic layer was separated, washed with brine and concentrated. The crude product was purified using column chromatography (10% methanol in dichloromethane) to obtain 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (3.6 g) as off-white amorphous solid.

$^1$H-NMR (400 MHz, CDCl$_3$) δ ppm: 11.89 (s, 1H), 7.64 (d, 1H, J=8.96 Hz), 4.37 (d, 1H, J=13.84 Hz), 4.30-4.20 (m, 1H), 4.13 (d, 1H, J=11.4 Hz), 3.80 (d, 1H, J=13.28 Hz), 3.69 (d, 1H, J=11.36 Hz), 3.50 (s, 1H), 3.37 (s, 3H), 3.22 (dt, 1H, J=13.2, 3.0 Hz), 3.11 (d, 1H, J=13.24 Hz), 2.66 (q, 2H, J=15.16, 7.56 Hz), 2.15-2.05 (m, 1H), 1.80-1.70 (m, 2H), 1.54 (s, 3H), 1.23 (t, 3H, J=7.56 Hz).

Mass: m/z 445.10 (M+H)$^+$.

Step 3: Synthesis of di-tert-butyl (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl phosphate (Compound No. 3') and di-tert-butyl (5-chloro-2-{[(3S,4R)-1-{5-[(2R)-1,2-dihydroxypropan-2-yl]-1,3,4-thiadiazol-2-yl}-3-methoxy piperidin-4-yl]carbamoyl}-4-ethyl-1H-imidazol-1-yl)methyl phosphate (Compound No. 4')

[Chem. 63]

(Compound No. 3')

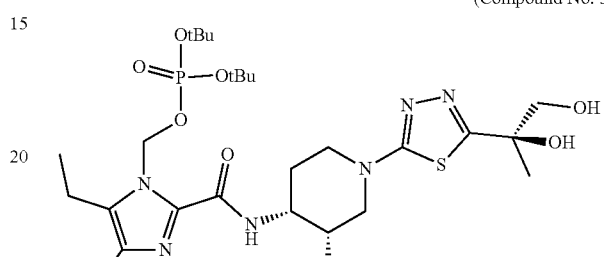

(Compound No. 4')

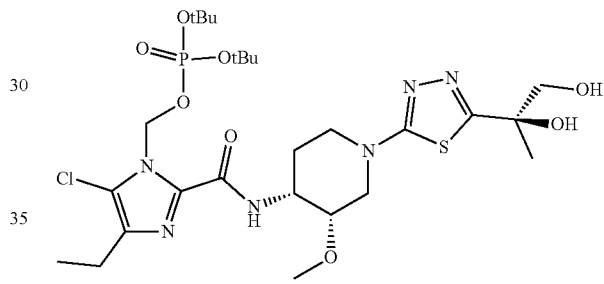

4-Chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (2.0 g, 4.49 mmol) was dissolved in dimethylformamide (30 mL) at room temperature. Potassium carbonate (1.85 g, 13.47 mmol, 3 equiv.) was added to the reaction mixture followed by addition of di-tert-butyl chloromethyl phosphate (1.45 g, 5.61 mmol, 1.25 equiv.). The reaction mixture was heated at 55° C. for overnight. After completion of reaction, the reaction mixture was diluted with ethyl acetate (500 mL) and washed with brine solution (4×50 mL). The organic layer was separated and concentrated at 40° C. in vacuo. The crude reaction mixture was subjected to column chromatography (3% methanol in dichloromethane) to provide final product (2.8 g, mixture of regioisomers). The mixture of regioisomers was separated using preparative HPLC to give Compound 3' (700 mg) and Compound 4' (300 mg) as colorless oil. The separation condition is given in Table 2.

Step 4: Synthesis of (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate and (5-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl) methyl dihydrogen phosphate Compound No. 3' (700 mg, 1.04 mmol) was dissolved in dimethyl sulfoxide (3 mL) at room temperature. A mixture of acetic acid and water (1:1, 0.5 mL each) was added to reaction mixture and was heated at 50° C. The reaction was monitored after 24 hours via MS analyses. A mixture of acetic acid and water (1:1, 0.5 mL each) was further added to the reaction mixture and the reaction was continued till completion of reaction for 3 to 4 days. After completion of reaction the solvents were removed in vacuo using a lyophilizer (at 40° C.) to obtain Compound No. 3 as white solid (150 mg).

$^1$H NMR (400 MHz, MeOD) δ ppm: 6.21 (d, 2H, J=7.52), 4.23 (d, 2H, J=13.56), 3.88 (d, 1H, J=12.21), 3.65 (dd, 2H, J=18.3, 11.2), 3.59 (bs, 1H), 3.44 (s, 3H), 3.34 (m, 2H), 2.77 (q, 2H, J=7.48), 1.97 (m, 1H), 1.79 (m, 1H), 1.59, (s, 3H), 1.21 (t, 2H, J=7.48). Mass: m/z 555.14 (M+H)$^+$.

Similarly, Compound No. 4 (50 mg, white solid) was prepared using Compound 4' (300 mg, 0.45 mmol).

$^1$H NMR (400 MHz, MeOD) δ ppm: 6.12 (m, 2H), 4.23 (t, 2H, J=11.56), 3.89 (m, 1H), 3.65 (dd, 3H, J=18.8, 11.2), 3.59 (bs, 1H), 3.41 (s, 3H), 2.53 (q, 2H, J=8.0), 2.01 (m, 1H), 1.79 (m, 1H), 1.56 (s, 3H), 1.17 (t, 3H, J=7.56). Mass: m/z 555.10 (M+H)$^+$.

Example 3

Synthesis of (4-chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 5) and (5-chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 6)

[Chem. 64]

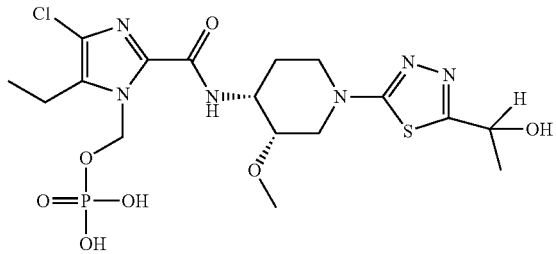
(Compound No. 5)

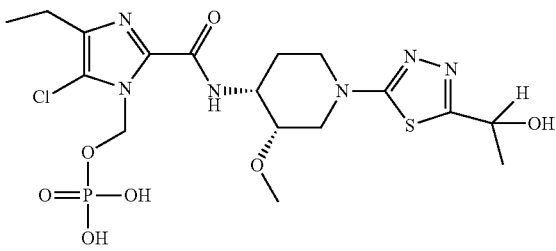
(Compound No. 6)

Step 1: Synthesis of tert-butyl cis(±)-4-{[(benzyloxy)carbonyl]amino}-3-methoxypiperidine-1-carboxylate Diisopropylethylamine (26.4 g, 204 mmol) was added to a solution of tert-butyl cis(±)-4-amino-3-methoxypiperidine-1-carboxylate (39.2 g, 170 mmol) in dichloromethane (400 mL), a solution of benzyl chloroformate (43.5 g, 255 mmol) in dichloromethane (80 mL) was added dropwise under ice-cooling, and the mixture was further stirred for 1 hour. The reaction solution was washed with water and 10% aqueous sodium chloride solution and concentrated under reduced pressure. The residue was purified by silica gel chromatography (elution solvent: hexane/ethyl acetate=100/0, 100/15, 100/30), and the resultant was further solidified using a ethyl acetate/hexane mixed solvent to obtain the title compound (40.0 g, 65%) as a white solid.

$^1$H-NMR spectrum (400 MHz, CDCl$_3$) δ ppm: 7.29-7.40 (5H, m), 5.10 (2H, s), 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass spectrum (ESI): m/z 365 (M+H)$^+$.

Step 2: tert-butyl (3S,4R)-4-{[(benzyloxy)carbonyl]amino}-3-methoxypiperidine-1-carboxylate The tert-butyl cis(±)-4-{[(benzyloxy)carbonyl]amino}-3-methoxypiperidine-1-carboxylate (100 g, 274 mmol) obtained in Step 1 was optically resolved using an optically active column (CHIRALCEL OJ-H®, elution solvent: hexane/2-propanol=90/10 (v/v)). The first-eluting peak compound (49.5 g) and the second-eluting peak compound (48.9 g) were obtained as colorless oily substances.

$^1$H-NMR spectrum (400 MHz, CDCl$_3$) δ ppm: 7.29-7.40 (5H, m), 5.10 (2H, s) 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass spectrum (ESI): m/z 365 (M+H)$^+$.

Step 3: Synthesis of tert-butyl (3S,4R)-4-amino-3-methoxypiperidine-1-carboxylate 10% palladium-carbon (108 g) was added to a solution of the second-eluting peak compound obtained in Step 2 (230 mg, 0.631 mmol) in methanol (7 mL), and the mixture was stirred under a hydrogen gas atmosphere at room temperature for 1 hour and 30 minutes. The reaction solution, from which the catalyst was removed by filtration, was concentrated under reduced pressure to obtain the title compound (141 mg, 97%) as a colorless oily substance.

Step 4: Synthesis of tert-butyl (3S,4R)-4-{[(4-chloro-5-ethyl-1H-imidazol-2-yl)carbonyl]amino}-3-methoxypiperidine-1-carboxylate The same operation as in Example 1 (Step 4) was performed using the tert-butyl (3S,4R)-4-amino-3-methoxypiperidine-1-carboxylate (224.4 mg, 0.96 mmol) obtained in Step 3 above, 4-chloro-5-ethyl-1H-imidazole-2-carboxylate (140 mg, 0.80 mmol) synthesized by the method described in the literature (WO 2009/084614), EDCI (440 mg, 2.29 mmol) and HOBT (110 mg, 0.81 mmol) to obtain title compound (222.4 mg, 72%) as a white solid.

$^1$H-NMR spectrum (400 MHz, CDCl$_3$) δ ppm: 10.90 (1H, br s), 7.45 (1H, br s), 4.19-4.35 (3H, m), 3.41 (3H, s), 3.32-3.39 (2H, m), 2.72-2.89 (1H, m), 2.68 (2H, q, J=7.57 Hz), 1.79-1.91 (1H, m), 1.61-1.69 (1H, m), 1.47 (9H, s), 1.26 (3H, t, J=7.57 Hz).

Step 5: Synthesis of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate A hydrogen chloride/ethyl acetate solution (4N, 3 mL) was added to a solution of tert-butyl (3S,4R)-4-{[(4-chloro- 5-ethyl-1H-imidazol-2-yl)carbonyl]amino}-3-methoxypiperidine-1-carboxylate (1.0 g) obtained in Step 4 in ethyl acetate (3 mL), and the mixture was allowed to stand at room temperature for 30 minutes. The solvent was evaporated under reduced pressure to obtain crude 4-chloro-N-[(3S,4R)-3-methoxypiperidin-4-yl]-5-ethyl-1H-imidazole-2-carboxamide hydrochloride as a colorless amorphous solid.

A suspension of the crude 4-chloro-N-[(3S,4R)-3-methoxypiperidin-4-yl]-5-ethyl-1H-imidazole-2-carboxamide hydrochloride obtained above, ethyl 5-bromo-1,3,4-thiadiazole-2-carboxylate (0.66 g) and sodium bicarbonate (1.05 g) in DMF (40 mL) was stirred at 70° C. for 3 hours. The reaction solution was diluted with ethyl acetate, washed with water and brine, and dried over anhydrous magnesium sulfate. The solvent was evaporated under reduced pressure, and the resulting residue was purified by silica gel column (ethyl acetate-hexane) to obtain the title compound (1.4 g) as a colorless solid.

Mass spectrum (ESI): m/z 443 (M+H)$^+$.

Step 6: Synthesis of 4-chloro-5-ethyl-N-{(3S,4R)-1-[5-(hydroxymethyl)-1,3,4-thiadiazol-2-yl]-3-methoxypiperidin-4-yl}-1H-imidazole-2-carboxamide Sodium borohydride (1.9 g) was added in five divided portions to a solution of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate (1.4 g) obtained in Step 5 above in methanol (50 mL) under ice-cooling, and the mixture was stirred. The reaction solution was concentrated under reduced pressure and water was added to a residue, extracted with ethyl acetate, and dried over anhydrous sodium sulfate. Following concentration under reduced pressure, the residue was purified by silica gel column to obtain the title compound (1.0 g) as an amorphous solid.

$^1$H-NMR (400 MHz, CDCl$_3$) δ ppm: 11.14 (1H, s), 7.53 (1H, d, J=9.03 Hz), 4.88 (2H, s), 4.44-4.48 (1H, m), 4.23-4.27 (1H, m), 3.85-3.87 (1H, m), 3.51 (1H, s), 3.41 (3H, s), 3.28-3.31 (1H, m), 3.14-3.18 (1H, m), 2.80 (1H, br s), 2.70 (2H, q, J=7.57 Hz), 2.05-2.12 (1H, m), 1.78-1.81 (1H, m), 1.26 (3H, t, J=7.69 Hz). Mass (ESI): m/z 401 (M+H)$^+$.

Step 7: Synthesis of 4-chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide

[Chem. 65]

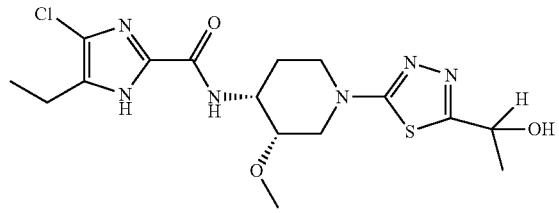

Manganese dioxide (0.42 g) was added to a solution of 4-chloro-5-ethyl-N-{(3S,4R)-1-[5-(hydroxymethyl)-1,3,4-thiadiazol-2-yl]-3-methoxypiperidin-4-yl}-1H-imidazole-2-carboxamide (0.1 g) obtained in Step 6 above in THF (5 mL), and the mixture was stirred at room temperature overnight. After filtering through Celite®, the reaction solution was concentrated under reduced pressure to obtain crude 4-chloro-5-ethyl-N-[(3S,4R)-1-(5-formyl-1,3,4-thiadiazol-2-yl)-3-methoxypiperidin-4-yl]-1H-imidazole-2-carboxamide as an amorphous solid.

Methylmagnesium bromide (1.1 mol/L THF solution, 6 mL) was added under ice-cooling to a solution of crude 4-chloro-5-ethyl-N-[(3S,4R)-1-(5-formyl-1,3,4-thiadiazol-2-yl)-3-methoxypiperidin-4-yl]-1H-imidazole-2-carboxamide in THF (5 mL), and the mixture was stirred. Water and 1 mol/L hydrochloric acid were added, followed by extraction with ethyl acetate, and the organic layer was washed with brine. The residue obtained by the concentration under reduced pressure was purified by silica gel column (ethyl acetate/methanol) to obtain the title compound (0.057 g) as an amorphous solid.

$^1$H-NMR (400 MHz, CDCl$_3$) δ ppm: 11.12 (1H, br s), 7.47-7.57 (1H, m), 5.07-5.18 (1H, m), 4.41-4.51 (1H, m), 4.19-4.31 (1H, m), 3.79-3.91 (1H, m), 3.51 (1H, br s), 3.41 (3H, s), 3.23-3.34 (1H, m), 3.15 (1H, br d, J=14.65 Hz), 2.91 (1H, br s), 2.70 (2H, q, J=7.52 Hz), 2.02-2.15 (1H, m), 1.75-1.84 (1H, m), 1.60-1.64 (3H, m), 1.26 (3H, t, J=7.52 Hz). Mass (ESI): m/z 415 (M+H)$^+$.

Step 8: Synthesis of di-tert-butyl (4-chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl phosphate (Compound No. 5') and di-tert-butyl (5-chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl phosphate (Compound No. 6')

[Chem. 66]

(Compound No. 5')

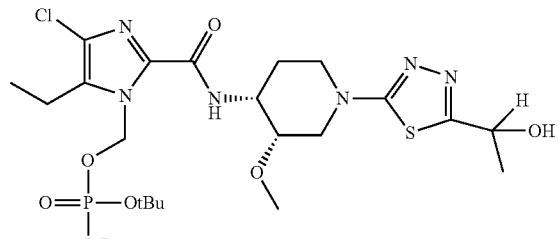

(Compound No. 6')

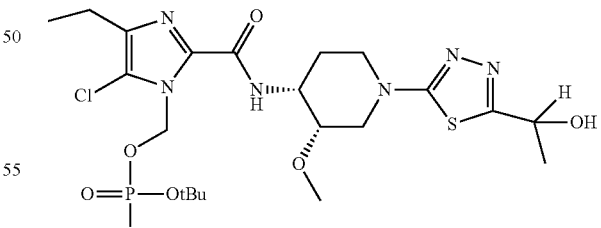

4-Chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide (1.0 g, 2.49 mmol) was dissolved in dimethylformamide (30 mL) at room temperature. Cesium carbonate (2.34 g, 7.2 mmol, 3 equiv.) was added to the reaction mixture followed by addition of di-tert-butyl chloromethyl phosphate (0.932 g, 3.61 mmol, 1.5 equiv.). The reaction mixture was heated at 55° C. for overnight. After completion of reaction, the reaction mixture was diluted with ethyl acetate (500 mL) and washed with brine solution (4×50 mL). The organic layer was separated and concentrated at 40° C. in vacuo. The crude reaction mixture was subjected to column chromatography using 3% methanol in dichloromethane to provide 0.810 g of a mixture of regioisomers 5' and 6'.

Following procedure described in Example 2, the mixture of regioisomer 5' and 6' are separated using preparative HPLC, followed by hydrolysis to obtain Compound No. 5 and Compound No. 6, respectively.

Example 4

Synthesis of (4-chloro-2-{[(3S,4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl dihydrogen phosphate (Compound No. 7) and (5-chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate (Compound No. 8)

[Chem. 67]

(Compound No. 7)

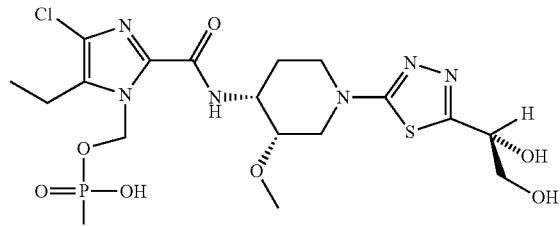

(Compound No. 8)

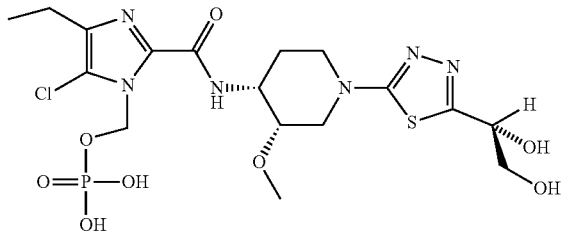

Step 1: Synthesis of N-[(3S,4R)-1-(5-bromo-1,3,4-thiadiazol-2-yl)-3-methoxypiperidin-4-yl]-4-chloro-5-ethyl-1H-imidazole-2-carboxamide The hydrochloride salt of tert-butyl (3S,4R)-4-{[(4-chloro-5-ethyl-1H-imidazol-2-yl)carbonyl]amino}-3-methoxypiperidine-1-carboxylate (2 g, 5.17 mmol) (1.9 g) was prepared by mixing ethyl acetate (20 mL), hydrochloric acid solution (20 ml, 4N in dioxane). After the mixture was allowed to satnd at room temperature for 30 minutes, the solvent of the mixture was evaporated under reduced pressure to yield white solid.

To a solution of this hydrochloride (0.1 g, 0.31 mmole) in acetonitrile (5 mL), diisopropylethylamine (0.15 mL, 0.93 mmol) and 2,5-dibromo-1,3,4-thiadiazole (0.11 g, 0.46 mmol) were added. The reaction mixture was allowed to stir at 80° C. for 4 hours. The reaction mixture was diluted with ethyl acetate (50 mL) and water (5 mL) and stirred for 10 minutes. The organic layer was separated, washed with brine solution and concentrated. The crude product was purified using column chromatography (ethyl acetate in hexane, 30%) to obtain the title compound (84 mg) as off-white gum.

Mass (ESI): m/z 451.07 (M+H)⁺.

Step 2: Synthesis of 4-chloro-N-[(3S,4R)-1-(5-ethenyl-1,3,4-thiadiazol-2-yl)-3-methoxypiperidin-4-yl]-5-ethyl-1H-imidazole-2-carboxamide

[Chem. 68]

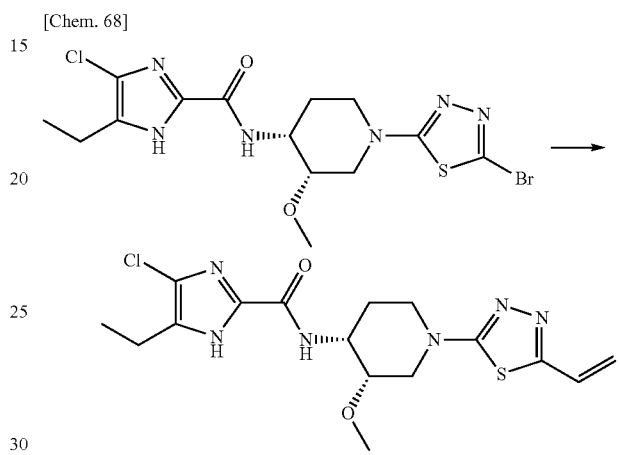

To a solution of N-[(3S,4R)-1-(5-bromo-1,3,4-thiadiazol-2-yl)-3-methoxypiperidin-4-yl]-4-chloro-5-ethyl-1H-imidazole-2-carboxamide (0.08 g, 0.18 mmol) in DMF (5 mL), vinyltributyltin (0.17 mL, 0.53 mmol) and bis-triphenylphosphinepalladium dichloride (0.025 g, 0.03 mmol) were added. The reaction mixture was allowed to stir at 90° C. for 4 hours. The reaction mixture was diluted with ethyl acetate (50 mL) and water (5 mL) and stirred for 10 minutes. The organic layer was separated, washed with brine, and concentrated. The crude product was purified using column chromatography (ethyl acetate in hexane, 40%) to obtain the title compound (26 mg) as off-white gum.

Mass (ESI): m/z 397.14 (M+H)⁺.

Step 3: Synthesis of 4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide

[Chem. 69]

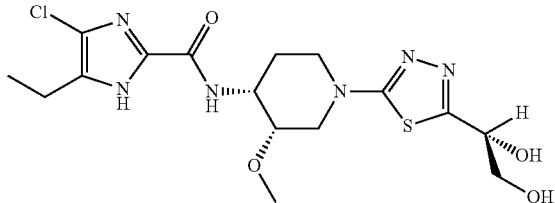

To a solution of AD-mix-ß® (247 mg, 1.4 g/mmol) in t-butanol and water (3 mL each), methanesulfonamide (0.02 g, 0.17 mmol) was added and the reaction mixture was allowed to stir at 0° C. for 20 minutes. 4-Chloro-N-[(3S, 4R)-1-(5-ethenyl-1,3,4-thiadiazol-2-yl)-3-methoxypiperidin-4-yl]-5-ethyl-1H-imidazole-2-carboxamide (0.07 g, 0.17 mmol, obtained in Step 2) was added to the reaction mixture and the mixture was stirred at room temperature for 18 hours. The reaction mixture was quenched by sodium sulfite solution and the reaction mixture was diluted with ethyl acetate (100 mL) and water (5 mL). The organic layer was separated, washed with brine, and concentrated. The crude product was purified using column chromatography (methanol in dichloromethane, 10%) to obtain 4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide (32 mg) as white solid.

$^1$H-NMR (400 MHz, MeOD) δ ppm: 4.30-4.20 (m, 2H), 3.94-3.81 (m, 2H), 3.76-3.71 (m, 1H), 3.60-3.56 (bs, 1H), 3.44 (s, 3H), 3.40-3.30 (m, 3H), 2.64 (q, 2H, J=15.2 and 7.6 Hz), 2.04-1.98 (m, 1H), 1.81-1.79 (m, 1H), 1.21 (t, 3H, J=7.6 Hz). Mass: m/z 430.88 (M+H)$^+$.

Step 4: Synthesis of di-tert-butyl (4-chloro-2-{[(3S, 4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl phosphate (Compound No. 7') and di-tert-butyl (5-chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl phosphate (Compound No. 8')

[Chem. 70]

(Compound No. 7')

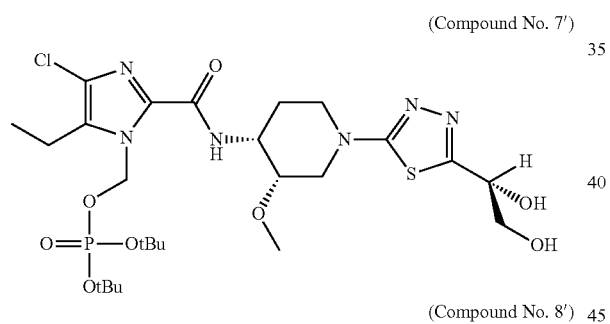

(Compound No. 8')

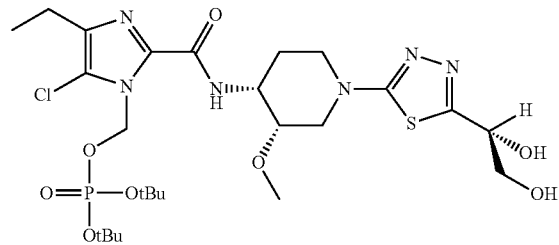

Similarly, a mixture of regioisomers (0.7 g) was prepared following Example 3, Step 3, using 4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide (0.600 g, 1.39 mmol), cesium carbonate (1.35 g, 4.17 mmol, 3 equiv.) and di-tert-butyl chloromethyl phosphate (0.538 g, 4.17 mmol, 1.5 equiv.).

Following procedure described in Example 2, the mixture of regioisomer 7' and 8' are separated using preparative HPLC, followed by hydrolysis to obtain Compound No. 7 and Compound No. 8, respectively.

Example 5

Synthesis of [4-chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl] methyl dihydrogen phosphate (Compound No. 9) and (5-chloro-2-{[(3S,4R)-1-{5-[(1S)-1,2-dihydroxyethyl]-1,3,4-thiadiazol-2-yl}-3-methoxypiperidin-4-yl]carbamoyl}-4-ethyl-1H-imidazol-1-yl) methyl dihydrogen phosphate (Compound No. 10)

[Chem. 71]

(Compound No. 9)

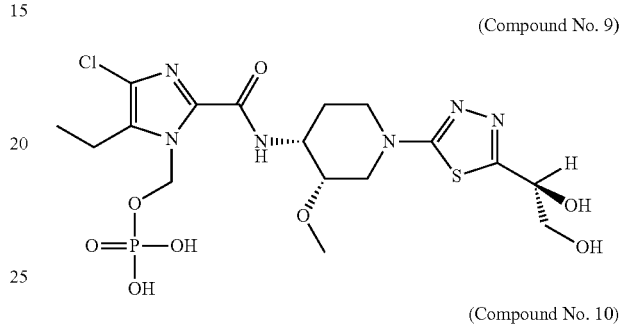

(Compound No. 10)

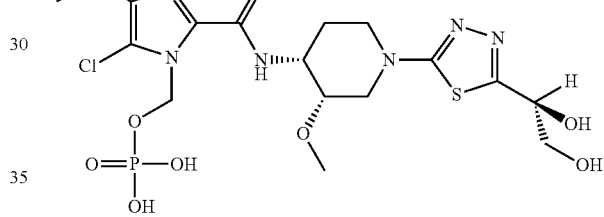

Step 1: Synthesis of 4-chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide

[Chem. 72]

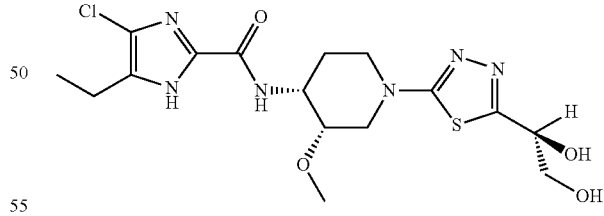

The title compound was prepared following the steps of Example 4. In Step 3, AD-mix-α® (741 mg, 1.4 g/mmol), methanesulfonamide (0.05 g, 0.53 mmol) and 4-chloro-N-[(3S,4R)-1-(5-ethenyl-1,3,4-thiadiazol-2-yl)-3-methoxypiperidin-4-yl]-5-ethyl-1H-imidazole-2-carboxamide (0.21 g, 0.53 mmol) were used to obtain (105 mg) of 4-chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide as white solid.

$^1$H-NMR (400 MHz, MeOD) δ ppm: 4.30-4.20 (m, 2H), 3.93-3.81 (m, 2H), 3.75-3.71 (m, 1H), 3.60-3.55 (bs, 1H), 3.44 (s, 3H), 3.40-3.30 (m, 3H), 2.64 (q, 2H, J=14.8 and 7.6 Hz), 2.04-1.98 (m, 1H), 1.83-1.78 (m, 1H), 1.23 (t, 3H, J=7.6 Hz). Mass: m/z 430.84 (M+H)+.

Step 2: Synthesis of di-tert-butyl [4-chloro-2-({(3S, 4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl phosphate (Compound No. 9') and di-tert-butyl (5-chloro-2-{[(3S,4R)-1-{5-[(1S)-1,2-dihydroxyethyl]-1,3,4-thiadiazol-2-yl}-3-methoxypiperidin-4-yl]carbamoyl}-4-ethyl-1H-imidazol-1-yl)methyl phosphate (Compound No. 10')

[Chem. 73]

(Compound No. 9')

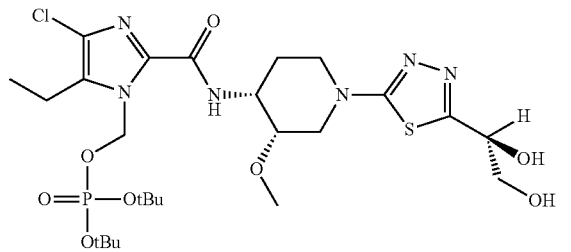

(Compound No. 10')

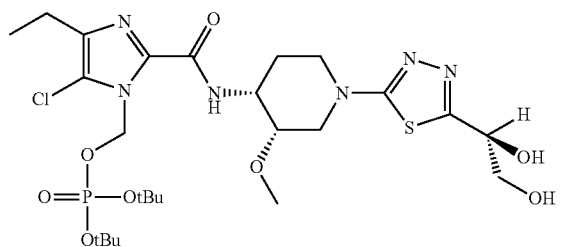

A mixture of regioisomers 9' and 10' (0.810 g) was prepared following the procedure described in Example 3, Step 3, using 4-Chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide (0.600 g, 1.39 mmol), cesium carbonate (1.35 g, 4.17 mmol, 3 equiv.) and di-tert-butyl chloromethyl phosphate (0.538 g, 4.17 mmol, 1.5 equiv.).

Following procedure described in Example 2, the mixture of regioisomers 9' and 10' are separated using preparative HPLC, followed by hydrolysis to obtain Compound No. 9 and Compound No. 10, respectively (the separation condition is given in Table 2).

TABLE 2

Separation condition by preparative HPLC
Solvent A: 0.1% HCOOH in milliQ Water
Solvent B: 0.1% HCOOH in ACN
Column: YMC Pack ODS (500 * 50) mm, 10μ
Flow Rate: 45 mL/min

| Time | A (%) | B (%) |
|---|---|---|
| Gradient for separation of regioisomer (diester stage): | | |
| 0 | 55 | 45 |
| 50 | 45 | 55 |

TABLE 2-continued

Separation condition by preparative HPLC
Solvent A: 0.1% HCOOH in milliQ Water
Solvent B: 0.1% HCOOH in ACN
Column: YMC Pack ODS (500 * 50) mm, 10μ
Flow Rate: 45 mL/min

| Time | A (%) | B (%) |
|---|---|---|
| 55 | 10 | 90 |
| 65 | 0 | 100 |
| 68 | 55 | 45 |
| 75 | 55 | 45 |
| Gradient for separation of regioisomers (diacid stage) | | |
| 0 | 68 | 32 |
| 50 | 38 | 62 |
| 55 | 10 | 90 |
| 65 | 0 | 100 |
| 68 | 68 | 32 |
| 75 | 68 | 32 |

Example 6

Synthesis of Crystalline Form of Monosodium Salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate Step 1: Synthesis of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate To a solution of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (obtained in Example 1) in ethanol (5 mL) was added sodium methoxide (0.596 mL, 1 equiv.) at room temperature. After stirring the reaction mixture for 30 minutes at room temperature, it was concentrated under vacuo to provide the desired mono sodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate as a white solid (1.73 g, 95.5%; melting point: 148-150° C.).

Step 2: Synthesis of crystalline form of monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate Mono sodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (500 mg) was transferred to a round bottom flask (100 mL) containing ethyl acetate (10 mL). Ethanol (3 mL) was added in portions (of 1 mL) and the flask was sonicated to completely dissolve the salt. After obtaining a clear solution, the flask was covered with a cotton plug and was left overnight at room temperature. The solid thus formed was filtered, washed with ethyl acetate (10 mL), dried and subjected to XRD (FIG. 3, prominent peaks are listed in Table 2) and DSC (FIG. 4) analysis.

Example 7

Synthesis of Crystalline Form of Diethanolamine Salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate The salt form was prepared using solvent vapor method. Small vial containing [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate (500 mg) was placed in an outer vial with ethanolamine (10 mL). The outer vial was sealed and kept at room temperature for 5 days. Small vial was taken out and solvents were evaporated to afford the crystalline diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate as pale yellow solid (510 mg; melting point: 178-182° C.).

Example 8

Synthesis of [4-chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl dihydrogen phosphate (Compound No. 9)

[Chem. 74]

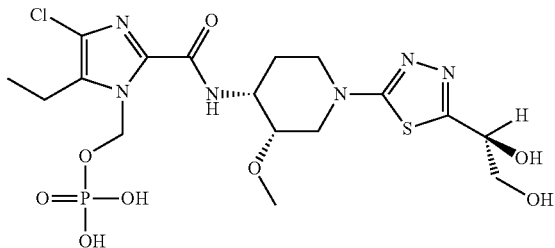

(Compound No. 9)

Step 1: Separation of di-tert-butyl (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl phosphate (Compound No. 3') and di-tert-butyl (5-chloro-2-{[(3S,4R)-1-{5-[(2R)-1,2-dihydroxypropan-2-yl]-1,3,4-thiadiazol-2-yl}-3-methoxy piperidin-4-yl]carbamoyl}-4-ethyl-1H-imidazol-1-yl) methyl phosphate (Compound No. 4')

Mixture of compound Compound No. 3' and Compound No. 4' (720 mg) was separated by describing below column condition to give Compound No. 3' (248 mg) and Compound No. 4' (115 mg).

Column: CHIRAL ART Cellulose-SC (5 µm) 250×30 mm I.D.

Eluent: n-hexane/ethanol (50/50).

Detection: UV at 275 nm.

Step 2: Synthesis of [4-chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl dihydrogen phosphate (Compound No. 9)

To a solution of di-tert butyl ester (Compound No. 3') (115 mg, 0.38 mmol) in methyl tert-butyl ether (8 ml), water (4 ml) and acetic acid (4 ml) were added. The mixture was stirred at room temperature for 1 day. The reaction mixture was concentrated and purified by HPLC (column; Inertsil PREP ODS 250×30 mm I.D., eluent; acetonitrile/0.1% aq. HCO2H, detection; UV at 275 nm), to give Compound No. 9 (145 mg, 70% yield) as colorless solid.

$^1$H-NMR (CD$_3$OD) δ ppm: 1.23 (3H, t, J=7.6 Hz), 1.80-1.83 (1H, m), 2.03 (1H, ddd, J=25.0, 12.4, 4.4 Hz), 2.79 (2H, q, J=7.6 Hz), 3.37-3.41 (3H, m), 3.44 (3H, s), 3.61 (1H, s), 3.74 (1H, dd, J=11.5, 6.1 Hz), 3.83 (1H, dd, J=11.5, 4.6 Hz), 3.92 (1H, d, J=13.8 Hz), 4.22-4.26 (2H, m), 6.29 (2H, d, J=8.4 Hz).

QTOF-MS (ES, negative ion mode): m/z calcd for C17H26ClN6O8PS: 540.1, found: 539.1 (M−1).

Example 9

Synthesis of (5-chloro-2-{[(3S,4R)-1-{5-[(1S)-1,2-dihydroxyethyl]-1,3,4-thiadiazol-2-yl}-3-methoxypiperidin-4-yl]carbamoyl}-4-ethyl-1H-imidazol-1-yl) methyl dihydrogen phosphate (Compound No. 10)

[Chem. 75]

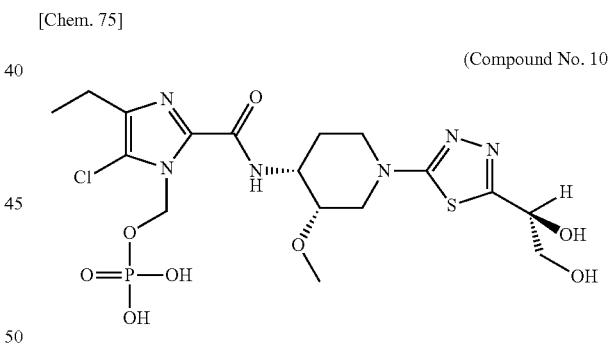

(Compound No. 10)

Deprotection of tert-butyl ester (Compound No. 4') was carried out described as preparation of Compound No. 9 (Example 8) to give Compound No. 10 (58.6 mg, 62%) as colorless solid.

$^1$H-NMR (CD3OD) δ ppm: 1.20 (3H, t, J=7.3 Hz), 1.82 (1H, dd, J=13.0, 3.8 Hz), 2.04 (1H, ddd, J=24.8, 12.6, 4.6 Hz), 2.58 (2H, q, J=7.6 Hz), 3.36 (1H, d, J=1.5 Hz), 3.39 (1H, d, J=1.5 Hz), 3.41 (1H, d, J=3.1 Hz), 3.44 (3H, s), 3.62 (1H, s), 3.74 (1H, dd, J=11.5, 5.4 Hz), 3.83 (1H, dd, J=11.5, 3.8 Hz), 3.92 (1H, d, J=13.8 Hz), 4.22-4.31 (2H, m), 6.29 (2H, dd, J 20=8.4, 3.1 Hz).

QTOF-MS (ES, negative ion mode): m/z calcd for C17H26ClN6O8PS: 540.1, found: 539.1 (M−1).

Example 10

Synthesis of (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate (Compound No. 3)

[Chem. 76]

(Compound No. 3)

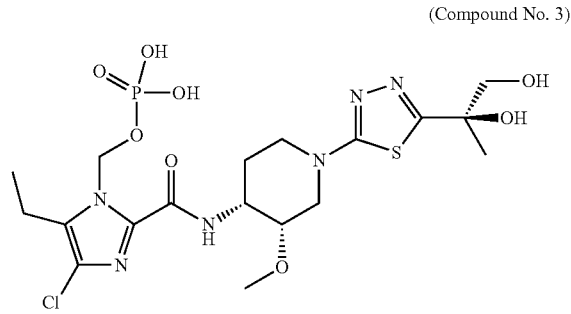

Step 1: Separation of di-tert-butyl (4-chloro-2-{[(3S,4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl phosphate (Compound No. 7') and di-tert-butyl (5-chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl phosphate (Compound No. 8')

Mixture of compound Compound No. 7' and Compound No. 8' (655 mg) was separated by describing below column condition to give Compound No. 7' (251 mg) and Compound No. 8' (129 mg).

Column: CHIRAL ART Cellulose-SC (5 μm) 250×30 mm I.D.
Eluent: n-hexane/ethanol (50/50).
Detection: UV at 275 nm.

Step 2: Synthesis of (4-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate (Compound No. 3)

Deprotection of tert-butyl ester (Compound No. 7') was carried out described as preparation of Compound No. 9 (Example 8) to give Compound No. 3 (135 mg, 65%) as colorless solid.

$^1$H-NMR (CD$_3$OD) δ ppm: 1.23 (3H, t, J=7.6 Hz), 1.77-1.85 (1H, m), 1.97-2.08 (1H, m), 2.79 (2H, q, J=7.6 Hz), 3.35-3.42 (3H, m), 3.44 (3H, s), 3.61 (1H, s), 3.74 (1H, dd, J=11.5, 6.1 Hz), 3.83 (1H, dd, J=11.5, 3.8 Hz), 3.93 (1H, d, J=13.8 Hz), 4.21-4.27 (2H, m), 6.29 (2H, d, J=8.4 Hz).
QTOF-MS (ES, negative ion mode): m/z calcd for C17H26ClN6O8PS: 540.1, found: 539.1 (M−1).

Example 11

Synthesis of and (5-chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl)methyl dihydrogen phosphate (Compound No. 4)

[Chem. 77]

(Compound No. 4)

Deprotection of tert-butyl ester (Compound No. 8') was carried out described as preparation of Compound No. 9 (Example 8) to give Compound No. 4 (40.2 mg, 38%) as colorless solid.

1H-NMR (CD$_3$OD) δ: 1.20 (3H, t, J=7.6 Hz), 1.82 (1H, d, J=9.2 Hz), 2.04 (1H, ddd, J=25.0, 12.4, 4.4 Hz), 2.58 (2H, q, J=7.6 Hz), 3.35 (1H, s), 3.37-3.42 (2H, m), 3.44 (3H, s), 3.61 (1H, s), 3.74 (1H, dd, J=11.5, 5.4 Hz), 3.83 (1H, dd, J=11.5, 4.6 Hz), 3.93 (1H, d, J=13.8 Hz), 4.21-4.31 (2H, m), 6.28 (2H, dd, J=8.4, 3.1 Hz).

QTOF-MS (ES, negative ion mode): m/z calcd for C17H26ClN6O8PS: 540.1, found: 539.1 (M−1).

Example 12

Synthesis of (4-chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 5)

[Chem. 78]

(Compound No. 5)

Step 1: Separation of di-tert-butyl (4-chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl phosphate (Compound No. 5') and di-tert-butyl (5-chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl phosphate (Compound No. 6')

Mixture of compound Compound No. 5' and Compound No. 6' (1.35 g mg) was separated by describing below column condition to give Compound No. 5' (663 mg) and Compound No. 6' (237 mg).

Column: CHIRALART Cellulose-SC (5 µm) 250×30 mm I.D.

Eluent: n-hexane/ethanol (50/50).

Detection: UV at 275 nm.

Step 2: Synthesis of (4-chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 5)

Deprotection of tert-butyl ester (Compound No. 5') was carried out described as preparation of Compound No. 9 (Example 8) to give Compound No. 5 (411 mg, 75%) as colorless solid.

1H-NMR (CD$_3$OD) δ: 1.23 (3H, t, J=7.6 Hz), 1.53 (3H, dd, J=6.9, 1.5 Hz), 1.78-1.84 (1H, m), 2.03 (1H, ddd, J=25.0, 12.4, 4.4 Hz), 2.79 (2H, q, J=7.6 Hz), 3.34-3.42 (2H, m), 3.44 (3H, s), 3.61 (1H, s), 3.88-3.95 (1H, m), 4.21-4.27 (2H, m), 4.97 (1H, q, J=6.1 Hz), 6.30 (2H, d, J=8.4 Hz).

QTOF-MS (ES, negative ion mode): m/z calcd for C17H26ClN6O7PS: 524.1, found: 523.1 (M−1).

Example 13

Synthesis of and (5-chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate (Compound No. 6)

[Chem. 79]

(Compound No. 6)

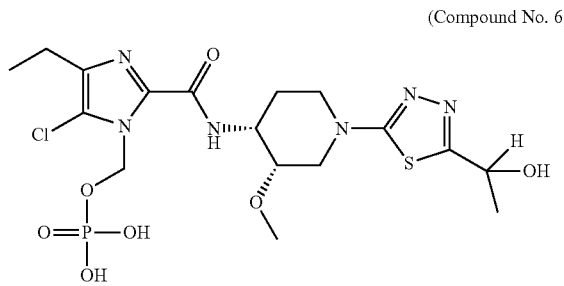

Deprotection of tert-butyl ester (Compound No. 6') was carried out described as preparation of Compound No. 9 (Example 8) to give Compound No. 6 (146 mg, 75%) as colorless solid.

1H-NMR (CD$_3$OD) δ: 1.21 (3H, t, J=7.6 Hz), 1.53-1.53 (3H, m), 1.80-1.85 (1H, m), 2.00-2.09 (1H, m), 2.58 (2H, q, J=7.6 Hz), 3.34-3.42 (2H, m), 3.45 (3H, s), 3.62 (1H, brs), 3.89-3.95 (1H, m), 4.22-4.30 (2H, m), 4.95-5.00 (1H, m), 6.25-6.33 (2H, m).

QTOF-MS (ES, negative ion mode): m/z calcd for C17H26ClN6O7PS: 524.1, found: 523.1 (M−1).

Biological Assay

A number of different assays can be utilized. In addition to assays mentioned hereinafter, one of ordinary skill in the art will know of other assays that can be utilized and can modify an assay for a particular application. Such assays and modification thereon are within the sprit and scope of the present invention.

Test Example 1

Method of Testing Solubility in Water and Neutral Buffer

A 10 mmol/L solution of the test compound was prepared in DMSO and dispensed 100 µL of 10 mmol/L DMSO stock solutions into labeled glass tubes in duplicate, one for Japanese Pharmacopeia First Fluid (JP1) and second for Japanese Pharmacopeia Second Fluid (JP2). After evaporation of DMSO from each tube, 500 µL of JP1 and JP2 fluid were added in each tube, respectively. These tubes were sonicated for 1 minute and placed on shaker for 30 minutes with an interval of 30 seconds at every 5 minute. Tubes were placed in dark at room temperature for 1 hour and solution was filtered through membrane filter. The filtrate was diluted 2-fold and 10-fold. The resulting test solutions was analyzed and quantified against the standards using UPLC (standard preparation-10 mmol/L solution in DMSO is serially diluted with 50% aqueous acetonitrile solution to prepare 2 solutions; 100 µmol/L standard solution and 5 µmol/L standard solutions).

TABLE 3

| | [Solubility, µg/mL] | |
|---|---|---|
| Compound No. | JP1 | JP2 |
| 1 | >1281 | >1320 |
| 2 | >1124 | >1095 |
| 3 | >1349 | >1321 |
| 4 | >1282 | >1511 |

Parent compounds: About 5 mg of parent compounds (biologically active forms of prodrugs) were added to 950 µL of phosphate buffer, and mixed vigorously for 1 hour at 25° C. Then, these samples were stored at 25° C. for more than 4 weeks and filtered to remove undissolved parent compounds. Next, these solutions were diluted with 50% aqueous acetonitrile solution. The resulting test solutions were assayed by HPLC.

Prodrugs: About 30 mg of prodrugs were added to 120 μL of phosphate buffer, and mixed vigorously for 1 hour at 25° C. After shaking, pH of these solutions were adjusted at pH 7.0 by 1 mol/L NaOH solution. Then, the total volume were adjusted to 280 μL with purified water. Next, these solutions were stored at 25° C. for more than 4 weeks and filtered to remove undissolved compounds. These solutions were diluted with 50% aqueous acetonitrile solution. The resulting test solutions were assayed by HPLC.

TABLE 4

Solubility of parent compounds and prodrugs

| Compounds | | Solubility (mg/mL) | pH |
|---|---|---|---|
| Compound A | Parent compound | 0.7750 | 7.0 |
| Compound No. 3 | Prodrug | 107.1 | 7.0 |
| Compound No. 4 | Prodrug | 102.0 | 7.0 |
| Compound B | Parent compound | 0.3800 | 7.0 |
| Compound No. 9 | Prodrug | 101.9 | 7.2 |
| Compound No. 10 | Prodrug | 105.3 | 7.0 |
| Compound C | Parent compound | 2.442 | 7.0 |
| Compound No. 7 | Prodrug | 106.7 | 7.0 |
| Compound No. 8 | Prodrug | 101.7 | 7.0 |
| Compound D | Parent compound | 0.7517 | 7.0 |

TABLE 4-continued

Solubility of parent compounds and prodrugs

| Compounds | | Solubility (mg/mL) | pH |
|---|---|---|---|
| Compound No. 5 | Prodrug | 101.3 | 7.0 |
| Compound No. 6 | Prodrug | 103.8 | 7.0 |

Compound A is parent compound of compounds No. 3 and No. 4.
Compound B is parent compound of compounds No. 9 and No. 10.
Compound C is parent compound of compounds No. 7 and No. 8.
Compound D is parent compound of compounds No. 5 and No. 6.

Test Example 2

Method of Testing Conversion Efficiency

Determination of conversion efficiency of Compound No. 1 and Compound No. 2 was conducted in rodents (mice and rats) and non-rodents (monkeys and dogs). Animals were divided in two groups with two animals in each group. One group received an intravenous (IV) dose of prodrug and the other group received an IV dose of parent compound. The dose of prodrug was taken as molar equivalent dose of parent compound. Serial blood sampling was carried out at 0.083, 0.33, 1, 2, 4, 8 and 24 h post IV dose from both the animal groups. Blood samples were centrifuged to harvest plasma. Plasma samples were stored at −80° C. until analysis. Plasma samples of prodrug administered animals were simultaneously analyzed for both analytes (prodrug and parent compound) using LC-MS/MS. Area under the curve (AUC) of plasma concentrations versus time profiles were calculated in WinNonlin software and percentage conversion efficiency was determined using the formula: Percentage conversion efficiency=(AUC$_{iv}$ of parent compound (from prodrug administered samples)×100/(AUC$_{iv}$ of parent compound (from parent compound administered samples). PK profile of Compounds No. 1 and No. 2 in rats, dogs and monkeys are depicted in Table 5 and 6, respectively (also shown in FIGS. 1 and 2).

TABLE 5

PK Profile of Compound No. 1

| | | Analyze Measured | | | Analyze | |
|---|---|---|---|---|---|---|
| Species | Dose (IV) (mg/kg) Compound No. 1 | Compound No. 1 AUCinf (μg · h/mL) | Parent compound (derived) AUCinf (μg · h/mL) | Dose (IV) (mg/kg) Parent compound | Measured Parent compound AUCinf (μg · h/mL) | Conversion Efficiency % |
| Monkey | 1.256 | 0 | 5.14 | 1 | 6.25 | 82 |
| Dog | 1.256 | 0 | 22.4 | 1 | 29.45 | 76 |
| Rat | 15.300 | 0.27 | 14.81 | 12.5 | 17.66 | 84 |

ATTN. CWU: Shading has been verified to be removed.

TABLE 6

PK Profile of Compound No. 2

| | | Analyze Measured | | | Analyze | |
|---|---|---|---|---|---|---|
| Species | Dose (IV) (mg/kg) Compound No. 2 | Compound No. 2 AUCinf (μg · h/mL) | Parent compound (derived) AUCinf (μg · h/mL) | Dose (IV) (mg/kg) Parent compound | Measured Parent compound AUCinf (μg · h/mL) | Conversion Efficiency % |
| Monkey | 1.256 | 0 | 3.71 | 1 | 6.25 | 59 |
| Dog | 1.256 | 0 | 23.9 | 1 | 29.45 | 81 |
| Rat | 5 | 0 | 2.25 | 12.5 | 17.66 | 40 |

ATTN. CWU: Shading has been verified to be removed.

Determination of conversion efficiency of Compound No. 5 and Compound No. 7 was conducted in rats. Animals were divided in two groups with two animals in each group. One group received an IV dose of prodrug and the other group received an IV dose of parent compound. Serial blood sampling was carried out at 0.08, 0.25, 0.5, 1, 2, 4, 7, and 24 h post dose from both of the animal groups. Blood samples were centrifuged to harvest plasma. Plasma samples of prodrug administered animals were simultaneously analyzed for both analytes (prodrug and parent compound) using LC-MS/MS. AUC of plasma concentrations versus time profiles were calculated in WinNonlin software and percentage conversion efficiency was determined using the formula: Percentage conversion efficiency=(AUC$_{iv}$ of parent compound from prodrug administered samples)/(AUC$_{iv}$ of parent compound from parent compound administered samples)/(molecular weight of parent compound)×(molecular weight of prodrug)×100. PK profile of Compound No. 5 and Compound No. 7 in rats are depicted in Table 7.

TABLE 7

PK Profile of Compound No. 5 and Compound No. 7

| Compound | Dose (IV) (mg/kg) Prodrug | Analyze Measured | | Dose (IV) (mg/kg) Parent compound | Analyze Measured Parent compound AUCinf (µg · h/mL) | Conversion Efficiency % |
|---|---|---|---|---|---|---|
| | | Prodrug AUCinf (µg · h/mL) | Parent compound (derived) AUCinf (µg · h/mL) | | | |
| Compound No. 5 | 1 | 0 | 2.26 | 1 | 3.11 | 92 |
| Compound No. 7 | 1 | 0 | 0.91 | 1 | 0.99 | 116 |

Test Example 3 a) Method for Testing Therapeutic Effect of Compounds Using Mouse Lung Infection Model by MRSA 562

Mice were rendered neutropenic with two intra-peritoneal injections (IP) of cyclophosphamide on day −4 and day −1 prior to infection at the dose rate of 150 mg and 100 mg per kg body weight. Overnight grown MRSA 562 was diluted 1:10 in fresh Brain Heart Infusion broth and mixed 1:1 with 5% hog mucin. The bacterial suspension (3.16×10$^6$/mouce/50 µL) was then inoculated to each pre-anaesthetized mice (xylazine 5 mg/kg and ketamine 100 mg/kg mixture) into the nares of Swiss mice (4 to 6-week-old, Vivo Biotech Limited, Hyderabad, India), n=5 mice per group). The test compound was administered to the mice once, twice and four times at an interval of 24, 12 and 6 hr, respectively. The number of bacteria in the lungs was determined in the non-treated group immediately before initial administration of the test compound (pre-control) and in the non-treated group (post-control) and the test compound-administered group on the next day of administration of the test compound and infection. A change in the number of bacteria in the lungs was used as an index of therapeutic effect.

The exemplified compounds, for example Compound No. 1, exhibited the therapeutic effect by this test method. Compound No. 1 showed 1.33 log$_{10}$ and 2.52 log$_{10}$ kill at 6.25 mg/kg/dose, SC q6h as compared to 1 hour pre-control and 25 hour post control, respectively. Similarly at 12.5 mg/kg/dose, SC, q6h, it showed 1.76 log$_{10}$ and 2.95 log$_{10}$ kill as compared to 1 hour pre-control and 25 hour post control, respectively.

(b) Method for Testing Therapeutic Effect of Compounds Against MRSA 02541 and VRE IV258 21076 Using Neutropenic Mouse Thigh Infection Model Swiss Webster mice of 4 to 6-week-old were used for this experiments (Vivo Biotech Limited, Hyderabad, India, n=5 mice per group). Mice were rendered neutropenic as described above. Overnight grown culture of MRSA 02541 on Mueller-Hinton broth (MHB) was adjusted to 0.5 Mac Farland. The suspension was then diluted 1:100 in fresh MHB and 100 µl was injected intra-muscularly in the right thigh muscles of the mice (n=5/group). In case of VRE IV 258-21076 culture was mixed with 10% hog mucin in 1:1 proportion. The bacterial inocula were confirmed by quantitative culture analyses and found to be 3×10$^6$ CFU for MRSA and 2×10$^6$ for VRE IV258-21076 per mL. Treatment started 2 h post infection. The test compound was administered to the mice one to eight times at an interval of 3 to 24 hr. The number of bacteria in the thigh muscle was counted for the non-treated group immediately before initial administration of the test compound (pre-control), for the non-treated group (post-control) and for the test compound-administered group on the next day of administration of the test compound and infection. A change in the number of bacteria in the thigh was used as an index of therapeutic effect.

The exemplified compounds, for example, Compound No. 1, exhibited the therapeutic effect by this test method. Against MRSA 02541, Compound No. 1 showed cidal potential at 200 mg/kg/dose q24h, 100 mg/kg/dose q24h, and 50 mg/kg/dose q24h and their fractions irrespective of dosing schedule. Against VRE IV-258 21076, Compound No. 1 at fractionated doses 50 mg/kg/dose q12h, 25 mg/kg/dose q6h, 12.5 mg/kg/dose q3h exhibited cidal potential.

c) Method for Testing Therapeutic Effect of Compounds Against MRSA 02541 Using Neutropenic Sprague Dawley Rat Thigh Infection Model Sprague Dawley rats of 4 to 6-week-old were used for this experiments (Vivo Biotech Limited, Hyderabad, India, n=4 rats per group). Rats were rendered neutropenic by intraperitoneal injection of cyclophosphamide. Overnight grown culture of MRSA 02541 in MHB was adjusted to 0.5 Mac Farland. The suspension was then diluted 1:10 in fresh MHB and 200 µl was injected intra-muscularly in the right thigh muscles of the rat. The bacterial inocula were confirmed by quantitative culture analyses and found to be 6×10$^6$ CFU per rat thigh muscle. Treatment started 2 h post infection. The test compound was administered to the rat four times at an interval of 6 hr. The number of bacteria in the thigh muscle was counted for the non-treated group immediately before initial administration of the test compound (2 h pre-control), for the non-treated group (26 h post-control) and for the test compound-administered group on the next day of administration of the test compound and infection. A change in the number of bacteria in the thigh was used as an index of therapeutic effect.

The exemplified compounds, for example, Compound No. 1, exhibited the therapeutic effect by this test method. Compound No. 1 showed 1 $\log_{10}$ and 2.99 $\log_{10}$ kill at 25 mg/kg, IV qid as compared to 2 hours pre-control and 26 hours post control, respectively.

d) Method for Testing Therapeutic Effect of Compounds in Hamster CDI Model

The in vivo efficacy of Compound No. 1 was evaluated in a hamster CDI model caused by *Clostridium difficile* 2009155, a NAP1/027 strain. The Syrian hamsters (7-9 weeks old, National Centre for Laboratory Animal Sciences, National Institute Nutrition, Hyderabad, India.) were acclimatized at least 7 days prior the experiment. Hamsters primed with a single subcutaneous injection of clindamycin (30 mg/kg) 1 day prior to infection. Hamsters were infected by oral gavage with 1 mL of spore suspension (2-3×10⁵) prepared in PBS. The test compounds were prepared using the 0.25 w/v % Methyl Cellulose Solution for oral administration and 10% HP ß-CD for SC administration and treatment was started 6 h post infection at an interval of 24 h for 5 days. Hamsters were administered a dose of 0.03-0.3 mg/kg/day for 5 days. The death and survival time of the hamsters treated with test compound administered group and non-treated group (vehicle-control) were recorded once daily for 35 days and were compared. A change in the survival time was used as an index of therapeutic effect.

The compounds disclosed herein exhibited therapeutic effect in this test method, for example, Compounds No. 1 and No. 2 exhibited 100% survival on day 35 at 0.3 mg/kg/day.

The invention claimed is:

1. A compound represented by formula (I), a regioisomer thereof, or a pharmaceutically acceptable salt thereof:

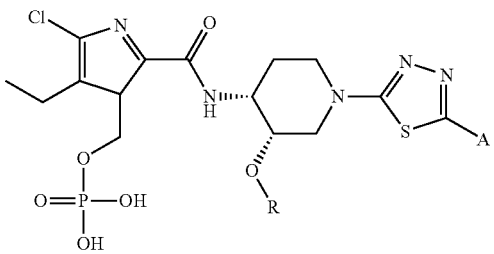

wherein R represents (C₁-C₃) alkyl, and
A represents the following formulae:

[Chem. 2]

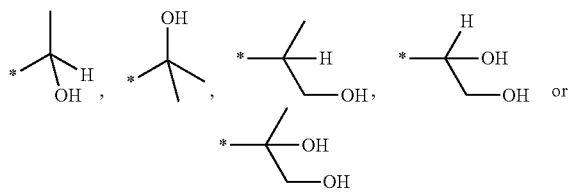

provided that, in formula (I), regioisomers with the N-phosphonoxymethyl group present at different positions of the imidazole ring are included.

2. The compound or a regioisomer thereof or a pharmaceutically acceptable salt thereof according to claim 1, wherein the compound of formula (I) has the structure:

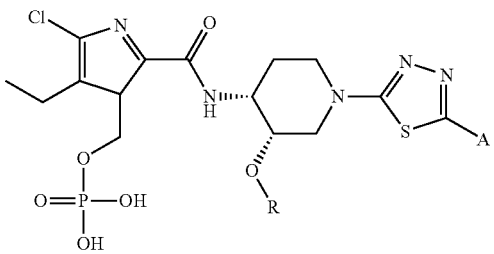

wherein R represents (C₁-C₃) alkyl, and
A represents the formulae:

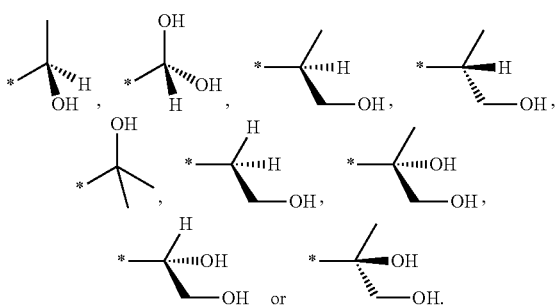

3. The compound, a regioisomer, a stereoisomer, or a pharmaceutically acceptable salt thereof according to claim 1, wherein R represents methyl or ethyl.

4. The compound according to claim 1, wherein the compound is selected from the group consisting of:
[4-Chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate,
[5-Chloro-4-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate,
(4-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-5-ethyl-1H-imidazol-1-yl)methyl dihydrogen phosphate,
(5-Chloro-2-{[(3S,4R)-1-{5-[(2R)-1,2-dihydroxypropan-2-yl]-1,3,4-thiadiazol-2-yl}-3-methoxypiperidin-4-yl]carbamoyl}-4-ethyl-1H-imidazol-1-yl)methyl dihydrogen phosphate,
(4-Chloro-5-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate,
(5-Chloro-4-ethyl-2-{[(3S,4R)-1-{5-[(1S)-1-hydroxyethyl]-1,3,4-thiadiazol-2-yl}-3-methoxypiperidin-4-yl]carbamoyl}-1H-imidazol-1-yl)methyl dihydrogen phosphate,
(4-Chloro-2-{[(3S,4R)-1-{5-[(1R)-1,2-dihydroxyethyl]-1,3,4-thiadiazol-2-yl}-3-methoxypiperidin-4-yl]carbamoyl}-5-ethyl-1H-imidazol-1-yl)methyl dihydrogen phosphate, (5-Chloro-2-{[(3S,4R)-1-{5-[(1R)-1,2-dihydroxyethyl]-1,3,4-thiadiazol-2-yl}-3-methoxypiperidin-4-yl]carbamoyl}-4-ethyl-1H-imidazol-1-yl)methyl dihydrogen phosphate,

[4-Chloro-2-({(3S,4R)-1-[5-(1,2-dihydroxyethyl)-1,3,4-thiadiazol-2-yl]-3-methoxypiperidin-4-yl}carbamoyl)-5-ethyl-1H-imidazol-1-yl]methyl dihydrogen phosphate, (5-Chloro-2-{[(3S,4R)-1-{5-[(1S)-1,2-dihydroxyethyl]-1-1,3,4-thiadiazol-2-yl}-3-methoxypiperidin-4-yl]carbamoyl}-4-ethyl-1H-imidazol-1-yl)methyl dihydrogen phosphate, and pharmaceutically acceptable salts thereof.

5. A compound, which is monosodium salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate in crystalline solid, characterized by powder x-ray diffraction (XRD) having characteristic peaks at interplanar spacings d of 20.12, 7.10, 6.34, 5.94, 5.46, 4.79, 4.49, 4.23, 3.71, 3.36 angstroms, all in powder X-ray diffraction obtained through irradiation with copper Kα radiation (wavelength λ=1.54 angstroms).

6. A compound, which is diethanolamine salt of [4-chloro-5-ethyl-2-({(3S,4R)-1-[5-(2-hydroxypropan-2-yl)-1,3,4-thiadiazol-2-yl]-3-methoxypiperidin-4-yl}carbamoyl)-1H-imidazol-1-yl]methyl dihydrogen phosphate in crystalline solid, characterized by powder x-ray diffraction (XRD) having characteristic peaks at interplanar spacings d of 5.45, 5.24, 4.22, 4.08, 3.96, 3.74, 3.62, 3.33, 3.11, 2.89, all in powder X-ray diffraction obtained through irradiation with copper Kα radiation (wavelength λ=1.54 angstroms).

7. A pharmaceutical composition comprising a therapeutically effective amount of a compound, a regioisomer, a stereoisomer, or a pharmaceutically acceptable salt thereof according to claim 1, as its active ingredient.

8. A method for treating bacterial infectious disease in a patient comprising administering to said patient a therapeutically effective amount of a compound, or a regioisomer thereof, or a pharmaceutical salt thereof, according to claim 1.

9. A pharmaceutical composition comprising a therapeutically effective amount of a compound in crystalline solid according to claim 5, as its active ingredient.

10. A pharmaceutical composition comprising a therapeutically effective amount of a compound in crystalline solid according to claim 6, as its active ingredient.

11. A method for treating bacterial infectious disease in a patient comprising administering to said patient a therapeutically effective amount of a compound in crystalline solid according to claim 5.

12. A method for treating bacterial infectious disease in a patient comprising administering to said patient a therapeutically effective amount of a compound in crystalline solid according to claim 6.

* * * * *

UNITED STATES PATENT AND TRADEMARK OFFICE
CERTIFICATE OF CORRECTION

Page 1 of 2

PATENT NO. : 10,752,647 B2
APPLICATION NO. : 16/492027
DATED : August 25, 2020
INVENTOR(S) : M. Khera et al.

It is certified that error appears in the above-identified patent and that said Letters Patent is hereby corrected as shown below:

In the Claims

| Column | Line | |
|---|---|---|
| 71 | 55 | Please remove "[Chem 2]" |
| 72 | 6-15 | Delete " 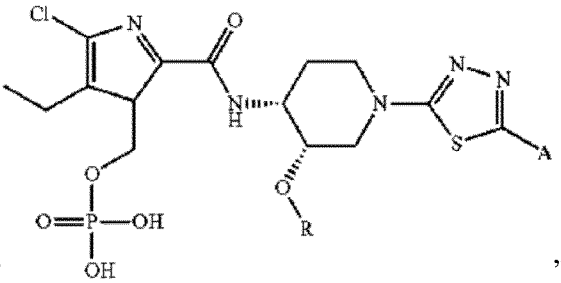 " and insert " 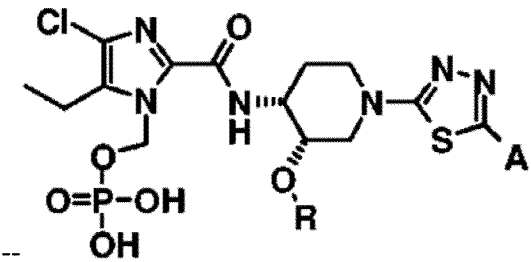 " -- |
| 72 | 21-33 | Delete " 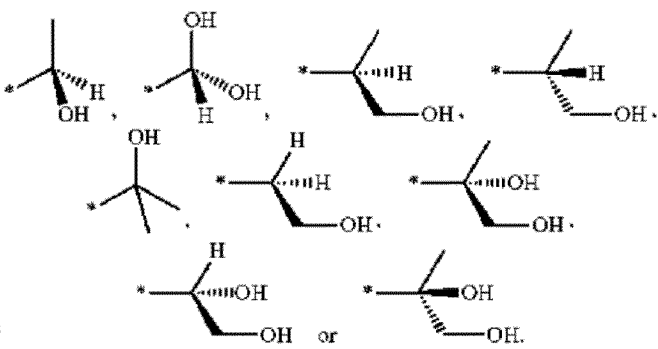 " and |

Signed and Sealed this
Fifth Day of November, 2024

Katherine Kelly Vidal
*Director of the United States Patent and Trademark Office*

CERTIFICATE OF CORRECTION (continued)
U.S. Pat. No. 10,752,647 B2 insert -- 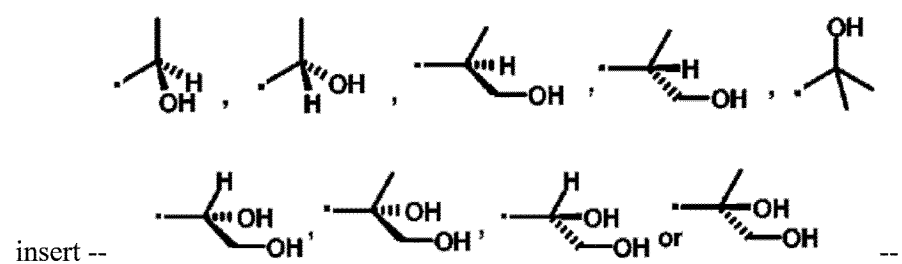 --